United States Patent
Wainer et al.

(10) Patent No.: US 11,389,415 B2
(45) Date of Patent: *Jul. 19, 2022

(54) METHODS OF REGULATING CANNABINOID RECEPTOR ACTIVITY-RELATED DISORDERS AND DISEASES

(71) Applicant: The United States of America as represented by the Secretary, Department of Health and Human Services, Bethesda, MD (US)

(72) Inventors: Irving W. Wainer, Washington, DC (US); Michel Bernier, Pikesville, MD (US); Rajib K. Paul, Baltimore, MD (US)

(73) Assignees: The United States of America, as Represented by the Secretary, Department of Health and Human Services, Bethesda, MD (US); Secretary, Department of Health and Human Services, Bethesda, MD (US)

( * ) Notice: Subject to any disclaimer, the term of this patent is extended or adjusted under 35 U.S.C. 154(b) by 34 days.

This patent is subject to a terminal disclaimer.

(21) Appl. No.: 16/992,742

(22) Filed: Aug. 13, 2020

(65) Prior Publication Data
US 2021/0038540 A1 Feb. 11, 2021

Related U.S. Application Data

(63) Continuation of application No. 16/600,234, filed on Oct. 11, 2019, now Pat. No. 10,772,849, which is a continuation of application No. 16/129,569, filed on Sep. 12, 2018, now Pat. No. 10,485,771, which is a continuation of application No. 15/225,643, filed on Aug. 1, 2016, now Pat. No. 10,130,593, which is a continuation of application No. 14/403,516, filed as application No. PCT/US2013/042457 on May 23, 2013, now abandoned.

(60) Provisional application No. 61/789,629, filed on Mar. 15, 2013, provisional application No. 61/651,961, filed on May 25, 2012.

(51) Int. Cl.
*A61K 31/137* (2006.01)
*A61K 45/06* (2006.01)
*A61K 31/05* (2006.01)

(52) U.S. Cl.
CPC ............ *A61K 31/137* (2013.01); *A61K 31/05* (2013.01); *A61K 45/06* (2013.01)

(58) Field of Classification Search
CPC ...... A61K 31/05; A61K 31/137; A61K 45/06; A61P 35/00; A61P 43/00
See application file for complete search history.

(56) References Cited

U.S. PATENT DOCUMENTS

2006/0194260 A1 8/2006 Drmota et al.
2013/0101672 A1 4/2013 Cheng et al.

FOREIGN PATENT DOCUMENTS

WO WO 2011/112867 9/2011

OTHER PUBLICATIONS

Bowel Cancer (Year: 2003).*
Bukowski et al., "Randomized Trial of 5-Fluorouracil and Mitomycin C with or without Streptozotocin for Advanced Pancreatic Cancer," *Cancer*, vol. 52, 1577-1582, 1983.
Coelho et al., "Antiproliferative effects of β-blocks on human colorectal cancer cells," *Oncology Reports* 2015, 33:2513-2520.
Curran et al., "The Synthetic Cannabinoid R(+)WIN 55,212-2 Inhibits the Interleukin-1 Signaling Pathway in Human Astrocytes in a Cannabinoid Receptor-Independent Manner," *J Biol Chem* 2005, 280(43):35797-35806.
Gura, et al., "Systems for Identifying New Drugs are often Faulty," *Science*, pp. 1041-1042, 1997.
Hart, et al., "Cannabinoids Induce Cancer Cell Proliferation via Tumor Necrosis Factor α-Converting Enzyme (TACE/ADAM17)-Mediated Transactivation of the Epidermal Growth Factor Receptor," *Cancer Research*, vol. 64, pp. 1943-1950, Mar. 15, 2004.
Hu, et al., "The Putative Cannabinoid Receptor GPR55 Promotes Cancer Cell Proliferation," *Oncogene*, vol. 30, pp. 139-141, 2011.
International Search Report and Written Opinion issued by the European Patent Office dated Aug. 28, 2013, for corresponding PCT Patent Application No. PCT/US2013/042457, filed May 23, 2013, 12 pp.
Johnson, et al., Relationships Between Drug Activity in NCI Preclinical in vitro and in vivo Models and Early Clinical Trials, *British J. of Cancer*, pp. 1424-1431, 2001.
Jozwiak et al., "Comparative molecular field analysis of fenoterol derivatives: A platform towards highly selective and effective $\beta_2$-adrenergic receptor agonists," Bioorganic & Medicinal Chemistry, vol. 18, No. 2, pp. 728-736, Jan. 15, 2010.
Kim et al., "The Role of Chemotherapy in Anaplastic Astrocytoma Patients," *J. Korean Neurosurgery Society*, vol. 51, 199-202. 2012.

(Continued)

*Primary Examiner* — Umamaheswari Ramachandran
(74) *Attorney, Agent, or Firm* — Klarquist Sparkman, LLP

(57) ABSTRACT

This disclosure concerns the discovery of the use of fenoterol analogues for regulating cannabinoid (CB) receptor activity-related disorders and disease, such as dysregulated CB receptors, including treating a disorder or disease, such as a glioblastoma, hepatocellular carcinoma, liver cancer, colon cancer, and/or lung cancer, which is associated with altered cannabinoid receptor activity. In one example, the method includes administering to a subject having or at risk of developing a disorder or disease regulated by CB receptor activity an effective amount of a fenoterol analogue to reduce one or more symptoms associated with the disorder or disease regulated by CB receptor activity.

14 Claims, 30 Drawing Sheets
Specification includes a Sequence Listing.

(56) References Cited

OTHER PUBLICATIONS

Michalski, et al., "Cannabinoids in pancreatic cancer: Correlation with survival and pain," *Int. J. Cancer* 2008, 122:742-750.
Office Action, dated Jan. 6, 2017, issued in corresponding Australian Application No. 2013266235, 4 pages.
Office Action, dated Oct. 13, 2016, issued in corresponding Japanese Patent Application No. 2015-514191.
Pertwee, "GPR55: A new member of the Cannabinoid Receptor Clan?" *British Journal of Pharmacology*, vol. 152, pp. 984-986, 2007.
Pisanti et al., "Use of cannabinoid receptor agonists in cancer therapy as palliative and curative agents," *Best Practice & Research Clinical Endocrinology & Metabolism*, vol. 23, No. 1, pp. 117-131, Mar. 11, 2009.
Prabhu et al., "Preliminary biological evaluation and mechanism of action studies of selected 2-arylindoles against glioblastoma," *Bioorganic & Medicinal Chemistry*, vol. 21, 1918-1924, 2013.
Prabhu et al., "Towards Establishing the Effects and Mechanism of Action of a Series of Indoles in an in vitro Chemosensitive System for Glioma Treatment," *Neuro-Oncology*, Oct. 2011, 1 page.
Saito, et al., "Study of Mechanism of 1321N1 Human Astrocytoma Cells Apoptosis Induction by Synthetic Cannabinoid CP55940," Collected Abstracts of Annual Congress of the Pharmaceutical Society of Japan, 2007, 127(2), 11, 30N-pm08, 1 page.
Stock et al., "Norepinephrine inhibits the migratory activity of pancreatic cancer cells," *Experimental Cell Research* 2013, 319:1744-1758.
"Tissue expression of GPR55—Summary," *The Human Protein Atlas* http://www.proteinatlas.org/ENSG00000135898-GPR55/tissue; http://www.proteinatlas.org/ENSG00000135898-GPR55/pathology/tissue/pancreatic+cancer, http://www.proteinatlas.org/ENSG00000135898-GPR55/pathology/tissue/glioma, 10 pages, downloaded Oct. 9, 2017.
Toll, et al., "$\beta_2$-Adrenergic Receptor Agonists Inhibit the Proliferation of 1321N1 Astrocytoma Cells," *The J. of Pharmacology and Experimental Therapeutics*, pp. 524-534, 2011.
Wu et al., "4-(Methylnitrosamino)-1-(3-Pyridyl)-1-Butanone from Cigarette Smoke Stimulates Colon Cancer Growth via $\beta$-Adrenoceptors," *Cancer Res.* 2005, 65(12):5272-5277.
Yuan et al., "The mitogenic effectors of isoproterenol in human hepatocellular carcinoma cells," *Oncology Reports* 2010, 23:151-157.

\* cited by examiner

FIG. 1A
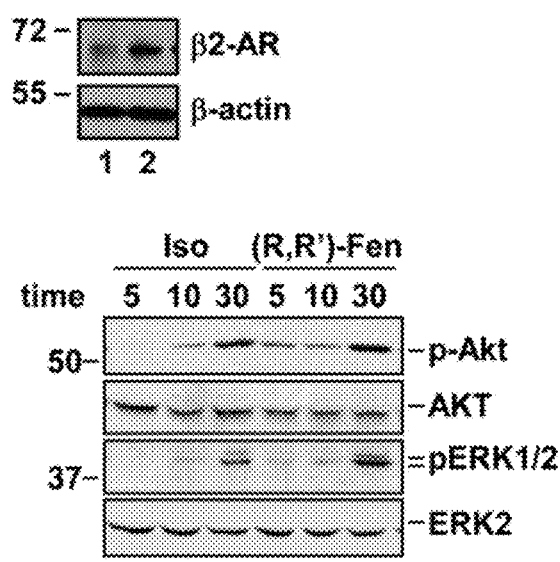
FIG. 1C
FIG. 1B
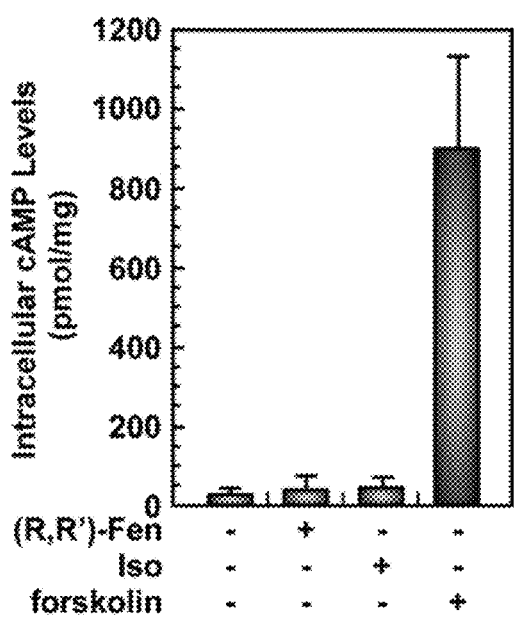

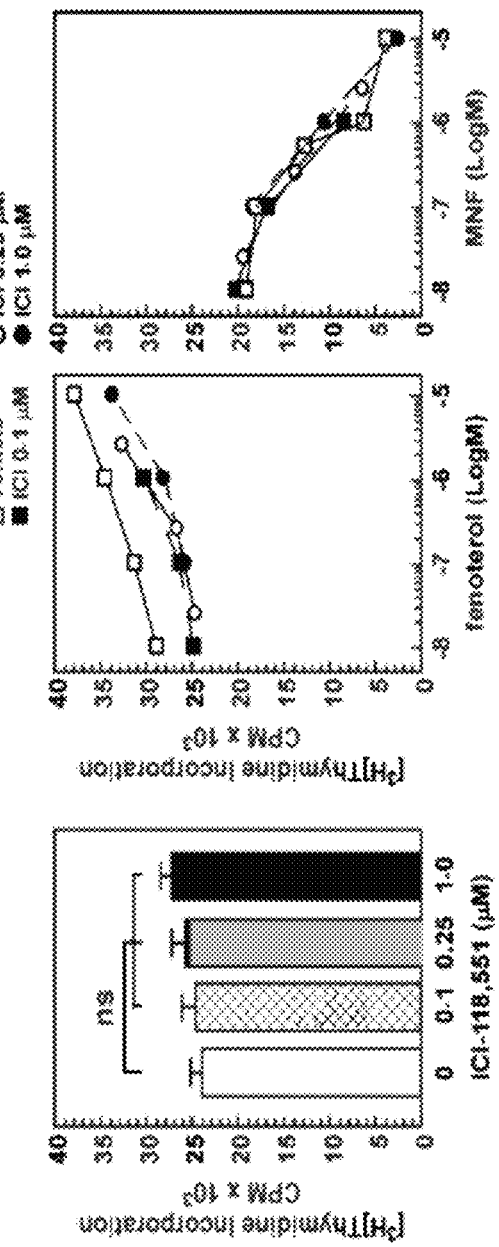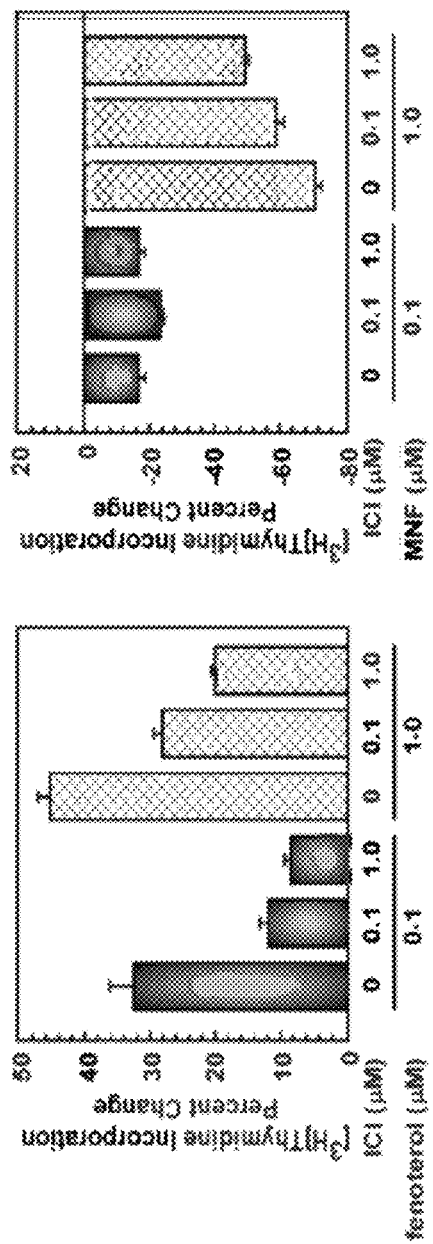

FIG. 8A
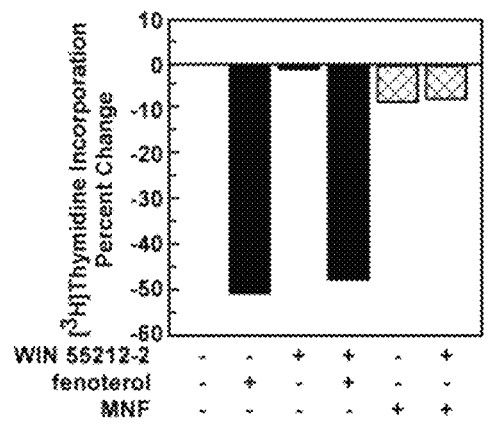
FIG. 8B
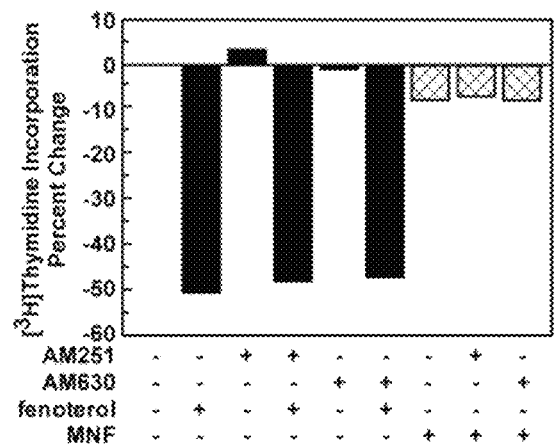
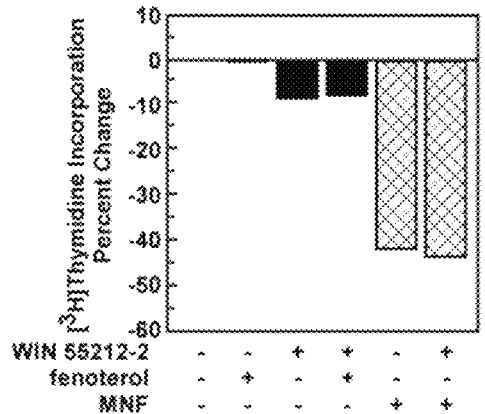
FIG. 8C
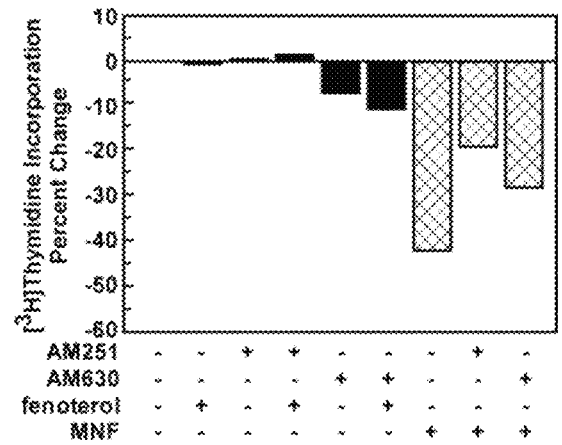
FIG. 8D

FIG. 20A
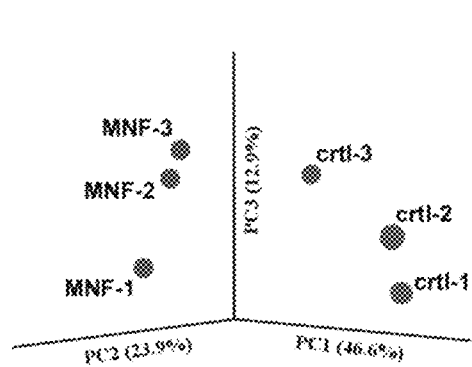
FIG. 20B
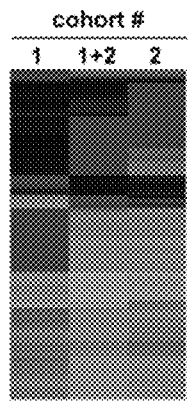
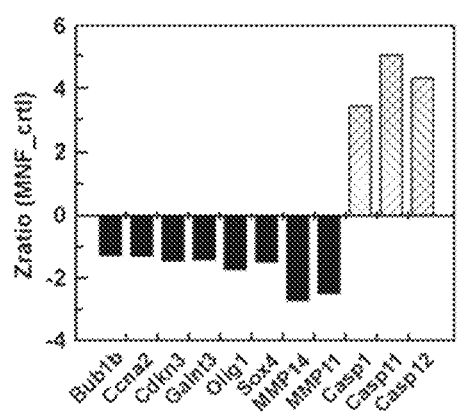
FIG. 20C
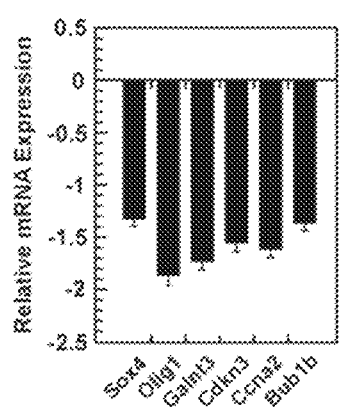
FIG. 20D

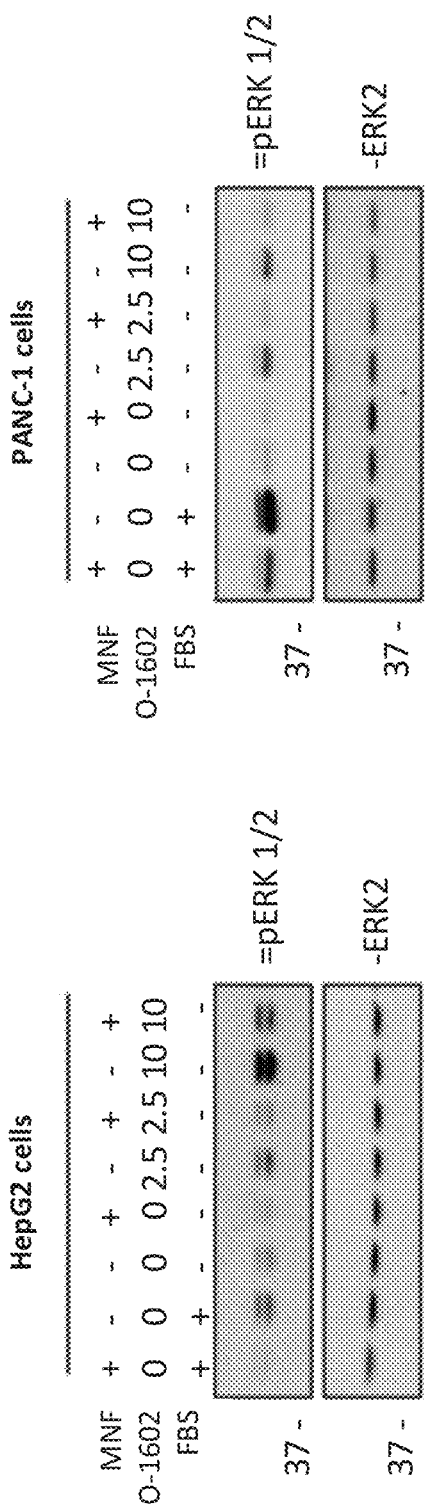
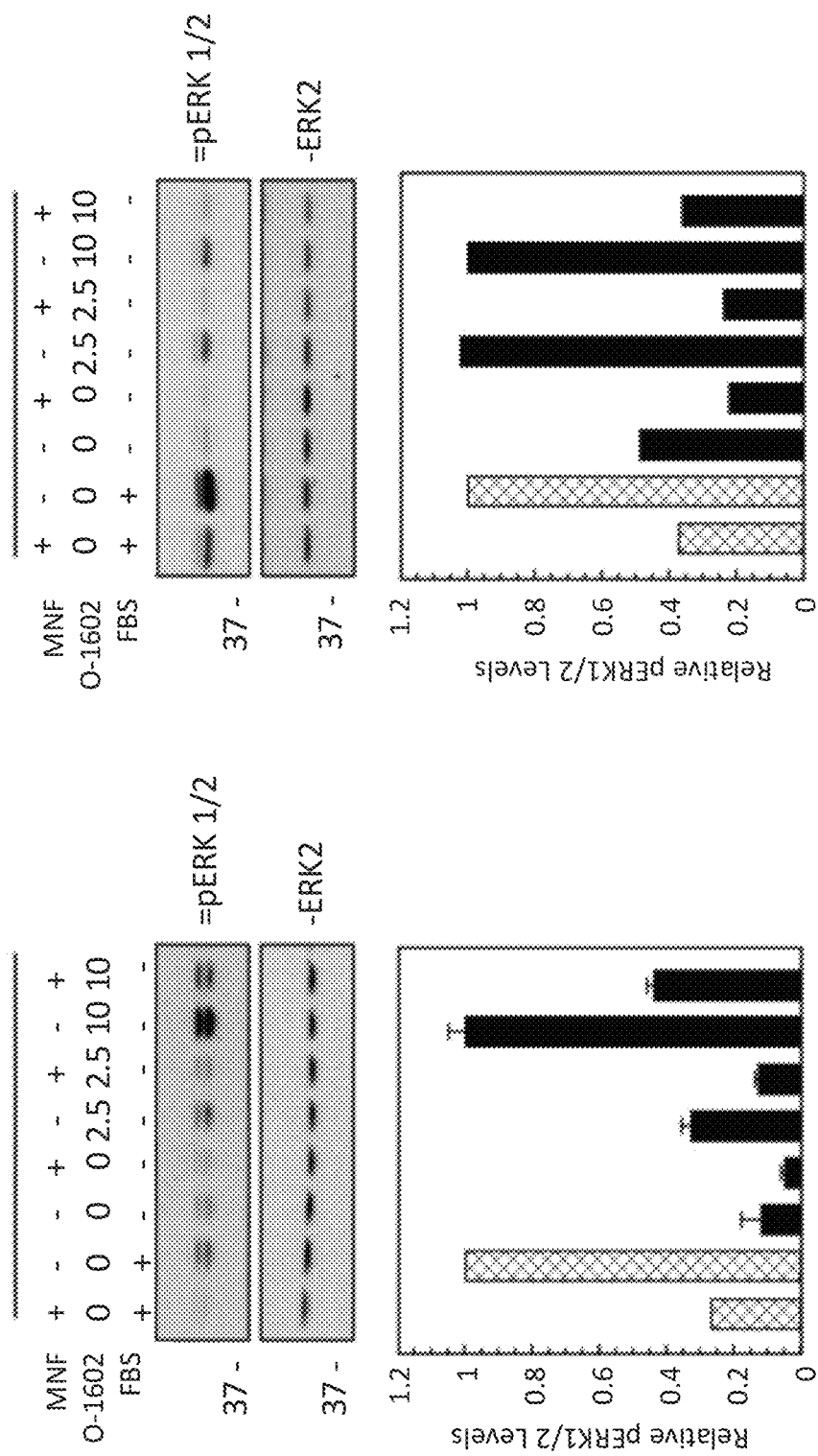

FIG. 27A
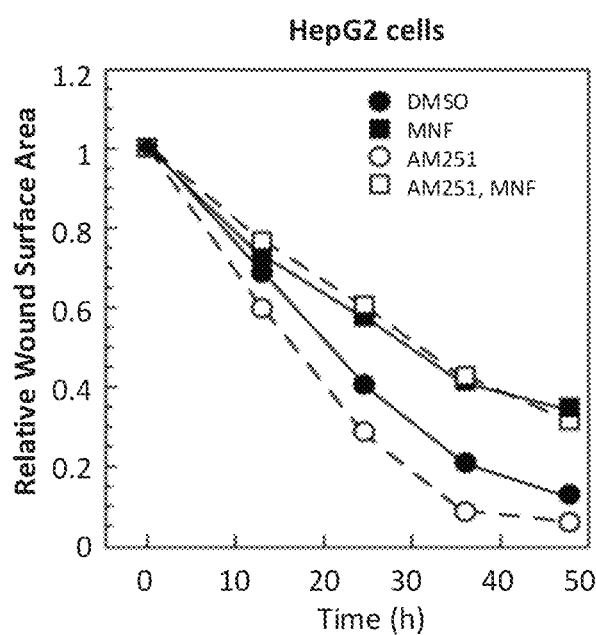
FIG. 27B
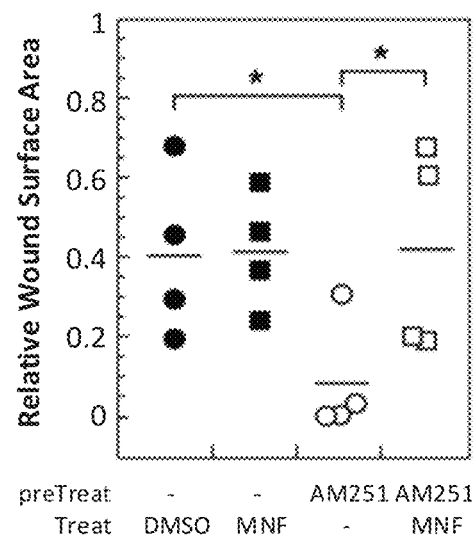
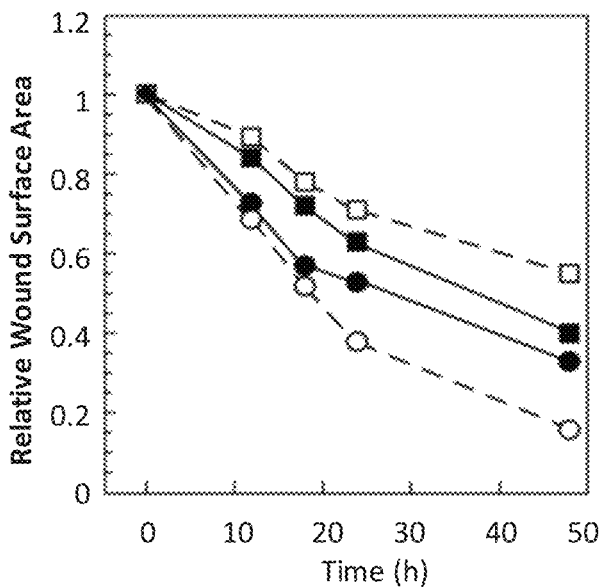
FIG. 27C
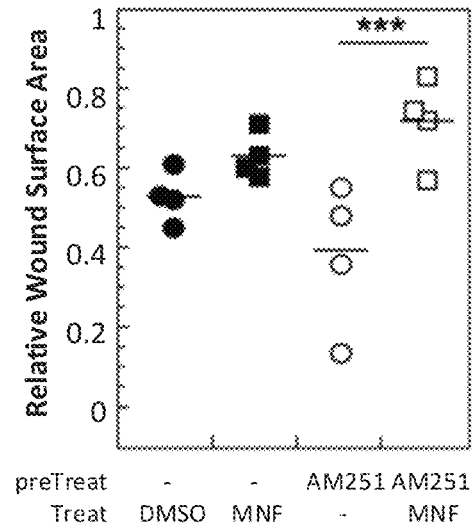
FIG. 27D

5-TAMRA-3-phenylpropylamine      T1117

METHODS OF REGULATING CANNABINOID RECEPTOR ACTIVITY-RELATED DISORDERS AND DISEASES

CROSS REFERENCE TO RELATED APPLICATIONS

This is a continuation of U.S. application Ser. No. 16/600,234, filed Oct. 11, 2019, now U.S. Pat. No. 10,772,849, which is a continuation of U.S. application Ser. No. 16/129,569, filed Sep. 12, 2018, now U.S. Pat. No. 10,485,771, which is a continuation of U.S. application Ser. No. 15/225,643, filed Aug. 1, 2016, now U.S. Pat. No. 10,130,593, which is a continuation of U.S. application Ser. No. 14/403,516, filed Nov. 24, 2014, now abandoned, which is the U.S. National Stage of International Application No. PCT/US2013/042457, filed May 23, 2013, which was published in English under PCT Article 21(2), which in turn claims the benefit of U.S. Provisional Patent Application Nos. 61/651,961, filed on May 25, 2012, and 61/789,629, filed on Mar. 15, 2013, each of which is hereby incorporated by reference in its entirety.

FIELD

The present disclosure relates to the field of cannabinoid receptors and, in particular, to methods of regulating cannabinoid (CB) receptor activity-related disorders and diseases, such as activating CB receptors, including treating a disorder or disease, such as a glioblastoma, hepatocellular carcinoma, liver cancer, colon cancer, and/or lung cancer, which is associated with altered cannabinoid receptor activity by administration of specific fenoterol analogues.

BACKGROUND

Cancer is the second leading cause of human death next to coronary disease in the United States. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. Cancer is soon predicted to become the leading cause of death. Many types of cancers, including brain and liver cancers, have no effective clinical treatments.

SUMMARY

This disclosure concerns the discovery that specific fenoterol analogues are cannabinoid (CB) receptor modulators and can be used to treat a disorder or disease such as a tumor, including, but not limited to, a glioblastoma or hepatocellular carcinoma that is associated with altered CB receptor activity or expression (or both), such as altered expression or activity (or both) of the GPR55 cannabinoid receptor. The inventors have discovered that administration of specific fenoterol analogues inhibits one or more signs or symptoms (such as tumor growth) associated with a tumor that expresses a CB receptor. Using this discovery, the inventors developed the disclosed methods of treating a CB receptor-modulated disorder or disease, including treatment of a tumor expressing a CB receptor; for example, a glioblastoma or hepatocellular carcinoma expressing a CB receptor.

In some embodiments, the method includes administering to a subject having or at risk of developing a disorder or disease regulated by CB receptor activity an effective amount of a compound to reduce one or more symptoms associated with the disorder or disease regulated by CB receptor activity, wherein the compound has the formula

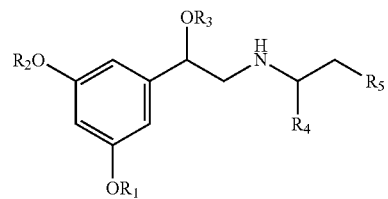

wherein $R_1$-$R_3$ independently are hydrogen, acyl, alkoxy carbonyl, amino carbonyl (carbamoyl) or a combination thereof; $R_4$ is H or lower alkyl; $R_5$ is

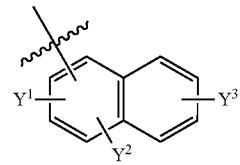

wherein $Y^1$, $Y^2$ and $Y^3$ independently are hydrogen, halogen, sulphur-containing moiety including SH, sulfoxides, sulphones, sulphanamides and related alkyl and aromatic substituted moieties, lower —$OR_6$ and —$NR_7R_8$; $R_6$ is H or lower alkyl; $R_7$ and $R_8$ independently are hydrogen, lower alkyl, alkoxy carbonyl, acyl or amino carbonyl and wherein the compound is optically active, thereby reducing the one or more symptoms associated with the disorder or disease in the subject regulated by CB receptor activity.

In some embodiments, administering comprises administering a therapeutically effective amount of a compound, wherein $R_4$ within the compound is selected from methyl, ethyl, n-propyl, and isopropyl.

In some embodiments, administering comprises administering a therapeutically effective amount of a compound, wherein $R_4$ within the compound is methyl.

In some embodiments, administering comprises administering a therapeutically effective amount of a compound, wherein $R_6$ within the compound is methyl.

In some embodiments, administering comprises administering a therapeutically effective amount of a compound, wherein $R_5$ within the compound is one of

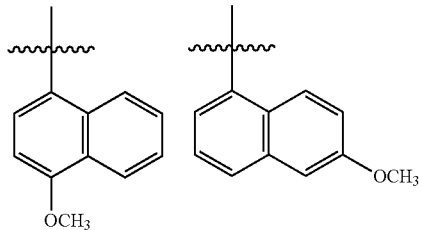

-continued

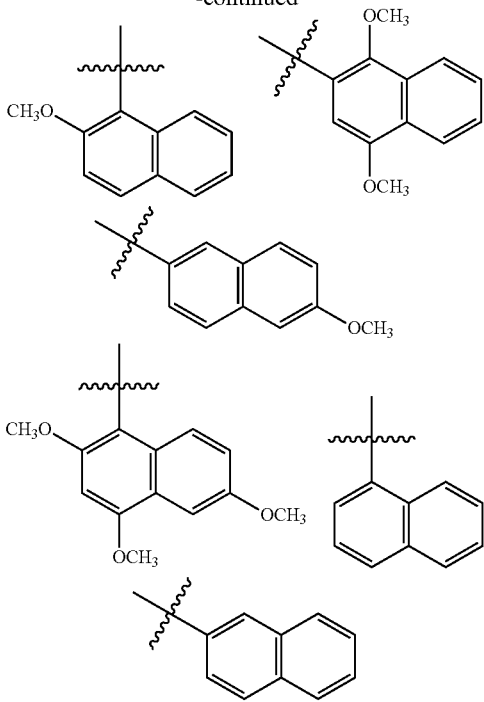

In some embodiments, administering comprises administering a therapeutically effective amount of a compound, wherein $R_1$-$R_3$ within the compound are hydrogen.

In some embodiments, administering comprises administering a therapeutically effective amount of (R,R')-4'-methoxy-1-naphthylfenoterol (MNF), (R,S')-MNF, (R,R')-ethylMNF, (R,R')-naphthylfenoterol (NF), (R,R')-ethylNF, (R,S')-NF and (R,R')-4'-amino-1-naphthylfenoterol (aminoNF), (R,R')-4'-hydroxy-1-naphthylfenoterol (hydroxyNF), or a combination thereof.

In some embodiments, administering comprises administering a therapeutically effective amount of MNF, NF or a combination thereof.

In some embodiments, administering comprises administering a therapeutically effective amount of MNF.

In some embodiments, the method includes administering a therapeutically effective amount of a pharmaceutical composition containing any of the disclosed fenoterol analogues capable of regulating a CB receptor-associated disorder or disease and a pharmaceutically acceptable carrier to treat the disorder or disease regulated by a CB receptor, such as a glioblastoma or hepatocellular carcinoma expressing GPR55. For example, the disclosed (R,R')-MNF, (R,S')-MNF, (R,R')-ethylMNF, (R,R')-NF, (R,R')-ethylNF, (R,S')-NF and (R,R')-aminoNF, (R,R')-hydroxyNF, or a combination thereof are effective at treating a glioblastoma or hepatocellular carcinoma expressing a CB receptor, such as a GPR55 expressing glioblastoma or hepatocellular carcinoma. In some embodiments, the method further includes selecting a subject having or at risk of developing a disorder or disease regulated by a CB receptor. For example, a subject is selected for treatment by determining that the disorder or tumor is associated with CB receptor expression, such as GPR55 expression. In one particular example, the method further includes selecting a subject with a disorder and/or disease, which is not associated with altered β2-AR function. For example, the disorder or disease does not respond to a treatment targeting β2-AR activity. In further examples, the method includes administering one or more therapeutic agents in addition to the fenoterol analogue or combination thereof. The methods can include administration of the one or more therapeutic agents separately, sequentially or concurrently, for example in a combined composition with a fenoterol analogue or combinations thereof.

In some embodiments, the method is for use in treating a tumor expressing a CB-receptor. For example, the disorder or disease is selected from the group consisting of a primary brain tumor expressing a CB-receptor, a glioblastoma expressing a CB-receptor, a hepatocellular carcinoma expressing a CB-receptor, colon cancer, liver cancer, and lung cancer.

In some embodiments, inhibiting one or more signs or symptoms associated with the disease or disorder comprises inhibiting cellular growth, such as tumor and/or cancer cell growth, tumor volume or a combination thereof.

In some embodiments, the method is used to treat a disorder or disease regulated by a CB receptor, which is GPR55, such as diabetes.

The foregoing and other features and advantages of the disclosure will become more apparent from the following detailed description, which proceeds with reference to the accompanying figures.

BRIEF DESCRIPTION OF THE DRAWINGS

FIGS. 1A-1C illustrate responses of HepG2 cells exposed to β-agonist stimulation. FIG. 1A is a digital image of soluble extracts which were prepared from HepG2 (lane 1) and 1321N1 (lane 2) cells maintained in complete medium, and subjected to Western blot analysis. Cellular content in β2-adrenergic receptor (β2-AR) and β-actin was measured using specific primary antibodies. FIG. 1B is a bar graph illustrating increases in cAMP accumulation in HepG2 cells with forskolin, but not with (R)-isoproterenol (Iso) or (R,R')-fenoterol (Fen). Data shown are from a single study conducted in quadruplicate. Error bars indicate mean±S.D. from a single study. FIG. 1C is a digital image of an immunoblot. Serum-starved HepG2 cells were incubated in the presence of (R)-isoproterenol (Iso; 1 µM) or (R,R')-Fen (1 µM) for 5, 10 and 30 minutes. Cell lysates were immunoblotted with antibodies against phosphorylated (Ser473) and total Akt, as well as phosphorylated ERK1/2 and total ERK2. The studies shown in FIGS. 1B and 1C were repeated twice with comparable results. The migration of molecular mass markers (values in kilodaltons) is shown on the left of immunoblots.

FIG. 2D illustrates the findings when HepG2 and 1321N1 cells were incubated without (SFM) or with serum (CM) in the presence of the indicated concentrations of Iso or (R,R')-Fen (fen). Quantification of percent change in [$^3$H]-thymidine incorporation versus control are expressed as means±SE and represent results from two to six independent studies, each performed in triplicate dishes. In most instances, error bars are smaller than the symbols.

FIGS. 3A-3D demonstrate that a β2-AR antagonist does not inhibit the anti-proliferative action of (R,R')-MNF in HepG2 cells. Serum-depleted HepG2 cells were incubated with the indicated concentrations of the β2-AR antagonist, ICI-118,551 (ICI), for 1 hour followed by the addition of vehicle (FIG. 3A), (R,R')-Fen (FIG. 3B, left panel), or (R,R')-MNF (FIG. 3B, right panel) for 24 hours, and levels of [$^3$H]-thymidine incorporation were measured. Representative dose-response curves for (R,R')-Fen and (R,R')-MNF are shown FIG. 3B. FIGS. 3C and 3D are bar graphs illustrating quantification of percent change in [$^3$H]-thymidine incorporation versus control expressed as means±SE and represent results from three independent studies, each performed in triplicate.

FIG. 6A, Total RNA was extracted from HepG2, 1321N1 and U87MG cells, and then analyzed semi-quantitatively by PCR. A non-template control (NTC) has been included (lane 1). FIGS. 6B and 6C, Serum-depleted HepG2 cells were incubated with the cannabinoid receptor agonist, WIN 55,212-2 (Win; 1 μM), (FIG. 6B) or the cannabinoid receptor antagonists, AM251 (1-(2,4-dichlorophenyl)-5-(4-iodophenyl)-4-methyl-N-1-piperidinyl-1H-pyrazole-3-carboxamide; 1 μM) or AM630 (6-iodo-2-methyl-1-[2-(4-morpholinyl)ethyl]-1H-indol-3-yl](4-methoxyphenyl)methanone, 0.5 μM), (FIG. 6C) for 1 hour followed by the addition of vehicle, (R,R')-Fen (0.5 μM), or (R,R')-MNF (0.25 μM) for 24 hours. Quantification of percent change in [$^3$H]-thymidine incorporation versus control are expressed as means±SD and represent results from three independent studies, each performed in triplicate dishes.

FIGS. 8A-8D are bar graphs illustrating cannabinoid receptors play no role in cell proliferation control by (R,R')-Fen. 1321N1 (FIG. 8A) and U87MG (FIG. 8C) cells were incubated with the cannabinoid receptor agonist, WIN 55,212-2 (Win; 0.5-1 μM) or the cannabinoid receptor antagonists, AM251 (0.5-1 μM) or AM630 (0.25-0.5 μM) (FIGS. 8B, 8D) for 1 hour followed by the addition of vehicle, (R,R')-Fen (0.5 μM), or (R,R')-MNF (0.25 μM) for 24 hours. Quantification of percent change in [$^3$H]-thymidine incorporation versus control is expressed as means±SD and represents the results from three independent studies, each performed in triplicate.

FIG. 12 illustrates the analysis of a plasma sample obtained 30 minutes post IV administration of 10 mg/kg MNF. MNF and Gluc-MNF, in the insert of FIG. 12, are shown with no interfering peaks being present in the control plasma matrix. FIG. 13 illustrates the analysis of brain tissue obtained 30 minutes post IV administration of 10 mg/kg MNF. The peak at 6.39 minutes is an unidentified compound present in control brain matrix (see insert of FIG. 13).

FIG. 18A, Cell proliferation assay was performed in rat C6 glioma cells treated with increasing concentrations of MNF for 24 hours followed by the addition of [$^3$H]-thymidine for 16 hours. FIG. 18B, Cells were preincubated without or with the selective β2-AR blocker, ICI-118,551 (3 nM) for 30 minutes followed by the addition of vehicle or 20 nM of MNF, (R,R')-Fen or isoproterenol (ISO) for 24 hours. FIG. 18C, C6 glioma cells were pretreated in the presence or absence of cannabinoid receptor inverse agonists, AM251 (0.5 and 1 µM) and AM630 (0.5 µM), for 30 minutes followed by the addition of vehicle or 20 nM MNF for 24 hours. FIGS. 18B and 18C, [$^3$H]-thymidine was determined after a 16 hour-incubation. Bars represent the average±SD of a single experiment performed in triplicate wells. Similar results were obtained in 2-3 independent experiments.

FIG. 19A, Tumor volume over time is shown for MNF-treated animals compared with vehicle-treated, tumor-bearing mice (means±SEM; n=9-10). FIG. 19B, The individual results from two cohorts of animals are depicted as area under the plasma drug concentration-time curve (AUCs). The average AUC±SEM for the vehicle group was 5450±518 (n=17) and MNF: 3217±265 (n=19). The P value presented is for a two-tailed test.

FIGS. 20A-20D illustrate gene expression profiling in MNF-treated C6 tumor-bearing mice. FIG. 20A, Gene clustering in the rat C6 xenografts: Principal component analysis (PCA) of rat C6 glioma xenograft treated with MNF vs. vehicle control. PCA was applied to the six independent samples (3 MNF, 3 controls), and numbers refer to individual sample labels. Analysis reveals clustering of samples into treatment groups. FIG. 20B, Cluster analysis of 100 gene sets altered by MNF treatment, as compared to the control group, in cohort #1, cohort #2, and combined cohorts (1+2). FIG. 20C, Zratios of selected genes of interest is depicted, showing either up- or down-regulated expression after pairwise comparison between MNF and the vehicle-treated group. FIG. 20D, Total RNA from C6 xenograft tumors from MNF- and vehicle-treated mice was extracted and analyzed for Sox4, Olig1, Galnt3, Cdkn3, Ccna2 and Bub1b mRNA levels by quantitative real-time PCR (mean±SD; n=5-6). Values were normalized to GAPDH.

FIG. 21A, Serum-depleted HepG2 cells were incubated in the presence of increasing concentrations of T1117 (2.5-100 nM). Plots of signal intensity versus time were generated from defined regions of interest (ROIs). Results are from 2-3 independent studies. FIG. 21B, Relative AUC data versus T1117 concentrations is shown, and the T1117-100 nM values were set at 1. FIG. 21C, The cellular incorporation of T1117 (100 nM) was carried out in the presence of a 100× molar excess of unlabeled AM251. Error bars indicate mean±S.D. (n=3 ROIs) from a single study, which was repeated twice with comparable results. FIG. 21D, Representative images at t=15 minutes are shown. Bar, 30 µm.

FIG. 22A, HepG2 cells were transfected with siRNA oligos either against $CB_1R$, $CB_2R$ or GPR55 or the non-silencing siRNA control for 48 hours. Cells were maintained in serum-free medium for 3 hours, followed by the addition of T1117. Plots of signal intensity vs. time were generated from defined ROIs. Error bars indicate mean±S.D. of two independent studies, each performed with 3-4 ROIs. FIG. 22B, Relative AUC data, and the control siRNA values were set at 1. FIG. 22C, Serum-depleted HepG2 cells were treated with vehicle (0.01% DMSO), AM630 (1 µM), or WIN 55,212-2 (1 µM) for 1 hour followed by the addition of T1117. Error bars indicate mean±S.D. (n=3 ROIs) from a single study, which was repeated twice with comparable results. FIG. 22D, Serum-depleted HepG2 cells were treated with vehicle (0.01% DMSO), CP 55,940 (0.25 µM), or O-1602 ([5-methyl-4-[1R,6R)-3-methyl-6-(1-methylethenyl)-2-cyclohexen-1-yl]-1,3-benzenediol; 0.25 µM) for 30 minutes followed by the addition of 10 nM T1117. Error bars indicate mean±S.D. (n=3 ROIs) from a single study, which was repeated twice with comparable results.

FIGS. 23A-25D illustrate the effect of MNF on cellular uptake of T1117. Serum-depleted HepG2 (FIG. 23A, FIG. 23B) and PANC-1 (FIG. 18C, FIG. 23D) cells were pretreated or not with MNF (1 µM) or AM251 (10 µM) for 30 minutes followed by the addition of vehicle (0.1% DMSO), AM251 or MNF for an additional 30 minutes. Cells were then incubated with 10 nM T1117. FIG. 23A, C: Plots of signal intensity vs. time were generated from defined ROIs. Error bars indicate mean±S.D. of two independent studies, each performed with 3-4 ROIs.

FIGS. 25A-25D illustrates impairment in GPR55 downstream signaling by MNF. Serum-depleted HepG2 (FIG. 25A, FIG. 25B) and PANC-1 (FIG. 25C, FIG. 25D) cells were pretreated or not in the presence of MNF (1 µM) for 10 minutes followed by the addition of vehicle, O-1602 (2.5 and 10 µM), or 10% FBS for an additional 10 minutes. Cell lysates were prepared, separated by reducing SDS-PAGE gel electrophoresis and immunoblotted for total and phospho-active forms of ERK. FIG. 25A, C: Representative immunoblots; FIG. 25B, D: phospho-ERK1/2 bands were normalized to total ERK2, and the O-1602-10 µM values were set at 1. Data are means of two independent dishes±range. The migration of molecular-mass markers (values in kilodaltons) is shown on the left of immunoblots.

FIG. 26C, Cell lysates were prepared from similar studies and immunoblotted for EGFR. The membranes were reprobed for Hsp90, which served as a loading control.

FIGS. 27A-27D show MNF inhibits ligand-induced motility of HepG2 and PANC-1 cells in a wound-healing assay. Confluent HepG2 (FIG. 27A, FIG. 27B) and PANC-1 (FIG. 27C, FIG. 27D) cells were subjected to scratch wound. Cells were incubated in the presence of DMSO (0.1%) or the GPR55 agonist AM251 (1 µM) for 30 minutes, followed by the addition of MNF (1 µM) where indicated. Images were captured at various time-points. FIGS. 27A, C: The relative wound surface area was measured over time and plotted, and values at time 0 were set at 1. FIGS. 27B, D: The relative wound surface area of four independent observations at the 24-hour time point is plotted. *, *** $P<0.05$ and 0.001.

FIG. 29C, Confluent HepG2 and PANC-1 cells were subjected to scratch wound. Cells were incubated in the presence of the atypical cannabinoid O-1602 (1 µM) for 30 minutes, followed by the addition of vehicle (DMSO, 0.1%) or MNF (1 µM). Images were captured at various time-points. The relative wound surface area at the 24-hour time point is plotted. ** $P<0.01$.

SEQUENCE LISTING

Figure 2A:
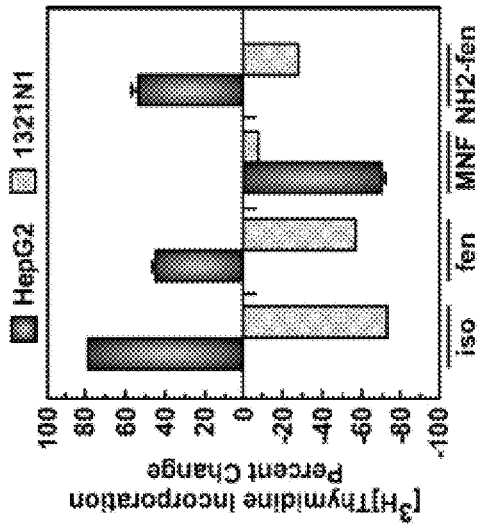
FIGS. 2A-D illustrate the effects of (R)-isoproterenol, (R,R')-Fen and derivatives on cell growth are cell-type specific. Serum-starved HepG2 cells were incubated with vehicle or the indicated concentrations of (R)-isoproterenol (Iso), (R,R')-Fen, (R,R')-aminoFen (NH$_2$-fen) or (R,R')-MNF for 24 hours, and levels of [$^3$H]-thymidine incorporation was measured. Representative dose-response curves are shown in FIGS. 2A and 2B. HepG2 cells in serum-depleted medium and 1321N1 cells in complete medium were treated with compounds at 1 µM for 24 hours and those results are shown in FIG. 2C.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Aug. 13, 2020, 2.26 KB, which is incorporated by reference herein.

DETAILED DESCRIPTION OF SEVERAL EMBODIMENTS

1. Introduction

Disclosed herein is the finding that specific fenoterol analogues, such as MNF, inhibit the growth of various types of tumor cells, including glioblastoma tumor cells, hepatocellular carcinoma cells, colon cancer cells, lung cancer cells, and liver cancer cells. In particular, the inventors performed a series of studies to characterize fenoterol analogues and determine their possible therapeutic activities. MNF was observed to inhibit the growth of human-derived hepatocellular carcinoma cells (HepG2) and human-(U87MG) and rat-(C6) derived glioblastoma cells using in vitro incubation and in vivo in flank implanted C6 xenograft in nude mice. The results were unexpected as MNF is a $\beta$2-AR agonist and this class of compounds had been shown to increase cellular growth in HepG2 cells. Binding and functional studies were performed which revealed that MNF acts as an inhibitor of the GPR55 cannabinoid receptor and, as such, represents one of the first potential drugs directed at this target. Initial pK studies demonstrated that the compound crosses the blood brain barrier and initial toxicity studies indicated that the drug had little off-target effects. The $\beta$2-AR agonist properties were a positive indication and suggest that MNF may have cardio-protective effects. MNF was also found to be capable of significantly inhibiting additional types of tumor cell growth, including, but not limited to, colon cancer cells, lung cancer cells and liver cancer cells. Further, additional fenoterol compounds, such as (R,R')-1-naphthylfenoterol (NF), were found to inhibit hepatocellular carcinoma cell growth. Thus, the essence of the discovery is the identification of a new class of compounds that can be used to treat CB receptor related disorders and diseases, and in particular GRP55-related disorders and diseases, including brain and liver cancers for which there are no current effective treatments. Based upon these findings, disclosed are methods of regulating CB receptor activity and treating disorders and diseases modulated by CB receptor activity or expression (or both), such as GRP55 activity or expression (or both).

II. Abbreviations and Terms

Abbreviations

AKAP: A-kinase anchoring protein
AM251: 1-(2,4-dichlorophenyl)-5-(4-iodophenyl)-4-methyl-N-(1-piperidyl)pyrazole-3-carboxamide
AM630: 1-[2-(morpholin-4-yl)ethyl]-2-methyl-3-(4-methoxybenzoyl)-6-iodoindole
AR: adrenergic receptor
BBB: blood brain barrier
$\beta_2$-AR: β2-adrenergic receptor
CB: cannabinoid
ERK: extracellular regulated kinase
Fen: fenoterol
GPR55: G protein-coupled receptor 55
GPCR: G protein-coupled receptor
HPLC: high performance liquid chromatography
IAM-PC: immobilized artificial membrane chromatographic support
ICI 118,551: 3-(isopropylamino)-1-[(7-methyl-4-indanyl)oxy]butan-2-ol
ICYP: [$^{125}$I]cyanopindolol
IP: intraperitoneal
IV: intravenous
MNF: 4-methoxy-1-naphthylfenoterol
NF: naphthylfenoterol
OGTT: oral glucose tolerance test
UV: ultraviolet Terms Unless otherwise explained, all technical and scientific terms used herein have the same meaning as commonly understood by one of ordinary skill in the art to which the disclosed subject matter belongs. Definitions of common terms in chemistry may be found in *The McGraw-Hill Dictionary of Chemical Terms*, 1985, and *The Condensed Chemical Dictionary*, 1981.

Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description. Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

In order to facilitate review of the various embodiments disclosed herein, the following explanations of specific terms are provided:

Acyl: A group of the formula RC(O)— wherein R is an organic group.

Acyloxy: A group having the structure —OC(O)R, where R may be an optionally substituted alkyl or optionally substituted aryl. "Lower acyloxy" groups are those where R contains from 1 to 10 (such as from 1 to 6) carbon atoms.

Administration: To provide or give a subject a composition, such as a pharmaceutical composition including one or more fenoterol analogues by any effective route. Exemplary routes of administration include, but are not limited to, injection (such as subcutaneous, intramuscular, intradermal, intraperitoneal (IP), and intravenous (IV)), oral, sublingual, rectal, transdermal, intranasal, vaginal and inhalation routes.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl.

Alkoxy carbonyl: A group of the formula —C(O)OR, where R may be an optionally substituted alkyl or optionally substituted aryl. "Lower alkoxy carbonyl" groups are those where R contains from 1 to 10 (such as from 1 to 6) carbon atoms.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to ten carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amino groups, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Amino carbonyl (carbamoyl): A group of the formula C(O)N(R)R', wherein R and R' are independently of each other hydrogen or a lower alkyl group.

Anti-diabetic agent: A chemical or pharmaceutical antihyperglycemic agent or drug capable of treating diabetes, including, but not limited to agents for alleviating the symptoms associated with type 2 diabetes or slowing the progression or onset of type 2 diabetes. Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. The anti-diabetic agents include those agents disclosed in *Diabetes Care,* 22(4):623-634 (1999), herein incorporated by reference. One common class of anti-diabetic agents is the sulfonylureas, which are believed to increase secretion of insulin, decrease hepatic gluconeogenesis, and increase insulin receptor sensitivity. Another class of anti-diabetic agents is the biguanide antihyperglycemics, which decrease hepatic glucose production and intestinal absorption, and increase peripheral glucose uptake and utilization, without inducing hyperinsulinemia. In some examples, an anti-diabetic agent is a disclosed fenoterol analogue capable of modulating a CB receptor activity, such as GPR55 activity.

Astrocytoma: A tumor of the brain that originates in astrocytes. An astrocytoma is an example of a primary tumor. Astrocytomas are the most common glioma, and can occur in most parts of the brain and occasionally in the spinal cord. However, astrocytomas are most commonly found in the cerebrum. In one example, an astrocytoma is inhibited by administering to a subject a therapeutic effective amount of fenoterol, a fenoterol analogue or a combination thereof, thereby inhibiting astrocytoma growth.

$\beta_2$-adrenergic receptor ($\beta$2-AR): A subtype of adrenergic receptors that are members of the G-protein coupled receptor family. $\beta$2-AR subtype is involved in respiratory diseases, cardiovascular diseases, premature labor and, as disclosed herein, tumor development. Increased expression of $\beta$2-ARs can serve as therapeutic targets. Currently, a number of drugs e.g., albuterol, fenoterol, formoterol, isoproterenol, or salmeterol have $\beta$2-AR agonist activities. As disclosed herein, fenoterol and fenoterol analogues are $\beta$2-AR agonists.

Blood-brain barrier (BBB): The barrier formed by epithelial cells in the capillaries that supply the brain and central nervous system. This barrier selectively allows entry of substances such as water, oxygen, carbon dioxide, and nonionic solutes such as glucose, alcohol, and general anesthetics, while blocking entry of other substances. Some small molecules, such as amino acids, are taken across the barrier by specific transport mechanisms. In one example, fenoterol or disclosed fenoterol analogues are capable of passing through the barrier.

Body Mass Index (BMI): A mathematical formula for measuring body mass in humans, also sometimes called Quetelet's Index. BMI is calculated by dividing weight (in kg) by height (in meters). The current standards for both men and women accepted as "normal" are a BMI of 20-24.9 kg/m$^2$. In one embodiment, a BMI of greater than 25 kg/m$^2$ can be used to identify an obese subject. Grade I obesity corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J*

*Clin. Nutr.,* 45: 1035-47, 1987). Ideal body weight will vary among individuals based on height, body build, bone structure, and sex.

Cannabinoid Receptors: A class of cell membrane receptors under the G protein-coupled receptor superfamily. The cannabinoid receptors contain seven transmembrane spanning domains. Cannabinoid receptors are activated by three major groups of ligands, endocannabinoids (produced by the mammalian body), plant cannabinoids (such as THC, produced by the cannabis plant) and synthetic cannabinoids (such as HU-210). All of the endocannabinoids and plant cannabinoids are lipophilic, i.e. fat soluble, compounds. Two subtypes of cannabinoid receptors are $CB_1$ (see GenBank Accession No. NM_033181 mRNA and UniProt P21554, each of which is hereby incorporated by reference as of May 23, 2012) and $CB_2$ (see GenBank Accession No. NM_001841 mRNA and UniProt P34972, each of which is hereby incorporated by reference as of May 23, 2012). The $CB_1$ receptor is expressed mainly in the brain (central nervous system, CNS), but also in the lungs, liver and kidneys. The $CB_2$ receptor is expressed mainly in the immune system and in hematopoietic cells. Additional non-$CB_1$ and non-$CB_2$ include GPR55 (GenBank Accession No. NM_005683.3 or NP_005674.2 protein, each of which is hereby incorporated by reference as of May 23, 2012), GPR119 (GenBank Accession No. NM_178471.2 or NP_848566.1 protein, each of which is hereby incorporated by reference as of May 23, 2012) and GPR18 (also known as N-arachidonyl glycine receptor and involved in microglial migration, GenBank Accession No. NM_001098200 mRNA, NP_001091670.1, each of which is hereby incorporated by reference as of May 23, 2012).

The protein sequences of $CB_1$ and $CB_2$ receptors are about 44% similar. When only the transmembrane regions of the receptors are considered, amino acid similarity between the two receptor subtypes is approximately 68%. In addition, minor variations in each receptor have been identified. Cannabinoids bind reversibly and stereo-selectively to the cannabinoid receptors. The affinity of an individual cannabinoid to each receptor determines the effect of that cannabinoid. Cannabinoids that bind more selectively to certain receptors are more desirable for medical usage. GPR55 is coupled to the G-protein $G_{13}$ and/or $G_{11}$ and activation of the receptor leads to stimulation of rhoA, cdc42 and rac1. GPR55 is activated by the plant cannabinoids $\Delta^9$-THC and cannabidiol, and the endocannabinoids anandamide, 2-AG, noladin ether in the low nanomolar range. In contrast, $CB_1$ and $CB_2$ receptors are coupled to inhibitory G proteins. This indicates that both types of receptors will have different readouts. For example, activation of $CB_1$ causes apoptosis whereas increase in GPR55 activity is oncogenic. The $CB_1$ receptor antagonist (also termed 'inverse agonist') compound, AM251, is, in fact, an agonist for GPR55. It binds GPR55 and is readily internalized. This illustrates the opposite behavior of these two GPCRs. In turn, MNF is shown herein to be a $CB_1$ receptor agonist (similar to WIN55,212-2) but acts as an inhibitor of GPR55, hence the pro-apoptotic behavior of MNF in select cancer cells.

As disclosed herein, specific fenoterol analogues, such as MNF and NF, are cannabinoid receptor regulators, such as regulators of GPR55. In an example, a fenoterol analogue either alone or in combination with other agents is administered to a subject to reduce or inhibit one or more symptoms or signs associated with a disorder (such as a metabolic, inflammatory, pain or the like disorder) or disease (such as hepatocellular carcinoma, glioblastoma, liver cancer, lung cancer, colon cancer, brain cancer, diabetes, or an inflammatory disease) modulated by cannabinoid receptors (such as GPR55).

Carbamate: A group of the formula —OC(O)N(R)—, wherein R is H, or an aliphatic group, such as a lower alkyl group or an aralkyl group.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth. In one embodiment, a chemotherapeutic agent is an agent of use in treating neoplasms such as solid tumors, including a tumor associated with CB receptor activity and/or expression. In one embodiment, a chemotherapeutic agent is radioactive molecule. In some embodiments, a CB receptor regulator, such as one or more fenoterol analogues or a combination thereof is a chemotherapeutic agent. In one example, a chemotherapeutic agent is carmustine, lomustine, procarbazine, streptozocin, or a combination thereof. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Control or Reference Value: A "control" refers to a sample or standard used for comparison with a test sample. In some embodiments, the control is a sample obtained from a healthy subject or a tissue sample obtained from a patient diagnosed with a disorder or disease, such as a tumor, that did not respond to treatment with a β2-agonist. In some embodiments, the control is a historical control or standard reference value or range of values (such as a previously tested control sample, such as a group of subjects which do not have a tumor expressing CB receptors or group of samples that represent baseline or normal values, such as the level of CB receptors in tumor tissue that does not respond to treatment with fenoterol, a fenoterol analogue or a combination thereof).

Diabetes mellitus: A disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an autoimmune disease characterized by destruction of the pancreatic β cells that leads to a total or near total lack of insulin. In diabetes type 2 (sometimes referred to as "non-insulin-dependent diabetes" or "adult-onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19th ed.).

A subject exhibiting one or more of the following risk factors is considered to have a heightened or substantial risk of developing diabetes type 2:
1. Obesity, such as a BMI greater than or equal to about 30 kg/m$^2$;
2. Elevated fasting blood glucose (FPG) levels;
3. Impaired glucose tolerance (IGT);
4. Non-Caucasian ethnicity;
5. Hyperinsulinemia;
6. Hypertriglyceridemia;
7. Family history of diabetes;
8. History of gestational diabetes;
9. Sedentary lifestyle; and
10. In humans, middle age or elderly status (i.e., 40 years old and older).

A "non-diabetic" or "normal" subject does not have any form of diabetes, such as type 1 diabetes, type 2 diabetes, or pre-diabetes.

Derivative: A chemical substance that differs from another chemical substance by one or more functional groups. Preferably, a derivative (such as a fenoterol analogue) retains a biological activity (CB receptor activation) of a molecule from which it was derived (such as a fenoterol analogue capable of regulating a CB receptor, such as GPR55).

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease. In some examples, an "effective amount" is a "therapeutically effective amount" in which the agent alone with an additional therapeutic agent(s) (for example a chemotherapeutic agent) induces the desired response such as treatment of a tumor. In one example, a desired response is to decrease tumor size or metastasis in a subject to whom the therapy is administered. Tumor metastasis does not need to be completely eliminated for the composition to be effective. For example, a composition can decrease metastasis by a desired amount, for example by at least 20%, at least 50%, at least 60%, at least 70%, at least 80%, at least 90%, at least 95%, at least 98%, or even at least 100% (elimination of the tumor), as compared to metastasis in the absence of the composition.

In particular examples, it is an amount of an agent effective to decrease a number of carcinoma cells, such as in a subject to whom it is administered, for example a subject having one or more carcinomas. The cancer cells do not need to be completely eliminated for the composition to be effective. For example, a composition can decrease the number of cancer cells by a desired amount, for example by at least 20%, at least 50%, at least 60%, at least 70%, at least 80%, at least 90%, at least 95%, at least 98%, or even at least 100% (elimination of detectable cancer cells), as compared to the number of cancer cells in the absence of the composition.

In some examples, an effective amount is the amount of (R,R')- or (R,S')-fenoterol analogue(s) useful in reducing, inhibiting, and/or treating a disorder or disease associated with CB receptor, such as GPR55, expression and/or activity. Ideally, a therapeutically effective amount of an agent is an amount sufficient to reduce, inhibit, and/or treat the disorder in a subject without causing a substantial cytotoxic effect in the subject.

The effective amount of a composition useful for reducing, inhibiting, and/or treating a disorder in a subject will be dependent on the subject being treated, the severity of the disorder, and the manner of administration of the therapeutic composition. Effective amounts a therapeutic agent can be determined in many different ways, such as assaying for a reduction in tumor size or improvement of physiological condition of a subject having a tumor, such as a brain tumor. Effective amounts also can be determined through various in vitro, in vivo or in situ assays.

Glioblastoma: A common and malignant form of a primary brain tumor. A glioblastoma is a grade IV astrocytoma and usually spreads rapidly in the brain. In one example, a glioblastoma is inhibited by administering a therapeutic effective amount of a fenoterol analogue with other agents capable of regulating a CB receptor, such as GPR55, to a subject, thereby inhibiting one or more symptoms associated with the glioblastoma.

Inflammation: When damage to tissue occurs, the body's response to the damage is usually inflammation. The damage may be due to trauma, lack of blood supply, hemorrhage, autoimmune attack, transplanted exogenous tissue or infection. This generalized response by the body includes the release of many components of the immune system (for instance, IL-1 and TNF), attraction of cells to the site of the damage, swelling of tissue due to the release of fluid and other processes. In some examples, a disclosed fenoterol analogue capable of regulating CB receptor activity is used to treat, such as reduce or inhibit, one or more signs or symptoms associated with inflammation.

Isomers: Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that contain two or more chiral centers and are not mirror images of one another are termed "diastereomers." Steroisomers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers, respectively). A chiral compound can exist as either an individual enantiomer or as a mixture thereof. A mixture containing equal proportions of the enantiomers is called a "racemic mixture."

The compounds described herein may possess one or more asymmetric centers; such compounds can therefore be produced as individual (R), (S), (R,R'), (R,S')-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well known in the art (see, e.g., March, *Advanced Organic Chemistry*, 4th edition, New York: John Wiley and Sons, 1992, Chapter 4).

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):515-209S, 1998). Excess body fat is a result of an imbalance of energy intake and energy expenditure. In one embodiment in humans, the Body Mass Index (BMI) is used to assess obesity. In one embodiment, a BMI of 25.0 kg/m$^2$ to 29.9 kg/m$^2$ is overweight, while a BMI of 30 kg/m$^2$ is obese.

In another embodiment in humans, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin-dependent (type 2) diabetes, hypertension, stroke, cancer (e.g., endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Optional: "Optional" or "optionally" means that the subsequently described event or circumstance can but need not occur, and that the description includes instances where said event or circumstance occurs and instances where it does not.

Oral glucose tolerance test (OGTT): A diagnostic test for diabetes. After fasting overnight, a subject is provided a concentrated sugar solution to drink, usually containing 50 to 100 grams of glucose. The subject's blood is sampled periodically over the next few to several hours to test blood glucose levels over time. In a non-diabetic subject, blood glucose concentration shows a slight upward shift and returns to normal within 2-3 hours. In a diabetic subject, blood glucose concentration is generally higher than normal after fasting, rises more after the subject drinks the glucose solution, and may take several hours to return to normal. An OGTT of greater than or equal to 140 mg/dl and less than 200 mg/dl indicates that a subject has pre-diabetes. An OGTT of greater than or equal to 200 mg/dl indicates that a subject has frank diabetes, and an OGTT of less than 140 mg/dl indicates that a subject is normal (healthy) and does not have pre-diabetes or diabetes.

Overweight: An individual who weighs more than their ideal body weight. An overweight individual can be obese, but is not necessarily obese. In one embodiment, an overweight human individual is any individual who desires to decrease their weight. In another embodiment, an overweight human individual is an individual with a BMI of 25.0 kg/m$^2$ to 29.9 kg/m$^2$.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds or molecules, such as one or more nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phenyl: Phenyl groups may be unsubstituted or substituted with one, two or three substituents, with substituent(s) independently selected from alkyl, heteroalkyl, aliphatic, heteroaliphatic, thioalkoxy, halo, haloalkyl (such as —CF$_3$), nitro, cyano, —OR (where R is hydrogen or alkyl), —N(R) R' (where R and R' are independently of each other hydrogen or alkyl), —COOR (where R is hydrogen or alkyl) or —C(O)N(R')R" (where R' and R" are independently selected from hydrogen or alkyl).

Purified: The term "purified" does not require absolute purity; rather, it is intended as a relative term. Thus, for example, a purified preparation is one in which a desired component such as an (R,R')-enantiomer of fenoterol is more enriched than it was in a preceding environment such as in a (±)-fenoterol mixture. A desired component such as (R,R')-enantiomer of fenoterol is considered to be purified, for example, when at least about 70%, 80%, 85%, 90%, 92%, 95%, 97%, 98%, or 99% of a sample by weight is composed of the desired component. Purity of a compound may be determined, for example, by high performance liquid chromatography (HPLC) or other conventional methods. In an example, the specific fenoterol analogue enantiomers are purified to represent greater than 90%, often greater than 95% of the other enantiomers present in a purified preparation. In other cases, the purified preparation may be essentially homogeneous, wherein other stereoisomers are less than 1%.

Compounds described herein may be obtained in a purified form or purified by any of the means known in the art, including silica gel and/or alumina chromatography. See, e.g., *Introduction to Modern Liquid Chromatography*, 2nd Edition, ed. by Snyder and Kirkland, N.Y.: John Wiley and Sons, 1979; and *Thin Layer Chromatography*, ed. by Stahl, New York: Springer Verlag, 1969. In an example, a compound includes purified fenoterol or fenoterol analogue with a purity of at least about 70%, 80%, 85%, 90%, 92%, 95%, 97%, 98%, or 99% of a sample by weight relative to other contaminants. In a further example, a compound includes at least two purified stereoisomers each with a purity of at least about 70%, 80%, 85%, 90%, 92%, 95%, 97%, 98%, or 99% of a sample by weight relative to other contaminants. For instance, a compound can include a substantially purified (R,R')-fenoterol analogue and a substantially purified (R,S')-fenoterol analogue.

Subject: The term "subject" includes both human and veterinary subjects, for example, humans, non-human primates, dogs, cats, horses, rats, mice, and cows. Similarly, the term mammal includes both human and non-human mammals.

Tissue: A plurality of functionally related cells. A tissue can be a suspension, a semi-solid, or solid. Tissue includes cells collected from a subject such as the brain or a portion thereof.

Tumor: All neoplastic cell growth and proliferation, whether malignant or benign, and all pre-cancerous and cancerous cells and tissues. A primary tumor is tumor growing at the anatomical site where tumor progression began and proceeded to yield this mass. A primary brain tumor (also referred to as a glioma) is a tumor that originates in the brain. Exemplary primary brain tumors include astrocytomas, glioblastomas, ependymoma, oligodendroglomas, and mixed gliomas. In some examples, a primary brain tumor expresses CB receptors, such as a glioblastoma associated with CB receptor expression.

Under conditions sufficient for: A phrase that is used to describe any environment that permits the desired activity. In one example, under conditions sufficient for includes administering one or more fenoterol analogues, fenoterol or a combination thereof to a subject to at a concentration sufficient to allow the desired activity. In some examples, the desired activity is reducing or inhibiting a sign or symptom associated with a disorder or disease, such as a primary brain tumor, hepatocellular carcinoma, liver cancer, colon cancer, or lung cancer, can be evidenced, for example, by a delayed onset of clinical symptoms of the tumor in a susceptible subject, a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disease. In one particulate example, the desired activity is preventing or inhibiting tumor growth, such as astrocytoma, glioblastoma, or hepatocellular carcinoma growth. Tumor growth does not need to be completely inhibited for the treatment to be considered effective. For example, a partial reduction or slowing of growth such as at least about a 10% reduction, such as at least 20%, at least about 30%, at least about 40%, at least about 50% or greater is considered to be effective.

III. (R,R')-fenoterol and Fenoterol Analogues

A. Chemical Structure

Some exemplary fenoterol analogues disclosed herein have the formula:

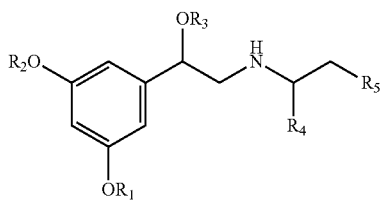

wherein $R_1$-$R_3$ independently are hydrogen, acyl, alkoxy carbonyl, amino carbonyl or a combination thereof;
$R_4$ is H or lower alkyl;
$R_5$ is lower alkyl,

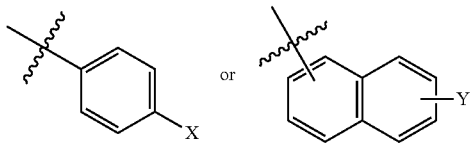

wherein X and Y independently are selected from hydrogen, lower —$OR_6$ and —$NR_7R_8$;
$R_6$ is lower alkyl or acyl; and
$R_7$ and $R_8$ independently are hydrogen, lower alkyl, alkoxy carbonyl, acyl or amino carbonyl.

With continued reference to the general formula for fenoterol analogues above, Y may be —OH.

In one embodiment, $R_5$ is a 1- or 2-naphthyl derivative optionally having 1, 2 or 3 substituents. Examples of such $R_5$ groups are represented by the formula

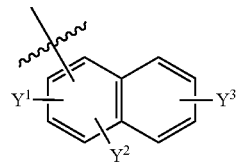

wherein $Y^1$, $Y^2$ and $Y^3$ independently are hydrogen, halogen, sulphur-containing moiety including SH, sulfoxides, sulphones, sulphanamides and related alkyl and aromatic substituted moieties, lower —$OR_6$ and —$NR_7R_8$; $R_6$ is independently for each occurrence selected from lower alkyl and acyl; and $R_7$ and $R_8$ independently are hydrogen, lower alkyl, alkoxy carbonyl, acyl or amino carbonyl (carbamoyl). In particular compounds at least one of $Y^1$, $Y^2$ and $Y^3$ is —$OCH_3$.

Particular $R_5$ groups include those represented by the formulas

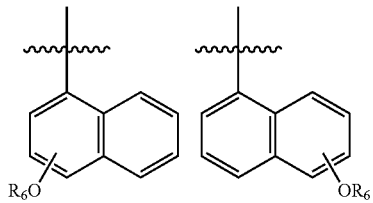

wherein $R_6$ is lower alkyl, such as methyl, ethyl, propyl or isopropyl or acyl, such as acetyl.

Exemplary $R_5$ groups include

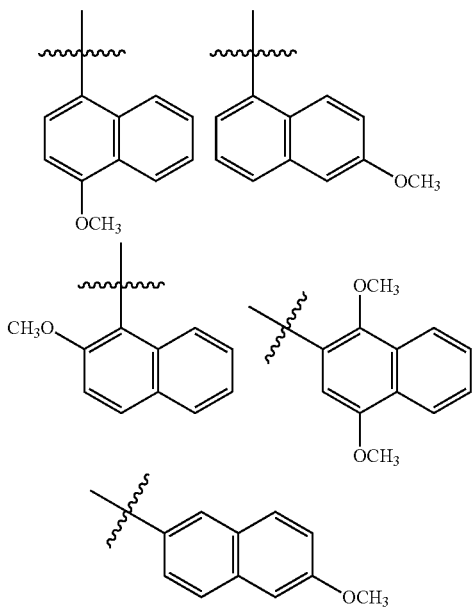

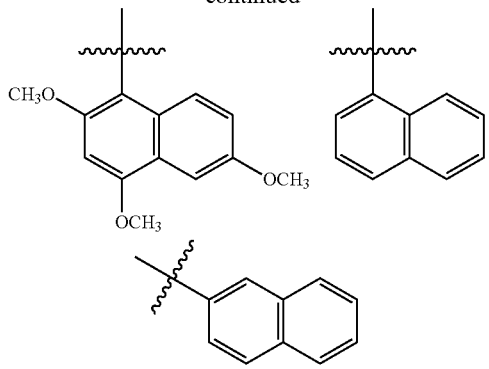

In one example, $R_4$ is lower alkyl and $R_5$ is

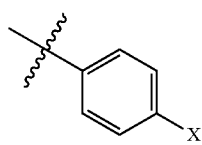

wherein X and Y independently are selected from H, lower alkyl —$OR_6$ and —$NR_7R_8$; $R_6$ is lower alkyl; and $R_7$ and $R_8$ independently are hydrogen or lower alkyl.

In a further example, $R_4$ is selected from ethyl, n-propyl, and isopropyl and $R_5$ has the formula

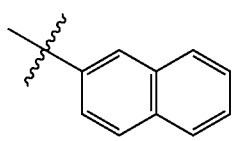

wherein X is H, —$OR_6$ or —$NR_7R_8$. For example, $R_6$ may be methyl or $R_7$ and $R_8$ are hydrogen.

In an additional example, $R_5$ has the formula

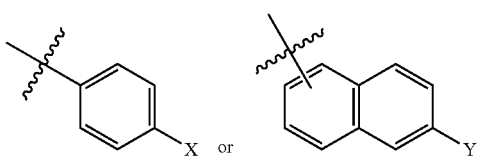

In further embodiments, $R_4$ is selected from methyl, ethyl, n-propyl and isopropyl and $R_5$ represents

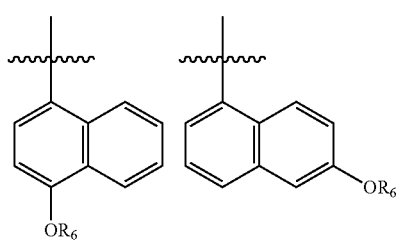

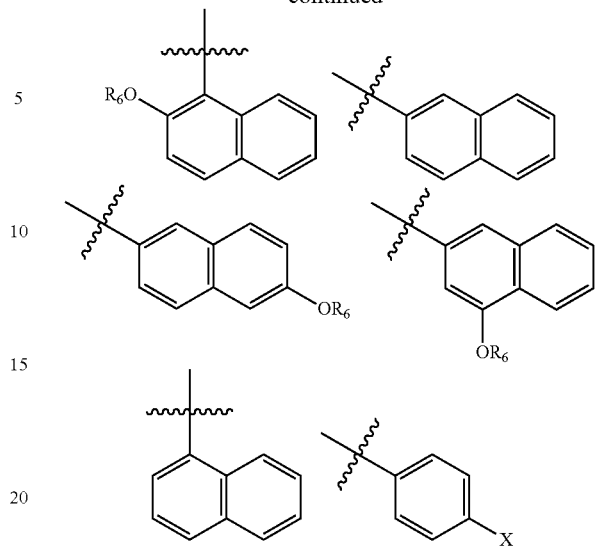

In some embodiments, $R_1$-$R_3$ independently are hydrogen; $R_4$ is a lower alkyl (such as, $CH_3$ or $CH_2CH_3$); $R_5$ is lower alkyl,

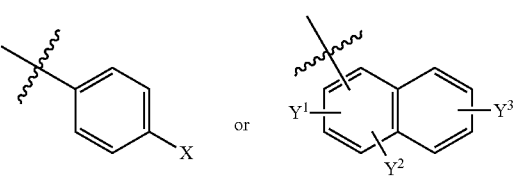

wherein X, $Y^1$, $Y^2$ and $Y^3$ independently are hydrogen, —$OR_6$ and —$NR_7R_8$; $R_6$ is independently hydrogen, lower alkyl, acyl, alkoxy carbonyl or amino carbonyl; $R_7$ and $R_8$ independently are hydrogen, lower alkyl, alkoxy carbonyl, acyl or amino carbonyl and wherein the compound is optically active.

In some embodiments, $R_1$-$R_3$ independently are hydrogen; $R_4$ is a methyl or an ethyl; $R_5$ is

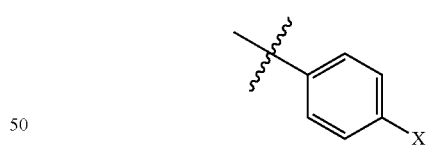

wherein X is —OH or —$OCH_3$.

In some embodiments, $R_1$-$R_3$ independently are hydrogen; $R_4$ is a methyl or an ethyl; $R_5$ is

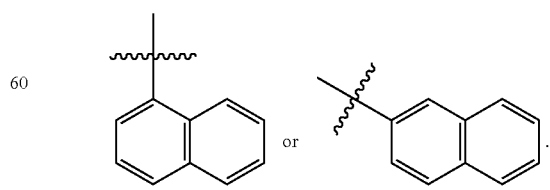

Exemplary compounds include, but are not limited to, (R,R')-4'-methoxy-1-naphthylfenoterol (MNF), (R,S')-

MNF, (R,R')-ethylMNF, (R,R')-naphthylfenoterol (NF), (R,R')-ethylNF, (R,S')-NF and (R,R')-4'-amino-1-naphthylfenoterol (aminoNF), or (R,R')-4'-hydroxy-1-naphthylfenoterol (hydroxyNF).

Examples of suitable groups for $R_1$-$R_3$ that can be cleaved in vivo to provide a hydroxy group include, without limitation, acyl, acyloxy and alkoxy carbonyl groups. Compounds having such cleavable groups are referred to as "prodrugs." The term "prodrug," as used herein, means a compound that includes a substituent that is convertible in vivo (e.g., by hydrolysis) to a hydroxyl group. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed), *Design and Application of Prodrugs, Textbook of Drug Design and Development*, Chapter 5, 113 191 (1991); Bundgaard, et al., *Journal of Drug Delivery Reviews*, 8:1 38(1992); Bundgaard, *Pharmaceutical Sciences*, 77:285 et seq. (1988); and Higuchi and Stella (eds.) *Prodrugs as Novel Drug Delivery Systems*, American Chemical Society (1975).

In some embodiments, administering comprises administering a therapeutically effective amount of MNF, NF or a combination thereof. In some embodiments, administering comprises administering a therapeutically effective amount of MNF.

In some embodiments, the method includes administering a therapeutically effective amount of a pharmaceutical composition containing any of the disclosed fenoterol analogues capable of regulating a CB receptor disorder or disease and a pharmaceutically acceptable carrier to treat the disorder or disease regulated by a CB receptor, such as a glioblastoma or hepatocellular carcinoma expressing GPR55. For example, the disclosed (R,R')-MNF, (R,S')-MNF, (R,R')-ethylMNF, (R,R')-NF, (R,R')-ethylNF, (R,S')-NF and (R,R')-aminoNF, (R,R')-hydroxyNF, or a combination thereof An exemplary (R,R')-compound has the chemical structure of:

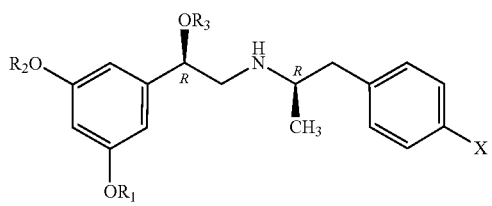

X and $R_1$-$R_3$ are as described above.

An additional exemplary (R,R')-compound has the chemical structure:

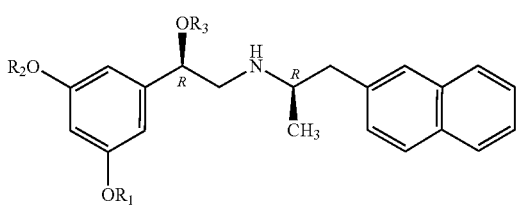

An exemplary (R,S')-compound has the chemical structure:

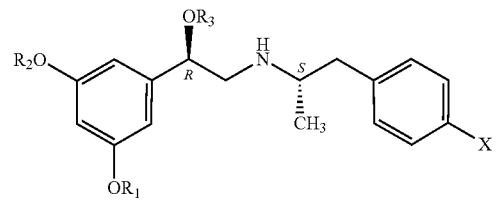

wherein X and $R_1$-$R_3$ are as described above.

An additional exemplary (R,S')-compound has the chemical structure:

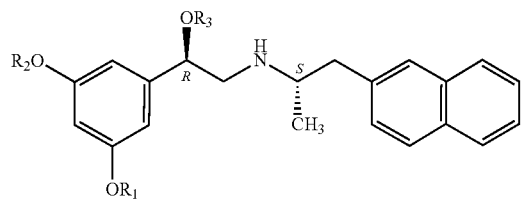

An exemplary (S,R')-compound has the chemical structure:

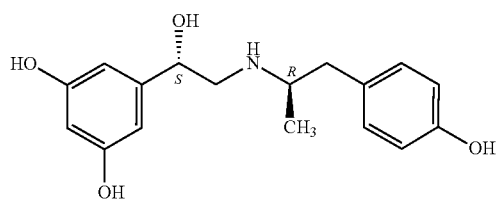

wherein X and $R_1$-$R_3$ are as described above.

An exemplary (S,S')-compound has the chemical structure:

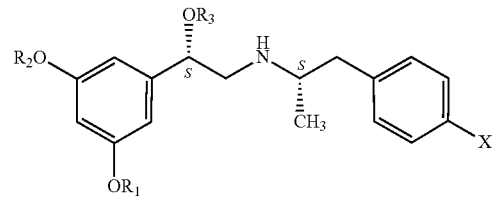

wherein X and $R_1$-$R_3$ are as described above.

Examples of chemical structures illustrating the various stereoisomers of fenoterol are provided below.

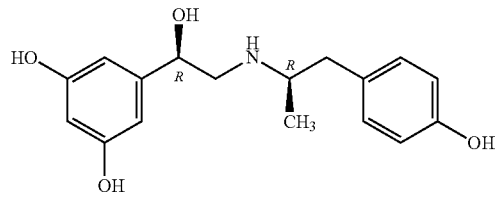

(R,R')-Fenoterol

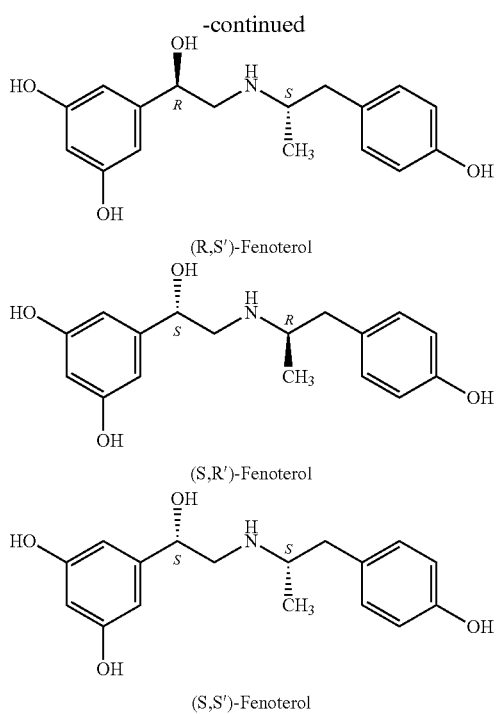

(R,S')-Fenoterol (S,R')-Fenoterol (S,S')-Fenoterol

Particular method embodiments contemplate the use of solvates (such as hydrates), pharmaceutically acceptable salts and/or different physical forms of (R,R')-fenoterol or any of the fenoterol analogues herein described.

1. Solvates, Salts and Physical Forms

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol-associated compound, methanol-associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically acceptable salts that are non-toxic. Salts may be of any type (both organic and inorganic), such as fumarates, hydrobromides, hydrochlorides, sulfates and phosphates. In an example, salts include non-metals (e.g., halogens) that form group VII in the periodic table of elements. For example, compounds may be provided as a hydrobromide salt.

Additional examples of salt-forming groups include, but are not limited to, a carboxyl group, a phosphonic acid group or a boronic acid group, that can form salts with suitable bases. These salts can include, for example, nontoxic metal cations, which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Exemplary compounds disclosed herein possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In a currently preferred embodiment, fenoterol is provided as a hydrobromide salt and exemplary fenoterol analogues are provided as their fumarate salts.

Additional counterions for forming pharmaceutically acceptable salts are found in Remington's Pharmaceutical Sciences, 19th Edition, Mack Publishing Company, Easton, Pa., 1995. In one aspect, employing a pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

2. Use for the Manufacture of a Medicament

Any of the above described compounds (e.g., (R,R') and/or (R,S') fenoterol analogues or a hydrate or pharmaceutically acceptable salt thereof) or combinations thereof are intended for use in the manufacture of a medicament for regulation of a CB receptor, such as GPR55, in a subject either at risk of developing or having a CB receptor-regulated disorder (such as a metabolic, inflammatory, pain or the like disorder) or disease (such as hepatocellular carcinoma, glioblastoma, liver cancer, lung cancer, colon cancer, brain cancer, diabetes, or an inflammatory disease) modulated by cannabinoid receptors (such as GPR55).

Formulations suitable for such medicaments, subjects who may benefit from same and other related features are described elsewhere herein.

B. Methods of Synthesis

The disclosed fenoterol analogues can be synthesized by any method known in the art including those described in U.S. patent application Ser. No. 12/376,945 filed Feb. 9, 2009, U.S. patent application Ser. No. 13/333,866 filed Dec. 21, 2011 and WO 2011/112867 filed Mar. 10, 2011, each of which is hereby incorporated by reference in its entirety. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via open column chromatography or prep chromatography.

Suitable exemplary syntheses of fenoterol analogues are provided below:

Scheme I: An exemplary synthesis of 4 stereoisomers of 1-6 including the coupling of the epoxide formed from either (R)- or (S)-3',5'-dibenzyloxyphenylbromohydrin with the (R)- or (S)-enantiomer of the appropriate benzyl-protected 2-amino-3-benzylpropane (1-5) or the (R) or (S)-enantiomer of N-benzyl-2-aminoheptane (6).

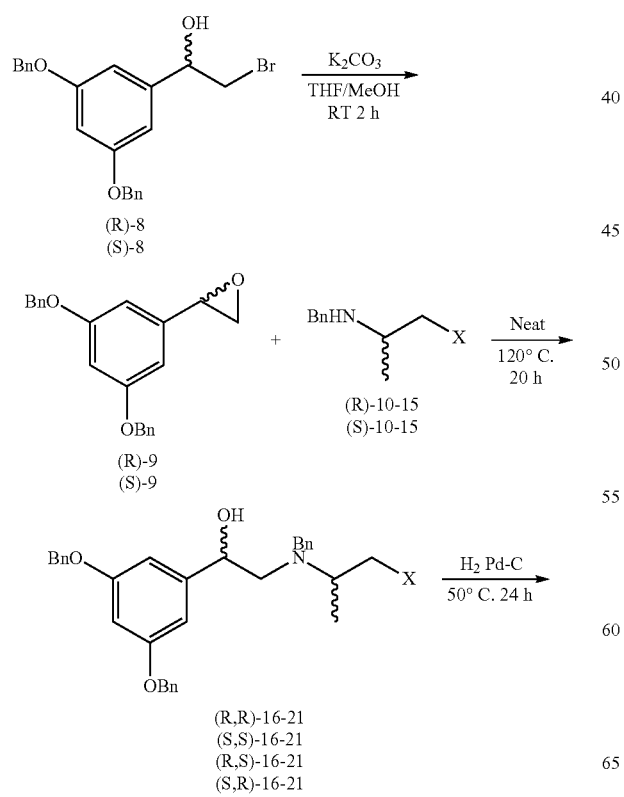

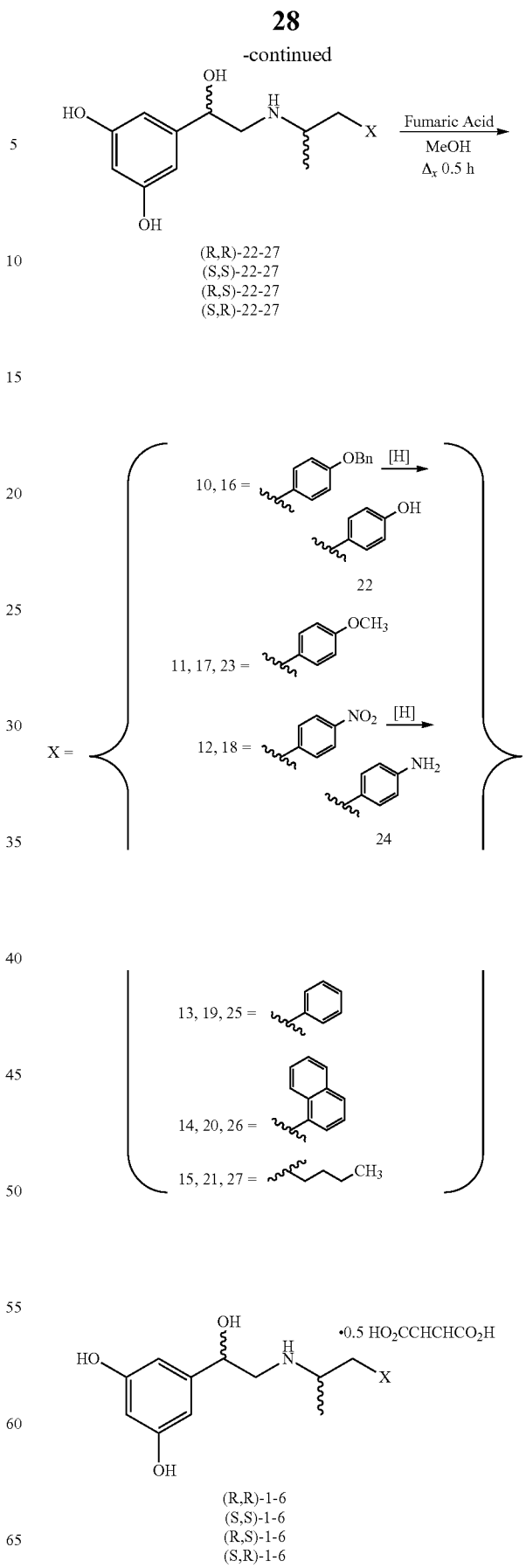

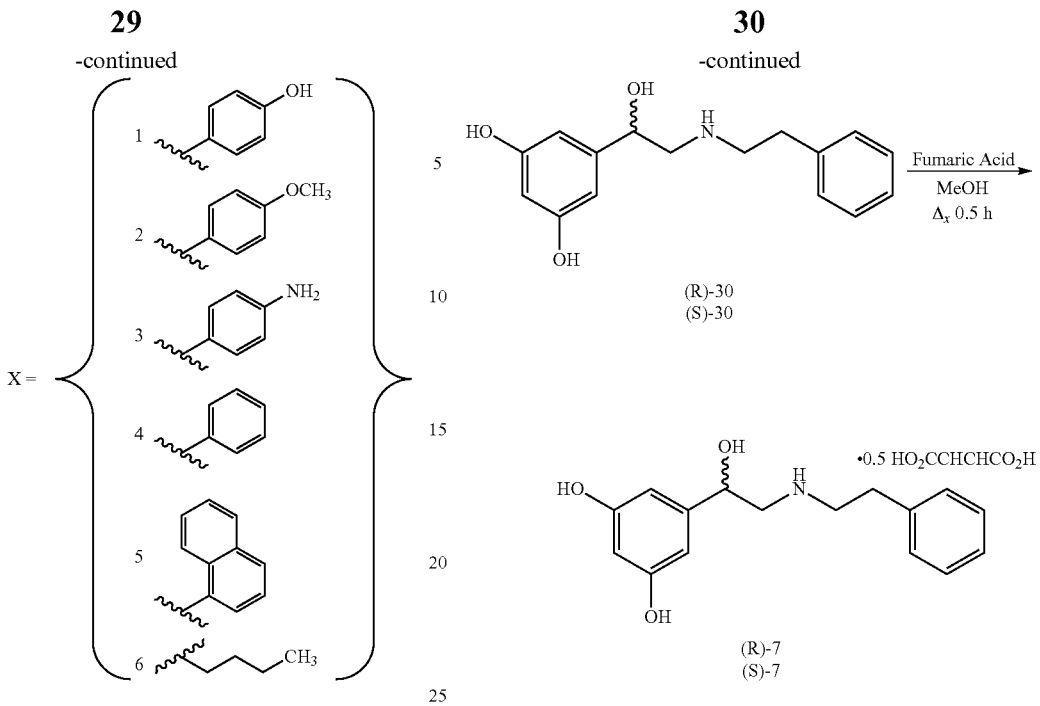

Scheme II: Exemplary synthesis of (R)-7 and (S)-7 using 2-phenethylamine. The resulting compounds may be deprotected by hydrogenation over Pd/C and purified as the fumarate salts.

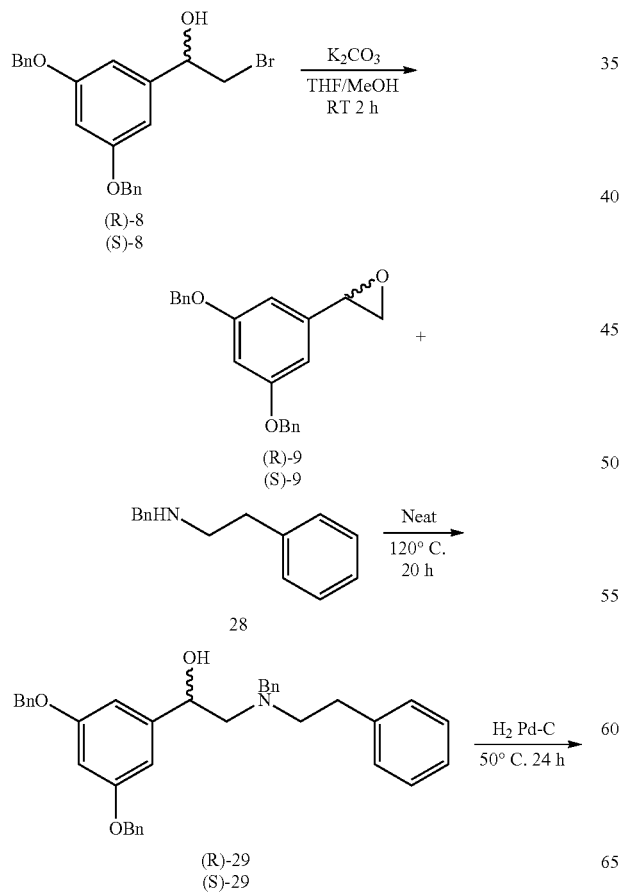

Scheme III describes an exemplary synthesis for the chiral building blocks used in Scheme II. The (R)- and (S)-3',5'-dibenzyloxyphenyl-bromohydrin enantiomers were obtained by the enantiospecific reduction of 3,5-dibenzyloxy-a-bromoacetophenone using boron-methyl sulfide complex (BH3SCH3) and either (1R,2S)- or (1S,2R)-cis-1-amino-2-indanol. The required (R)- and (S)-2-benzylaminopropanes were prepared by enantioselective crystallization of the rac-2-benzylaminopropanes using either (R)- or (S)-mandelic acid as the counter ion.

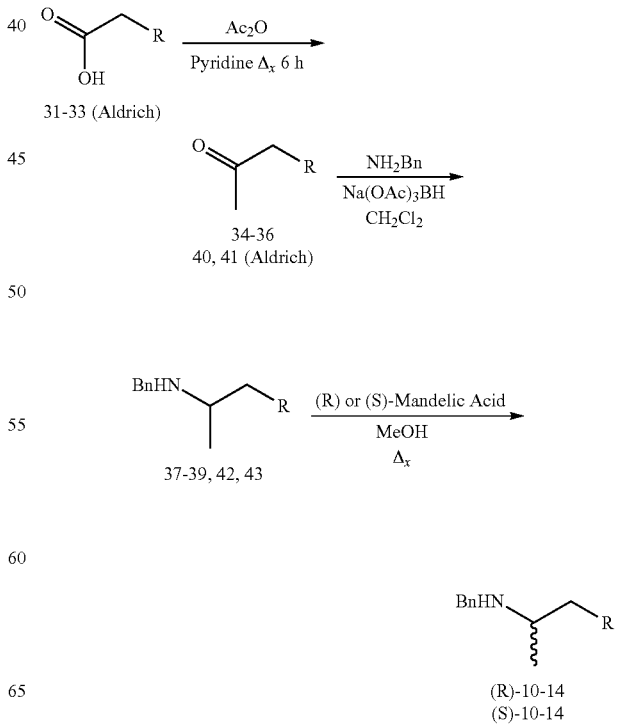

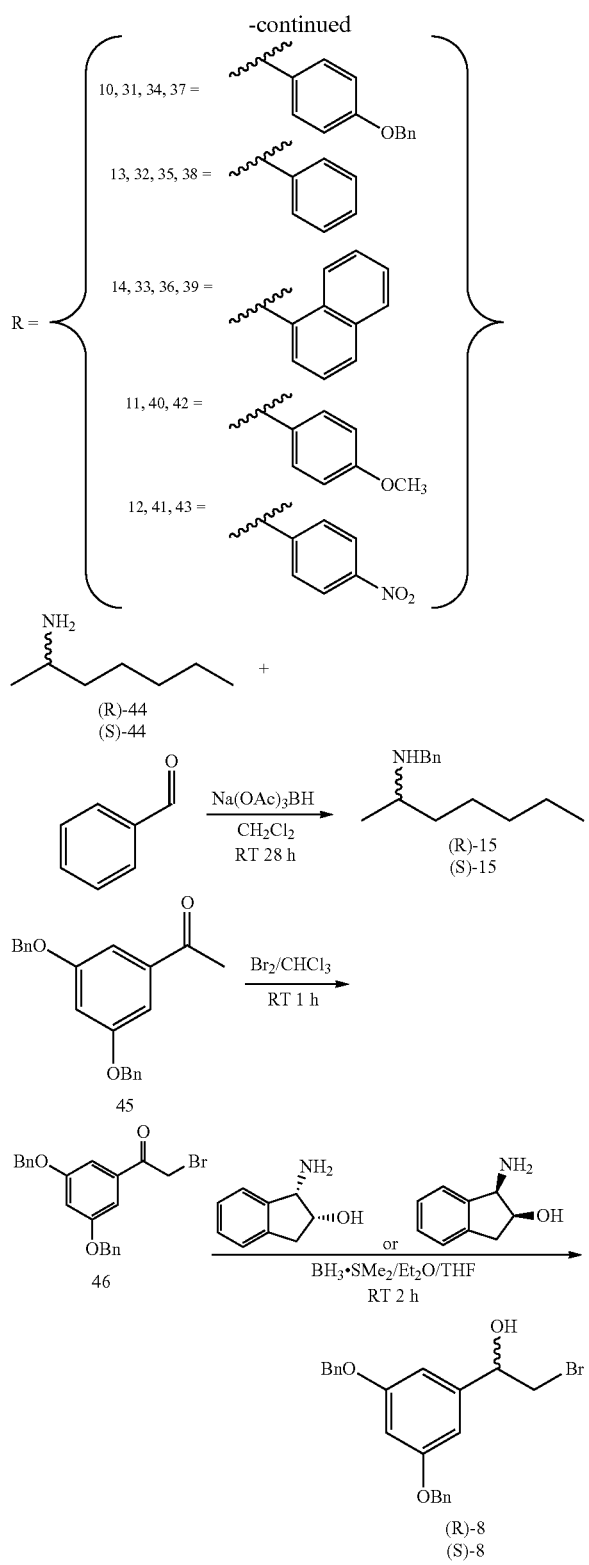

IV. Pharmaceutical Compositions

The disclosed fenoterol analogues can be useful, at least, for reducing or inhibiting one or more symptoms or signs associated with a disorder (such as a metabolic, inflammatory, pain or the like disorder) or disease (such as hepatocellular carcinoma, glioblastoma, liver cancer, lung cancer, colon cancer, brain cancer, diabetes, or an inflammatory disease) modulated by cannabinoid receptors (such as GPR55). Accordingly, pharmaceutical compositions comprising at least one disclosed fenoterol analogue are also described herein.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of (R,R')-fenoterol and disclosed fenoterol analogues. Pharmaceutical compositions comprising at least one of these compounds can be formulated for use in human or veterinary medicine. Particular formulations of a disclosed pharmaceutical composition may depend, for example, on the mode of administration (e.g., oral or parenteral) and/or on the disorder to be treated (e.g., a tumor associated with CB receptor, such as GPR55 receptor, activity or expression). In some embodiments, formulations include a pharmaceutically acceptable carrier in addition to at least one active ingredient, such as a fenoterol compound.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 19th Edition, Mack Publishing Company, Easton, Pa., 1995. A pharmaceutically acceptable salt may also serve to adjust the osmotic pressure of the composition.

The dosage form of a disclosed pharmaceutical composition will be determined by the mode of administration chosen. For example, in addition to injectable fluids, oral dosage forms may be employed. Oral formulations may be liquid such as syrups, solutions or suspensions or solid such as powders, pills, tablets, or capsules. Methods of preparing such dosage forms are known, or will be apparent, to those skilled in the art.

Certain embodiments of the pharmaceutical compositions comprising a disclosed compound may be formulated in unit dosage form suitable for individual administration of precise dosages. The amount of active ingredient such as (R,R')-MNF or NF administered will depend on the subject being treated, the severity of the disorder, and the manner of administration, and is known to those skilled in the art. Within these bounds, the formulation to be administered will contain a quantity of the extracts or compounds disclosed herein in an amount effective to achieve the desired effect in the subject being treated.

In particular examples, for oral administration the compositions are provided in the form of a tablet containing from about 1.0 to about 50 mg of the active ingredient, particularly about 2.0 mg, about 2.5 mg, 5 mg, about 10 mg, or about 50 mg of the active ingredient for the symptomatic adjustment of the dosage to the subject being treated. In one exemplary oral dosage regimen, a tablet containing from about 1 mg to about 50 mg (such as about 2 mg to about 10 mg) active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

In one embodiment, the pharmaceutical composition is administered without concurrent administration of a second agent for the treatment of a tumor that expresses a CB receptor, such as GPR55. In one specific, non-limiting example, one or more of the disclosed compositions is administered without concurrent administration of other agents, such as without concurrent administration of an additional agent also known to target the tumor. In other specific non-limiting examples, a therapeutically effective amount of a disclosed pharmaceutical composition is administered concurrently with an additional agent, including an additional therapy (such as, but not limited to, a chemotherapeutic agent, an additional CB receptor regulator (such as regulator of GPR55), an anti-inflammatory agent, an anti-oxidant, or other agents known to those of skill in the art). For example, the disclosed compounds are administered in combination with a chemotherapeutic agent, anti-oxidants, anti-inflammatory drugs or combinations thereof.

In other examples, a disclosed pharmaceutical composition is administered an adjuvant therapy. For example, a pharmaceutical composition containing one or more of the disclosed compounds is administered orally daily to a subject in order to prevent or retard tumor growth. In one particular example, a composition containing equal portions of two or more disclosed compounds is provided to a subject. In one example, a composition containing unequal portions of two or more disclosed compounds is provided to the subject. For example, a composition contains unequal portions of a (R,R')-fenoterol derivative and a (S,R')-fenoterol derivative and/or a (R,S')-derivative. In one particular example, the composition includes a greater amount of the (S,R')- or (R,S')-fenoterol derivative. Such therapy can be given to a subject for an indefinite period of time to inhibit, prevent, or reduce tumor reoccurrence.

V. Methods of Use

The present disclosure includes methods of treating disorders including reducing or inhibiting one or more signs or symptoms associated with a disorder (such as a metabolic, inflammatory, pain or the like disorder) or disease (such as hepatocellular carcinoma, glioblastoma, liver cancer, lung cancer, colon cancer, brain cancer, diabetes, or an inflammatory disease) modulated by cannabinoid receptors (such as GPR55). In some examples, methods include reducing or inhibiting one or more signs or symptoms associated with a tumor (such as hepatocellular carcinoma, glioblastoma, liver cancer, lung cancer, colon cancer, brain cancer, diabetes, or an inflammatory disease) modulated by cannabinoid receptors (such as GPR55).

In some examples, the tumor is a primary tumor, such as a primary brain tumor expressing or regulated by CB receptors, such as GPR55. In some examples, the tumor is a glioblastoma or hepatocellular carcinoma expressing CB receptors, such as GPR55. In some examples, the tumor is a glioblastoma or hepatocellular carcinoma expressing CB receptors, such as GPR55, but not expressing β2-AR. In some examples, the tumor is a glioblastoma or hepatocellular carcinoma expressing both CB receptors, such as GPR55, and β2-AR. The fenoterol analogue and/or fenoterol, such as (R,R') fenoterol, itself is administered depending upon the tumor receptor population. For example, a tumor expressing or regulated by a CB receptors, such as GPR55, is treated by administering one or more disclosed fenoterol analogues possessing CB receptor modulatory activity, such as (R,R')-4'-methoxy-1-naphthylfenoterol (MNF), (R,S')-MNF, (R,R')-ethylMNF, (R,R')-naphthylfenoterol (NF), (R,R')-ethylNF, (R,S')-NF and (R,R')-4'-amino-1-naphthylfenoterol (aminoNF), (R,R')-4'-hydroxy-1-naphthylfenoterol (hydroxyNF), or a combination thereof. In some examples, a tumor expressing or regulated by a CB receptor, such as GPR55, and β2-AR is treated by administering one or more disclosed fenoterol analogues possessing CB receptor regulatory activity, such as (R,R')-4'-methoxy-1-naphthylfenoterol (MNF), (R,S')-MNF, (R,R')-ethylMNF, (R,R')-naphthylfenoterol (NF), (R,R')-ethylNF, (R,S')-NF and (R,R')-4'-amino-1-naphthylfenoterol (aminoNF), (R,R')-4'-hydroxy-1-naphthylfenoterol (hydroxyNF), and one or more fenoterol analogues or fenoterol itself having β2-AR stimulatory activity in combination.

Disclosed methods include administering fenoterol, such as (R,R')-fenoterol, a disclosed fenoterol analogue or a combination thereof (and, optionally, one or more other pharmaceutical agents) depending upon the receptor population of the tumor, to a subject in a pharmaceutically acceptable carrier and in an amount effective to treat the tumor expressing a β2-AR, a CB receptor or combination thereof, such as a primary tumor. Treatment of a tumor includes preventing or reducing signs or symptoms associated with the presence of such tumor (for example, by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%, such as between 10%-90%, 20%-80%, 30%-70%, 40%-60%, including a 10%, 15%, 20%, 25%, 30%, 35%, 40%, 45%, 50%, 55%, 60%, 65%, 70%, 75%, 80%, 90%, or 95% reduction. In another example, treatment includes reducing the invasive activity of the tumor in the subject, for example by reducing the ability of the tumor to metastasize. In some examples, treatment using the methods disclosed herein prolongs the time of survival of the subject.

Routes of administration useful in the disclosed methods include but are not limited to oral and parenteral routes, such as intravenous (IV), intraperitoneal (IP), rectal, topical, ophthalmic, nasal, and transdermal as described in detail above.

An effective amount of fenoterol, such as (R,R')-fenoterol, or a disclosed fenoterol analogue or combination thereof will depend, at least, on the particular method of use, the subject being treated, the severity of the tumor, and the manner of administration of the therapeutic composition. A "therapeutically effective amount" of a composition is a quantity of a specified compound sufficient to achieve a desired effect in a subject being treated. For example, this may be the amount of (R,R')-fenoterol, a disclosed fenoterol analogue or a combination thereof necessary to prevent or inhibit tumor growth and/or one or more symptoms associated with the tumor in a subject. Ideally, a therapeutically effective amount of (R, 'R)-fenoterol or a disclosed fenoterol analogue is an amount sufficient to prevent or inhibit a tumor, such as a brain or liver tumor growth and/or one or more symptoms associated with the tumor in a subject without causing a substantial cytotoxic effect on host cells.

Therapeutically effective doses of a disclosed fenoterol compound or pharmaceutical composition can be determined by one of skill in the art, with a goal of achieving concentrations that are at least as high as the $IC_{50}$ of the applicable compound disclosed in the examples herein. An example of a dosage range is from about 0.001 to about 10 mg/kg body weight orally in single or divided doses. In particular examples, a dosage range is from about 0.005 to about 5 mg/kg body weight orally in single or divided doses (assuming an average body weight of approximately 70 kg; values adjusted accordingly for persons weighing more or less than average). For oral administration, the compositions are, for example, provided in the form of a tablet containing from about 1.0 to about 50 mg of the active ingredient, particularly about 2.5 mg, about 5 mg, about 10 mg, or about 50 mg of the active ingredient for the symptomatic adjustment of the dosage to the subject being treated. In one exemplary oral dosage regimen, a tablet containing from about 1 mg to about 50 mg active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy.

Selecting a Subject

Subjects can be screened prior to initiating the disclosed therapies, for example to select a subject in need of or at risk of developing a disorder or disease regulated by CB receptor activity or expression. Briefly, the method can include screening subjects to determine if they have or are at risk of developing a GPR55-regulated disorder or disease, such as if the subject is in need of tumor inhibition. Subjects having a tumor that expresses a CB receptor, such as GPR55, or is regulated by CB receptor activity, such as a primary tumor, including a primary brain tumor, such as a glioblastoma, hepatocellular carcinoma, liver cancer, lung cancer, or colon cancer or at risk of developing such a tumor are selected. In one example, subjects are diagnosed with the tumor by clinical signs, laboratory tests, or both. For example, a tumor, such as a primary brain tumor, can be diagnosed by characteristic clinical signs, such as headaches, vomiting, seizures, dizziness, weight loss and various associated complaints. Diagnosis is generally by imaging analysis such as by magnetic resonance imaging (MRI) and confirmed by histology. In some examples, a subject is selected that does not have a bleeding disorder, such as an intracerebral hemorrhage.

In an example, a subject in need of the disclosed therapies is selected by detecting a tumor expressing a CB receptor (e.g., GPR55) or regulated by its activity, such as by detecting CB receptor activity or expression in a sample obtained from a subject identified as having, suspected of having or at risk of acquiring such a tumor. For example, detection of altered, such as at least a 10% alteration, including a 10%-90%, 20%-80%, 30%-70%, 40%-60%, such as a 10%, 15%, 20%, 25%, 30%, 35%, 40%, 45%, 50%, 55%, 60%, 65%, 70%, 75%, 80%, 90%, 95% alteration or more in CB expression or activity as compared to CB expression or activity in the absence of a primary tumor, indicates that the tumor can be treated using the fenoterol compositions and methods provided herein which are CB receptor regulators. In other examples, a subject is selected by detecting a primary brain tumor such as an astrocytoma or glioblastoma by MRI or positron emission tomography (PET) in a subject.

In some examples, a subject is selected by determining the subject has or is at risk of developing a disorder or disease, such as a tumor and/or cancer, which does not respond to β2-AR stimulation.

Pre-screening is not required prior to administration of the therapeutic agents disclosed herein (such as those including fenoterol, a fenoterol analogue or a combination thereof).

Exemplary Tumors

Exemplary tumors include tumors that express a CB receptor, such as GPR55, or regulated by such, including primary tumors, such as a primary brain tumor. A primary brain tumor includes astrocytomas, glioblastomas, ependymoma, oligodendroglomas, and mixed gliomas. Additional possible types of tumors associated with CB receptor activity or expression include hematological tumors, such as leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of possible solid tumors which may express a CB receptor or be regulated by CB receptor activity, include sarcomas and carcinomas, such as fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, liver cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is a brain cancer, liver cancer, or lung cancer that expresses a CB receptor, such as GPR55. Tumors expressing a CB receptor, such as GPR55, can be identified by routine methods known to those of skill in the art including Western blot and histological studies with antibodies capable of detecting a CB receptor, such as GPR55

Assessment

Following the administration of one or more therapies, subjects having a disorder or disease regulated by CB receptor activity, such as a tumor-expressing GPR55 (for example, a primary tumor) can be monitored for decreases in tumor growth, tumor volume or in one or more clinical symptoms associated with the tumor. In particular examples, subjects are analyzed one or more times, starting 7 days following treatment. Subjects can be monitored using any method known in the art including those described herein including imaging analysis.

Additional Treatments and Additional Therapeutic Agents

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least a 20%, at least a 30%, at least a 40%, at least a 50%, or at least a 70% reduction in one or more signs or symptoms associated with the disorder or disease, such as a tumor regulated by CB receptor activity, including tumor size or volume.

In some examples, the method further includes administering a therapeutic effective amount of fenoterol, a fenoterol analogue or a combination thereof with additional therapeutic treatments. In particular examples, prior to, during, or following administration of a therapeutic amount of an agent that prevents or inhibits a tumor regulated by CB receptor activity, the subject can receive one or more other therapies. In one example, the subject receives one or more treatments to remove or reduce the tumor prior to administration of a therapeutic amount of a composition including fenoterol, a fenoterol analogue or combination thereof.

Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents. Particular examples of additional therapeutic agents that can be used include microtubule-binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule-binding agent" refers to an agent that interacts with tubulin to stabilize or destabilize microtubule formation thereby inhibiting cell division. Examples of microtubule-binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds are of use in the methods disclosed herein: Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Examples of alkylating agents include carmustine or lomustine. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevac, Iressa, and Tarceva that prevent phosphorylation and activation of growth factors.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogues thereof.

In one example, at least a portion of the tumor (such as the primary brain tumor) is surgically removed (for example via cryotherapy), irradiated, chemically treated (for example via chemoembolization) or combinations thereof, prior to administration of the disclosed therapies (such as administration of fenoterol, a fenoterol analogue or a combination thereof). For example, a subject having a primary brain tumor associated with CB receptor activity can have at least a portion of the tumor surgically excised prior to administration of the disclosed therapies. In an example, one or more chemotherapeutic agents are administered following treatment with a composition including fenoterol, a fenoterol analogue or a combination thereof. In another particular example, the subject has a primary brain tumor and is administered radiation therapy, chemoembolization therapy, or both concurrently with the administration of the disclosed therapies.

Additional Disorders and Diseases

As discussed above, in addition to methods of treating CB receptor-regulated tumors, it is contemplated that the disclosed fenoterol analogues possessing CB receptor modulatory activity, such as modulator of GPR55 activity, can be used to treat other conditions associated with CB receptor regulation, such as metabolic disorders and disease (e.g., obesity and diabetes), or inflammatory and neuropathic pain disorders, diseases associated with aging such as Alzheimer's, bone loss, muscle wasting (sarcopenia), osteoarthritis and loss of appetite, central nervous system conditions such as depression and anxiety and other diseases and disorders associated with CB receptor regulation.

Based on these observations, methods of treating metabolic disorders/diseases, (such as obesity, loss of appetite, and/or diabetes), bone and/or muscle disorders or diseases (such as bone loss, muscle wasting, osteoarthritis), central nervous system conditions (such as depression and anxiety) and inflammatory disorders/diseases, such as inflammation, neuropathic pain disorders and diseases associated with inflammation and/or aging (such as Alzheimer's disease, osteoarthritis), are disclosed. For example, disclosed herein are methods of preventing and treating obesity, diabetes, and related disorders.

In one example, a method of treating obesity or a condition associated with obesity, such as diabetes, in a subject is disclosed comprising administering to a subject an effective amount of at least one fenoterol analogue with CB receptor modulatory activity, such as GPR55 activity (e.g., a disclosed naphthylfenoterol analogue, such as (R,R')-4'-methoxy-1-naphthylfenoterol (MNF), (R,S')-MNF, (R,R')-ethylMNF, (R,R')-naphthylfenoterol (NF), (R,R')-ethylNF, (R,S')-NF and (R,R')-4'-amino-1-naphthylfenoterol (aminoNF), (R,R')-4'-hydroxy-1-naphthylfenoterol (hydroxyNF), or a combination thereof), to reduce or inhibit one or more signs or symptoms associated with obesity or a condition associated with obesity. In some examples, methods of treating one or more signs or symptoms associated with an inflammatory disorder and/or disease are disclosed comprising administering to a subject an effective amount of at least one fenoterol analogue with CB receptor modulatory activity, such as GPR55 activity (e.g., a disclosed naphthylfenoterol analogue, such as (R,R')-4'-methoxy-1-naphthylfenoterol (MNF), (R,S')-MNF, (R,R')-ethylMNF, (R,R')-naphthylfenoterol (NF), (R,R')-ethylNF, (R,S')-NF and (R,R')-4'-amino-1-naphthylfenoterol (aminoNF), (R,R')-4'-hydroxy-1-naphthylfenoterol (hydroxyNF), or a combination thereof), to reduce or inhibit one or more signs or symptoms associated with the inflammatory disorder/disease or a condition associated with the inflammatory disorder/disease.

Disclosed methods include administering a disclosed fenoterol analogue with CB receptor modulatory activity (and, optionally, one or more other pharmaceutical agents) to a subject in a pharmaceutically acceptable carrier and in an amount effective to treat the disorder or disease regulated by CB receptor activity, such as GPR55 activity. Treatment of the disorder or disease includes preventing or reducing signs or symptoms associated with the particular disorder or disease. The signs and symptoms associated with the particular disorder or disease are known to one of ordinary skill in the art and can be measured by assays disclosed herein as well as those known to those skilled in the art. In some examples, treatment using the methods disclosed herein prolongs the time of survival of the subject.

Routes of administration useful in the disclosed methods include but are not limited to oral and parenteral routes, such as intravenous (IV), intraperitoneal (IP), rectal, topical, ophthalmic, nasal, and transdermal as described in detail above.

An effective amount of a disclosed fenoterol analogue or combination thereof will depend, at least, on the particular method of use, the subject being treated, the severity of the disorder/disease, and the manner of administration of the therapeutic composition. A "therapeutically effective amount" of a composition is a quantity of a specified compound sufficient to achieve a desired effect in a subject being treated. Ideally, a therapeutically effective amount of a disclosed fenoterol analogue is an amount sufficient to prevent or inhibit one or more symptoms associated with the particular disorder/disease in a subject without causing a substantial cytotoxic effect on host cells.

Therapeutically effective doses of a disclosed fenoterol compound or pharmaceutical composition can be determined by one of skill in the art, with a goal of achieving concentrations that are at least as high as the $IC_{50}$ of the applicable compound disclosed in the examples herein. An example of a dosage range is from about 0.001 to about 10 mg/kg body weight orally in single or divided doses. In particular examples, a dosage range is from about 0.005 to about 5 mg/kg body weight orally in single or divided doses (assuming an average body weight of approximately 70 kg; values adjusted accordingly for persons weighing more or less than average). For oral administration, the compositions are, for example, provided in the form of a tablet containing from about 1.0 to about 50 mg of the active ingredient, particularly about 2.5 mg, about 5 mg, about 10 mg, or about 50 mg of the active ingredient for the symptomatic adjustment of the dosage to the subject being treated. In one exemplary oral dosage regimen, a tablet containing from about 1 mg to about 50 mg active ingredient is administered once to four times a day, such as one time, two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is parenterally administered once per day. However, the composition can be administered twice per day, three times per day, four times per day, six times per day, every other day, twice a week, weekly, or monthly. Treatment will typically continue for at least one month, more often for two or three months, sometimes for six months or a year, and may even continue indefinitely, that is, chronically. Repeat courses of treatment are also possible.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy. In some examples, one or more disclosed fenoterol analogues with CB receptor activity is orally administered to a subject daily to treat one or more symptoms associated with an aging disorder or disease (such as Alzheimer's, sarcopenia, bone loss, or combinations thereof) or a central nervous system disorder or disease (such as anxiety or depression).

Subjects can be screened prior to initiating the disclosed therapies, for example to select a subject in need of or at risk of developing a disorder or disease regulated by CB receptor activity or expression. Briefly, the method can include screening subjects to determine if they have or are at risk of developing a GPR55-regulated disorder or disease. Subjects having a disorder or disease that expresses a CB receptor, such as GPR55, or is regulated by CB receptor activity are selected. In one example, subjects are diagnosed by clinical signs, laboratory tests, or both known to those of ordinary skill in the art or disclosed herein (or both).

Pre-screening is not required prior to administration of the therapeutic agents disclosed herein (such as those including fenoterol, a fenoterol analogue or a combination thereof).

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least a 20%, at least a 30%, at least a 40%, at least a 50%, or at least a 70% reduction in one or more signs or symptoms associated with the disorder or disease.

In some examples, the method further includes administering a therapeutic effective amount of one or more fenoterol analogues with additional therapeutic treatments. In particular examples, prior to, during, or following administration of a therapeutic amount of an agent that prevents or inhibits a tumor regulated by CB receptor activity, the subject can receive one or more other therapies. In one example, the subject receives one or more treatments to remove or reduce one or more signs or symptoms associated with the CB receptor regulated disorder/disease prior to administration of a therapeutic amount of a composition including one or more fenoterol analogues.

In particular examples, prior to, during, or following administration of a therapeutic amount of a disclosed fenoterol analogue composition that reduces or inhibits one or more signs or symptoms of obesity or a condition associated with obesity, the subject can receive one or more other therapies. In one example, the subject receives one or more treatments to remove or reduce one or more conditions associated with obesity, such as diabetes.

Examples of such therapies include, but are not limited to, anti-diabetic agents, insulin sensitizers, insulin secretagogues, agents that preserve and/or increase β-cell mass, agents that enhance glucose-stimulated insulin secretion and glucose uptake in peripheral organs of insulin action (skeletal muscle, liver, adipose tissue), agents that suppress endogenous glucose production, and anti-obesity agents. For example, the disclosed therapies can be administered with anti-diabetic agents such as biguanides. In particular embodiments, the biguanide antidiabetic agent is metformin. Metformin is manufactured by Lyonnaise Industrielle Pharmaceutique SA (Lyons, France), also known by its acronym LIPHA SA, and commercially distributed in the United States as a hydrochloride salt by the Bristol-Myers Squibb Company (Princeton, N.J.) as GLUCOPHAGE® XR. Additionally, Bristol-Myers Squibb distributes a pharmaceutical having a combination of metformin and glyburide as GLU-COVANCE®.

Anti-diabetic agents other than biguanides can also be administered to the identified subject. For example, in alternative embodiments, the anti-diabetic agent is a thiazolidinedione, such as troglitazone. In some examples, the anti-diabetic agent is an incretin or dipeptidyl peptidase-4 inhibitor, but the anti-diabetic agent can be any agent of interest.

A therapeutically effective amount of an anti-diabetic agent may be administered in a single dose, or in several doses, for example daily, during a course of treatment. The course of treatment may last for any length of time, such as a day or several days, a week or several weeks, a month or several months, or a year or several years, so long as the therapeutic effect is observed, such as inhibiting the onset of type II diabetes in a subject diagnosed with pre-diabetes, or inducing a subject diagnosed with type 2 diabetes or pre-diabetes to a normal glucose tolerance. The subject can be monitored while undergoing treatment using the methods described herein in order to assess the efficacy of the treatment protocol. In this manner, the length of time or the amount given to the subject can be modified based on the results obtained using the methods disclosed herein.

The therapeutically effective amount will depend on the anti-diabetic agent being used, the characteristics of the subject being treated (such as age, BMI, physiological condition, etc.), the severity and type of the affliction, and the manner of administration of the agent. The therapeutically effective dose can be determined by various methods, including generating an empirical dose-response curve, predicting potency and efficacy by using quantitative structure-activity relationships (QSAR) methods or molecular modeling, and other methods used in the pharmaceutical sciences. In certain, non-limiting examples, the therapeutically effective amount of metformin (or a related biguanide analog or homolog) is at least about 1000 mg per day, such as at least about 1500 mg per day, or even at least about 1700 mg per day. In certain other, non-limiting examples, the total amount of metformin is divided into smaller doses, such as two or three doses per day, for example 850 mg twice a day (b.i.d.) or 500 mg three times a day (t.i.d.). In alternative, non-limiting examples, the total amount of metformin is about 500 mg or less per day. The subject can be monitored at different doses of an agent using the assays described herein, in order to determine a therapeutically effective amount for the subject of interest.

For administration to animals, purified therapeutically active agents are generally combined with a pharmaceutically acceptable carrier. Pharmaceutical preparations may contain only one type of anti-diabetic agent or may be composed of a combination of several types of anti-diabetic agents, such as a combination of two or more anti-diabetic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Anti-diabetic agents may be administered by any means that achieve their intended purpose. For example, the anti-diabetic agents may be administered to a subject through systemic administration, such as intravenous, intraperitoneal, intralesional, suppository, or oral administration.

The anti-diabetic agent can be administered alone or in combination with another anti-diabetic agent. In certain embodiments, the anti-diabetic agent is administered in the absence of administering any other anti-diabetic agent.

Other measures may be taken to inhibit or delay the onset of type II diabetes in subjects at a heightened risk of developing the disease. For example, in some embodiments, a subject may be instructed, trained, or induced to adopt anti-diabetic lifestyle modifications. For example, the subject can be counseled to reduce caloric intake or to exercise. The methods disclosed herein can be used to monitor the effectiveness of these alternative measures to determine if pharmaceutical intervention is warranted for a subject of interest.

The subject matter of the present disclosure is further illustrated by the following non-limiting Examples.

EXAMPLES

Example 1

Material and Methods

This example describes the Material and Methods used for Examples 2-4.

Materials. (R,R')-, (R,S')-, (S,R')- and (S,S')-fenoterol and the fenoterol analogs, (R,R')-ethylfenoterol, (R,R')-4'-aminofenoterol, (R,R')-1-naphthylfenoterol and (R,R')- and (R,S')-4-methoxy-1-naphthylfenoterol, were synthesized as previously described (Jozwiak et al., *J Med Chem* 50:2903-2915, 2007; Jozwiak et al., *Bioorg Med Chem* 18:728-736, 2010; each of which is incorporated by reference in its entirety). [$^3$H]-Thymidine (70-90 Ci/mmol) was purchased from PerkinElmer Life and Analytical Sciences (Waltham, Mass.). Eagle's Minimum Essential Medium (E-MEM), trypsin solution, phosphate-buffered saline (PBS), fetal bovine serum (FBS), 100× solutions of sodium pyruvate (100 mM), L-glutamine (200 mM), and penicillin/streptomycin (a mixture of 10,000 units/ml penicillin and 10,000 µg/ml streptomycin) were obtained from Quality Biological (Gaithersburg, Md.). WIN 55,212-2, AM251, and AM630 were purchased from Cayman Chemical (Ann Arbor, Mich.). ICI 118,551 hydrochloride and (R)-isoproterenol were obtained from Sigma-Aldrich (St. Louis, Mo.).

Maintenance and Treatment of Cell Lines. Human HepG2 hepatocarcinoma cells and human U87MG glioma cells (ATCC, Manassas, Va.) were maintained in EMEM medium supplemented with 1% L-glutamine, 1% sodium pyruvate, 1% penicillin/streptomycin, and 10% FBS (Hyclone, Logan, Utah). The human 1321N1 astrocytoma cells (European Collection of Cell Cultures, Sigma-Aldrich) were cultured in Dulbecco's modified Eagle's medium supplemented with 10% FBS and penicillin/streptomycin. All cell lines were cultured at 37° C. in 5% $CO_2$, and the medium was replaced every 2-3 days.

Unless otherwise indicated, cells at 70-80% confluence were depleted of serum for 3 hours, followed by the addition of ICI 118551, AM251, AM630 or WIN 55-212,2 for 1 hour before treatment with vehicle, fenoterol or fenoterol derivatives at the indicated concentrations.

[$^3$H]-Thymidine Incorporation Assay. Cells were seeded in 12-well plates at approximately 50,000 cells/well and incubated at 37° C. After 24 hours, the wells were rinsed with PBS and replaced with serum-free medium containing the appropriate concentration of the test compounds. After another 24-hour incubation at 37° C., 1 µCi of [$^3$H]-thymidine was added to each well and incubated at 37° C. for 16 hours. [$^3$H]-Thymidine incorporation into DNA was monitored after the cells were washed twice with PBS and then lysed in 600 µL of 0.1N NaOH for 30 minutes with shaking. The lysate was then mixed with 3 mL of liquid scintillation cocktail (Beckman Coulter, Inc., Brea, Calif.), and radioactivity was measured by liquid scintillation counting using Beckman Coulter LS6000IC Scintillation Counter. Data are shown as CPM incorporated compared to the control cells.

cAMP Accumulation. HepG2 cells were seeded in 96-well plates and grown to confluency. Cells were rinsed in Krebs-HEPES buffer, pH 7.4, pre-incubated for 10 minutes with the buffer, and then 10 µM (R)-isoproterenol or (R,R')-fenoterol was added followed by incubation for an additional 10 minutes. The levels of cAMP accumulated in cells were determined and normalized to the amount of protein per well.

RNA Extraction, cDNA Synthesis, and RT-PCR Analysis. Total RNA was isolated from HepG2, 1321N1 and U87MG cells using the RNeasy Mini kit (Qiagen, Valencia, Calif.). The RNA preparation included a DNAse digestion step. RNA concentration and quality was measured using the NanoDrop spectrophotometer (NanoDrop Technologies, Wilmington, Del.). To obtain cDNA, 1 µg total RNA was reverse-transcribed using the Promega reverse transcription kit (Promega Corp., Madison, Wis.). PCR reactions were performed to determine the expression of CB1R, CB2R, and β2-AR mRNAs using GAPDH as internal control. The PCR primers and conditions are found in Supplemental Table 1.

Cell Cycle Analysis. Cell cycle distributions were performed by flow cytometry on propidium iodide-stained nuclei prepared by the NIM technique. DNA histograms of at least 10,000 cells acquired on a Becton-Dickinson FACScanto II (BD Biosciences, San Jose, Calif.) were deconvoluted using the Multicycle program (Phoenix Flow Systems) for estimates of the percentage of cells in the G0/1, S, and G2+M phases of the cell cycle. Debris and doublets were removed from the analysis by software algorithms.

Apoptosis Assay. The degree of apoptosis induced by drug treatment was assayed by flow cytometry using the Alexa Fluor® 488 annexin V/Dead Cell Apoptosis Kit (Invitrogen) following the standard manufacturer's protocol. Briefly, HepG2 cells ($5\times10^5$) were grown on 100-mm dishes for 24 hours followed by treatment with vehicle, (R,R')-fenoterol, or (R,R')-MNF, all in serum-free medium. Cells were subsequently harvested after a 24-hour incubation, washed in cold PBS, and resuspended in 100 μL of 1× annexin-binding buffer to maintain a density~$1\times10^6$ cells/mL, after which 5 μL Alexa Fluor® 488 annexin V and 1 μL 100 μg/mL propidium iodide were added to the cell suspensions. Cells were then incubated at room temperature for 15 minutes and 400 μL 1× annexin-binding buffer was added followed by gentle mixing. Stained cells were analyzed on a BDFACSCanto II flow cytometer.

Western Blotting. Cells were lysed with RIPA buffer containing EGTA and EDTA (Boston BioProducts, Ashland, Mass.). The lysis buffer was mixed with a protease inhibitor cocktail (Sigma-Aldrich). Protein concentrations were measured using the bicinchoninic acid reagent (Thermo-Pierce Biotechnology, Inc., Rockford, Ill.). Proteins (20 μg/well) were separated on 4-12% precast gels (Invitrogen, Carlsbad, Calif.) using SDS-polyacrylamide gel electrophoresis under reducing conditions and were electrophoretically transferred onto polyvinylidene fluoride membrane (Invitrogen). Western blots were performed according to standard methods. The visualization of immunoreactive bands was performed using the ECL Plus Western Blotting Detection System (GE Healthcare, NJ) and their quantification was done by volume densitometry using Image J software and normalization to β-actin. The primary antibody for β2-AR was obtained from Enzo Life Sciences, Inc. (Cat. #ADI-905-742-100, Farmingdale, N.Y.); rabbit anti-phospho-Akt (Ser-473), phospho-ERK1/2, total Akt and total ERK2 were from Cell Signaling Technology (Beverly, Mass.), and anti-β-actin was from Abcam (Cambridge, Mass.). The antibodies were used at a dilution recommended by the manufacturer.

Statistical Analysis. Results were expressed as relative to the control value. Studies were performed in at least two to three different culture preparations, and two to three dishes for each test condition were plated in each preparation. Results are expressed as means±S.E. Student's t-test was used to make statistical comparisons between groups. Analyses were performed using the SigmaPlot Software (Systat Software, Inc. San Jose, Calif.), Graphpad Prism 4 (GraphPad Software, Inc., La Jolla, Calif.) and Microsoft® Office Excel, 2003 (Microsoft Corp., Redmond, Wash.), with p values ≤0.05 considered significant.

Example 2

Characterization of Fenoterol and Fenoterol Analogs on Cannabinoid Receptor Activity This example describes a series of studies performed to characterize the ability of fenoterol and disclosed fenoterol analogs to modulate cannabinoid receptor activity.

(R,R')-Fenoterol, (R,R')-Fen, is a potent and selective agonist of the $\beta_2$-adrenergic receptor ($\beta_2$-AR), which has a 43-fold higher affinity for the $\beta_2$-AR relative to the $\beta_1$-AR and an $EC_{50cAMP}$ value of 0.3 nM for the stimulation of cAMP accumulation in HEK cells expressing human $\beta_2$-AR. The inventors have disclosed the synthesis and characterization of a number of (R,R')-Fen analogs and stereoisomers with a range of $\beta_2$-AR selectivity and potency (see, for example International Patent Publication No. WO 2008/022038 and WO 2011/112867, each of which is incorporated by reference in its entirety herein). One of these analogs, (R,R')-4-methoxy-1-naphthylfenoterol (MNF) has a $\beta_2$-AR selectivity of 573 with an $EC_{50cAMP}$ of 3.90 nM.

$\beta_2$-ARs associate with heterotrimeric G proteins (e.g., $G_s$, $G_i$), ion channels and cytosolic scaffold proteins, including β-arrestin, to initiate various signaling pathways and modulate the activity of intracellular effectors such as adenyl cyclase and mitogen-activated protein kinase (MAPK). The difference in the G protein and β-arrestin signaling by $\beta_2$-AR agonists has been attributed to interaction with ligand-specific GPCR conformations and functional selectivity, which is based upon the assumption that the $\beta_2$-AR exists in an inactive (R) state and one or more ligand-specific active conformations (R*"). The basis for the ligand-specific differences in pharmacological outcome lies in the interplay between the molecular structure of the agonist and the cellular environment of the receptor. In the first instance, the inventors have shown that the $G_s/G_i$ selectivity of Fen is a function of molecular structure and stereochemistry as (R,R')-Fen preferentially activated $G_s$ signaling in a cardiomyocyte contractility model while (S,R')-Fen and (R,R')-MNF activated both $G_s$ and $G_i$ proteins. In the latter case, the inventors have demonstrated that β2-AR agonists such as (R,R')-Fen and isoproterenol exert anti-proliferative effects in the human-derived 1321N1 astrocytoma cell line specifically through the cAMP-dependent pathway while Yuan and colleagues (*Oncol Rep* 23:151-157, 2010) reported that isoproterenol dose-dependently induced the growth of the human-derived HepG2 hepatocellular carcinoma cell line.

The current example describes the effect of the molecular structure and stereochemistry of $\beta_2$-AR agonists on [$^3$H]-thymidine incorporation in HepG2 cells and to compare these results to similar studies conducted using the 1321N1 and human-derived U87MG glioblastoma cells lines. The initial data demonstrated that (R,R')-Fen and isoproterenol induced [$^3$H]-thymidine incorporation in HepG2 cells, reduced proliferation in 1321N1 cells and had no effect on U87MG cells and that the effects in the HepG2 and 1321N1 cells could be attenuated by the β2-AR antagonist ICI 118551. When (R,R')-MNF was utilized in the studies, opposite results were obtained as the compound inhibited [$^3$H]-thymidine incorporation in HepG2 cells and had no significant effect on 1321N1 cells. The inhibitory effect of (R,R')-MNF in HepG2 cells was not affected by the addition of ICI 118551 and (R,R')-MNF also attenuated [$^3$H]-thymidine incorporation in the $\beta_2$-AR-deficient U87MG cell line. These results indicate that while (R,R')-MNF is a full $\beta_2$-AR agonist, the anti-proliferative effects of this compound are not due to this activity. Further studies indicated that AM251 and AM630, inverse agonists of the CB1 and CB2 cannabinoid receptors, respectively, blocked (R,R')-MNF mitogenic responses in HepG2 and U87MG cell lines and that WIN 55,212-2, a synthetic $CB_1$ and $CB_2$ receptor agonist, produced growth inhibition in these cell lines. These results suggest that cannabinoid receptor activation is associated with the cell type-dependent antiproliferative and pro-apoptotic effects of (R,R')-MNF.

Expression of $\beta_2$-AR in select human cancer cell lines. The protein levels of the $\beta_2$-AR were determined by Western blot analysis in total extracts of HepG2 hepatocarcinoma cells, 1321N1 astrocytoma cells, and U87MG glioma cells (FIG. 1A). $\beta_2$-AR protein level was the highest in 1321N1 cells when compared to HepG2 cells. U87MG cells were previously found by the inventors to be devoid of $\beta_2$-AR at the cell surface.

Effect of $\beta$-AR agonists on cAMP accumulation and phosphorylation of Akt and ERK1/2 HepG2 cells. Neither (R)-isoproterenol nor (R,R')-Fen, at 10 µM, elicited an increase in cAMP production in HepG2 cells, whereas cell treatment with the adenylate cyclase activator, forskolin, induced significant accumulation of cAMP (FIG. 1B). Studies have demonstrated that $\beta_2$-AR can signal to the mitogen-activated protein kinases ERK1 and ERK2 independent of a functional adenylate cyclase coupling. The effect of isoproterenol and (R,R')-Fen on Akt and ERK1/2 activation was assessed by imunoblotting using selective antibodies to phosphorylated peptides that correspond to the active forms of Akt and ERK1/2. Treatment of HepG2 cells with these $\beta$-agonists induced a time-dependent increase in Akt and ERK activation (FIG. 1C). These results indicate that due to low receptor number, $\beta_2$-AR-stimulated adenylyl cyclase activity might be below detectable levels in this cell line.

The effects of (R)-isoproterenol and Fen analogs on the proliferation of HepG2 cells. The effect of (R)-isoproterenol, (R,R')-Fen and selected Fen analogs on cell proliferation was determined in HepG2 cells. Both (R)-isoproterenol and (R,R')-Fen produced a significant increase in cell proliferation, as assessed by [$^3$H]-thymidine incorporation, with $ED_{50}$ of 0.40±0.08 µM and 1.17±0.37 µM, respectively (Table 1; FIG. 2A). Fen has two chiral centers and has 4 possible stereoisomeric forms, (R,R'), (R,S'), (S,R') and (S,S'). The effect of the stereochemistry on the proliferative effect of Fen was determined using a concentration of 1 µM of each isomer. The data indicate that all of the isomers induced an increase in [$^3$H]-thymidine incorporation and that stereochemistry had only a quantitative effect on this process with (R,R')-Fen producing the greatest increase (51.3%) and (S,S')-Fen the lowest (9.7%) (Table 1). This result was consistent with the previously reported inhibitory effect of Fen stereoisomers on mitogenesis in 1321N1 cells in which the inhibitory potency was (R,R')>(R,S') (S,R')>> (S,S') (see Table 1 below). The effect of the change of the N-alkyl methyl group to an ethyl moiety {(R,R')-ethylFen} and the substitution of an 4'-amino group for the 4'-hydroxyl group {(R,R')-aminoFen} were also investigated. Neither alteration changed the direction of the effect on [$^3$H]-thymidine incorporation and (R,R')-aminoFen appeared to be 3-fold more active than (R,R')-Fen with an $EC_{50}$=0.47±0.09 µM (Table 1; FIG. 2A).

Figure 2B:
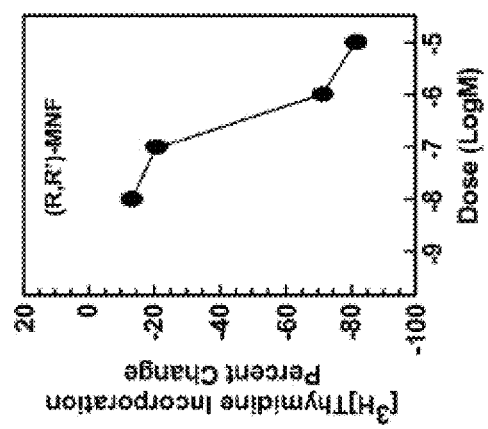

The inventors determined that the incorporation of a naphthyl moiety into the Fen molecule reduced the potency of the resulting compound, but not the inhibitory effect on mitogenesis in 1321N1 cells. Further, the opposite effect was observed as (R,R')-MNF and 1-naphthylFen inhibited [$^3$H]-thymidine incorporation with $IC_{50}$ values of 0.39±0.09 µM and 0.21±0.07 µM, respectively (Table 1; FIG. 2B). The change in the stereochemistry of the chiral center on the N-alkyl portion of the MNF molecule had no effect on the anti-proliferative response as 1 µM concentrations of (R,R')-MNF and (R,S')-MNF produced equivalent decreases in [$^3$H]-thymidine incorporation of −59.4% and −68.1%, respectively (Table 1).

TABLE 1

Structures, percent change in thymidine incorporation and $IC_{50}/EC_{50}$ of fenoterol (Fen) and analogs that were used for this study.

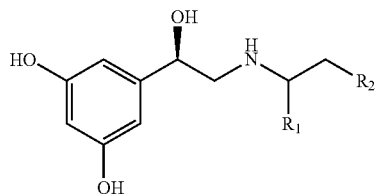

| Compounds | R1 | R2 | $IC_{50}/EC_{50}$ (µM) | % Change in HepG2 cells | Mitogenesis Inhibition in 1321N1 cells ($IC_{50}$ nM)* |
|---|---|---|---|---|---|
| Fen | CH$_3$ | ⸺⟨⟩⸺OH | 1.17 ± 0.37 (n = 6) | (R,R'): 51.3<br>(R,S'): 19.1<br>(S,R'): 28.7<br>(S,S'): 9.7 | 0.14 ± 0.07<br>6.09 ± 1.93<br>6.74 ± 2.18<br>184.2 ± 26.1 |
| ethylFen | CH$_3$—CH$_2$ | ⸺⟨⟩⸺OH | n.d. | (R,R'): 50.90 at 10 µM | 1.44 ± 0.27 |

TABLE 1-continued

Structures, percent change in thymidine incorporation and IC$_{50}$/EC$_{50}$ of fenoterol (Fen) and analogs that were used for this study.

| Compounds | R1 | R2 | IC$_{50}$/EC$_{50}$ (μM) | % Change in HepG2 cells | Mitogenesis Inhibition in 1321N1 cells (IC$_{50}$ nM)* |
|---|---|---|---|---|---|
| aminoFen | CH$_3$ | (4-aminophenyl) | 0.47 ± 0.09 (n = 3) | (R,R'): 54.37 | |
| 1-naphthylFen | CH$_3$ | (1-naphthyl) | 0.21 ± 0.07 (n = 2) | (R,R): −67.52 | 1.57 ± 0.34 |
| 4'-methoxy-1-naphthylFen | CH$_3$ | (4-methoxy-1-naphthyl) | 0.39 ± 0.09 (n = 6) | (R,R'): −59.4 (R,S'): −68.1 | 3.98 ± 0.28 4.37 ± 0.70 |

Figure 2C:
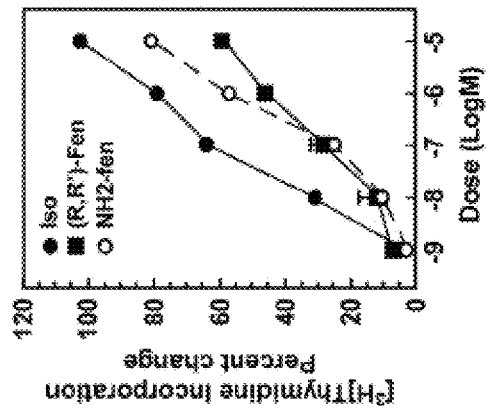
Figure 7:
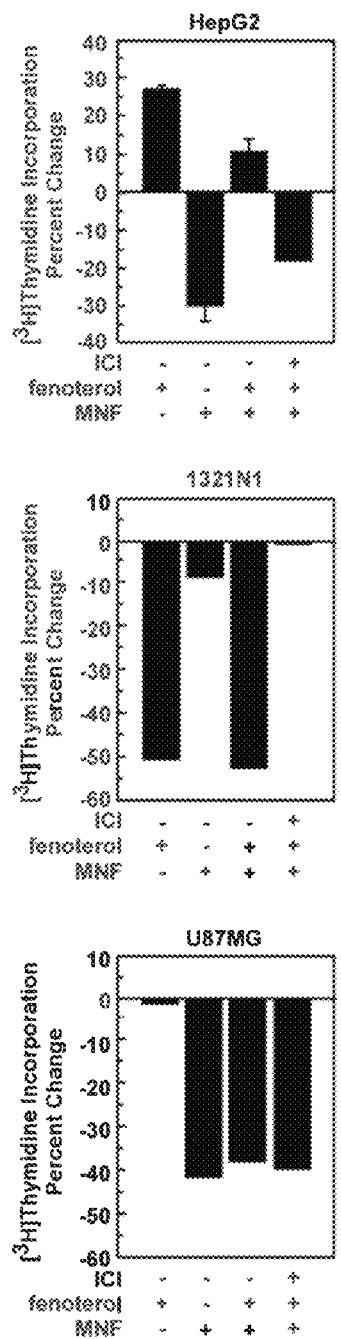
FIG. 7 is a series of graphs illustrating selective inhibition of (R,R')-Fen-mediated cell proliferation control by the β2-AR antagonist, ICI-118,551. HepG2, 1321N1 and U87MG cells were incubated with the β2-AR antagonist, IC-118,551 (ICI, 1 μM), for 1 hour followed by the addition of vehicle, (R,R')-Fen (0.5 μM), or (R,R')-MNF (0.25 μM) for 24 hours, and levels of [$^3$H]-thymidine incorporation was measured. Quantification of percent change in [$^3$H]-thymidine incorporation versus control are expressed as means±SD and represent results from three independent studies, each performed in triplicate dishes.

(R,R')-MNF is a full and potent β$_2$-AR agonist in respect to the stimulation of cAMP expression in HEK cells stably transfected with β2-AR and in 1321N1 cells, with EC$_5$O of 3.9 nM and 68.9 nM, respectively. Since HepG2 cells displayed substantial sensitivity to (R,R')-aminoFen (EC$_{50}$=0.47±0.09 μM) and (R,R')-MNF (IC$_{50}$=0.39±0.09 μM) with regard to [$^3$H]-thymidine incorporation, the responsiveness of 1321N1 cells to the two compounds was determined and found to be markedly lower (FIG. 2C). The specificity of the observed β$_2$-AR response to (R,R')-Fen and (R,R')-MNF in the HepG2 and 1321N1 cells was tested using the U87MG cells, which had been previously shown to lack the expression of active β$_2$-AR. In this cell line, (R,R')-MNF produced a potent inhibition of cellular proliferation while (R,R')-Fen had no effect (FIG. 7).

Figure 2D:
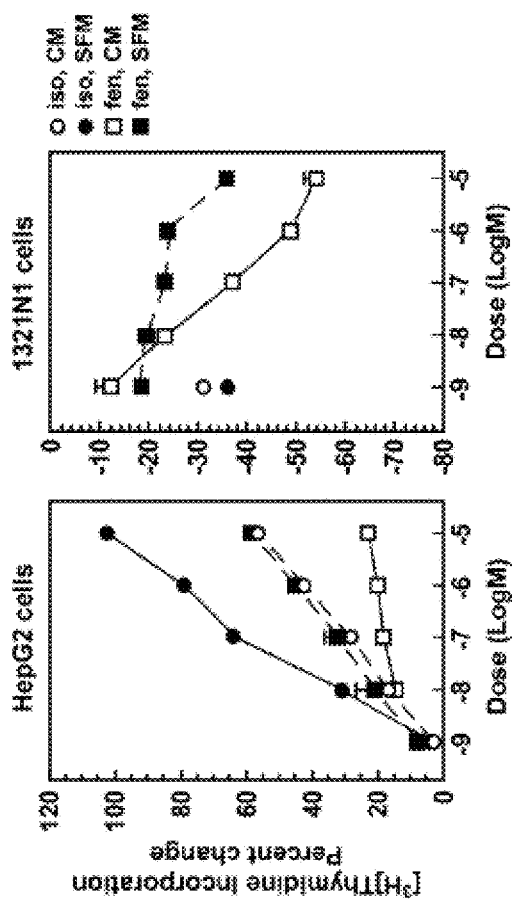

In the previous study of the effect of (R)-isoproterenol and (R,R')-Fen on mitogenesis in 1321N1 cells, the studies were conducted using complete medium. In order to determine if the presence of serum or its absence significantly influenced the extent of mitogenesis in response to (R)-isoproterenol and (R,R')-Fen, the studies were repeated using both protocols. The results indicated that HepG2 cells exhibited a better sensitivity in serum-depleted medium, whereas the sensitivity was greater in 1321N1 cells maintained in complete medium (FIG. 2D). These data suggest that there are contrasting mitogenic responses to β$_2$-AR agonists in HepG2 and 1321N1 cells.

β$_2$-AR antagonism does not inhibit the anti-proliferative action of (R,R')-MNF while preventing (R,R')-Fen's growth promoting effects in HepG2 cells. The divergent actions mediated by (R,R')-Fen and (R,R')-MNF are consistent with activation of distinct signaling pathways with opposite effects on cell proliferation. To evaluate this, HepG2 cells were pretreated with the β$_2$ receptor antagonist, ICI 118,551, followed by incubation in the presence of (R,R')-Fen or (R,R')-MNF for 24 h. While ICI 118,551 alone showed no effect on cell proliferation (FIG. 3A), its addition significantly blocked (R,R')-Fen-stimulated mitogenesis (FIGS. 3B and 3C). However, the anti-proliferative effect of (R,R')-MNF was refractory to ICI 118,551 pretreatment (FIGS. 3B and 3D).

The ability to hamper the action of (R,R')-Fen by the co-addition of MNF was determined. The results showed clearly a mitogenic response in HepG2 cells that was intermediate between (R,R')-Fen and (R,R')-MNF alone, and the pretreatment with ICI 118,551 partially restored the anti-proliferative effects of (R,R')-MNF (FIG. 7, upper panel). However, characteristics of the cell proliferation profile elicited by (R,R')-Fen in 1321N1 cells and (R,R')-MNF in U87MG cells were maintained by the co-treatment with (R,R')-Fen and (R,R')-MNF (FIG. 7, middle and lower panels). Pretreatment with ICI 118,551 blocked (R,R')-Fen signaling in 1321N1 cells while being inactive against the anti-proliferative action of (R,R')-MNF in U87MG cells (FIG. 7). These results indicate that the effects of (R,R')-Fen and (R,R')-MNF on cell proliferation are cell type-specific and may require activation of distinct receptors.

Figure 4:
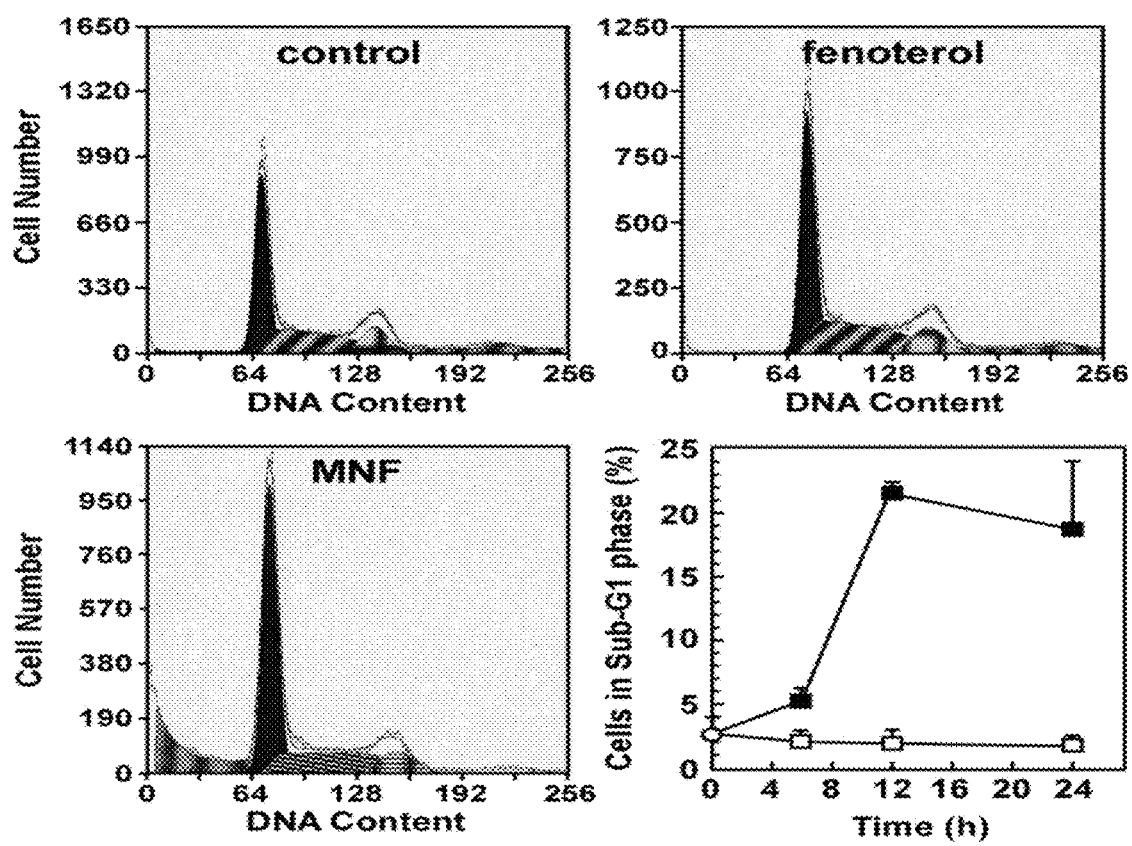
FIG. 4 illustrates (R,R')-MNF increases the number of sub-G1 events in HepG2 cells. Serum-depleted HepG2 cells were harvested after 6-hour, 12-hour or 24-hour treatment with vehicle, (R,R')-Fen (1 μM) or (R,R')-MNF (1 μM). Cells were fixed, stained, and analyzed for DNA content using; flow cytometry, Representative DNA content analysis in various phases of the cell cycle after 24-hour treatment with vehicle, (R,R')-Fen, or (R,R')-MNF are shown. The number of sub-G1 events, which represents dead cells or cells in late-stage apoptosis, was quantified as a function of treatment duration using results from two independent studies, each performed in duplicate (lower right panel). Data are expressed as means±SE (n=4).

(R,R')-MNF induces apoptosis in HepG2 cells. The proliferation of HepG2 cells was assessed by flow cytometry analysis using propidium iodide staining to examine the cell cycle. (R,R')-Fen produced no significant alterations of the cell cycle, but (R,R')-MNF caused a temporal decrease in the $G_2M$- and S-phase cell populations ($G_2$/M: 13.8±1.1% in control versus 10.2±0.9% after 6 h, 14.6±1.8% after 12 h and 8.9±1.6% after 24 S: 34.7±0.3% in control versus 34.1±0.9% after 6 h, 13.7±1.2% after 12 h and 24.6±4.2% after 24 h) in HepG2 cells treated with 1 µM (R,R')-MNF (FIG. 4). The treatment with (R,R')-MNF also yielded a time-dependent increase in the number of sub-$G_1$ events, reaching a maximum of 21.5±0.7% by 12 hours (FIG. 4, bottom, right panel). No significant increase in sub-$G_1$ events was observed when cells were treated with (R,R')-Fen (1 µM) for up to 24 hours.

Figure 5:
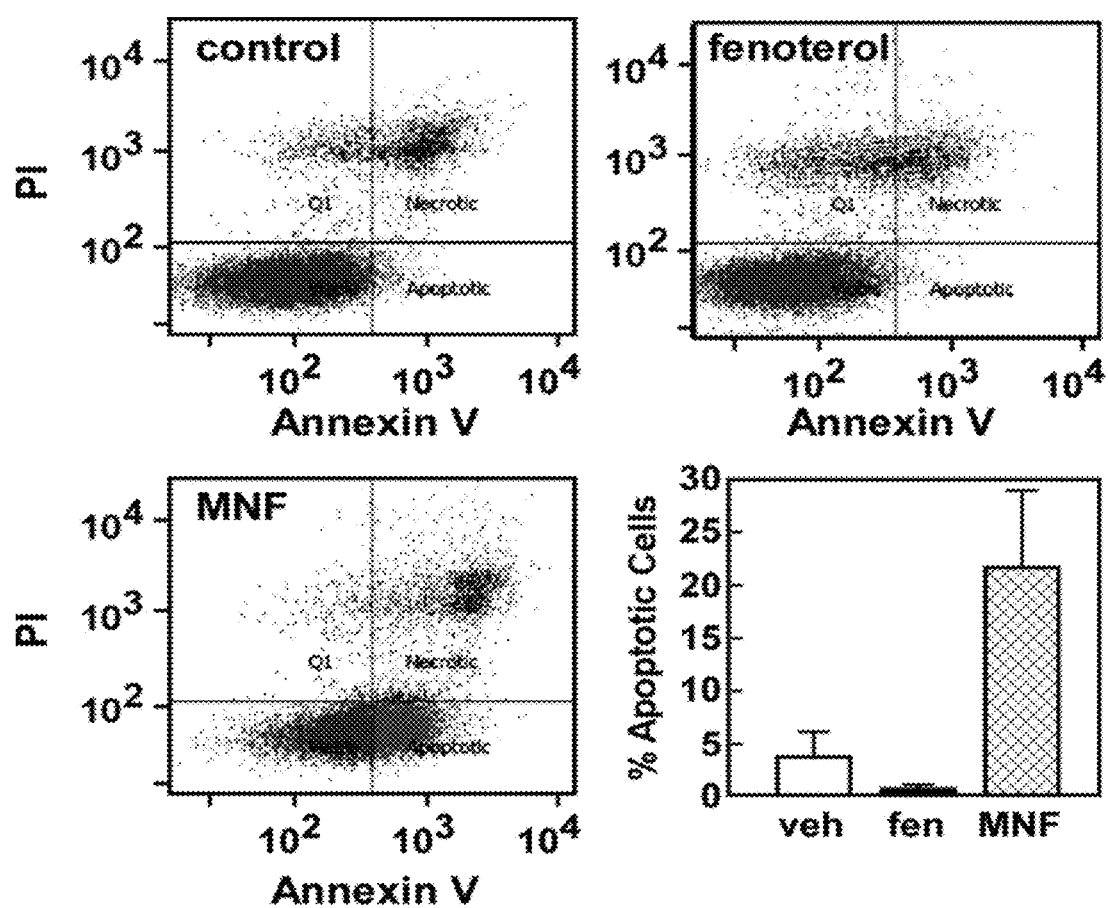
FIG. 5 illustrates the results of flow cytometry studies in which (R,R')-MNF induced apoptosis in HepG2 cells. Serum-depleted HepG2 cells were treated with vehicle, (R,R')-Fen (1 μM), or (R,R')-MNF (1 μM) for 24 hours; stained with Annexin V and propidium iodide (PI); and then analyzed by flow cytometry. Representative profiles are shown. The fraction of annexin V-positive HepG2 cells that were apoptotic was quantitated using results from two independent studies, each performed in duplicate (lower right panel). Data are expressed as means±SE (n=4).
Figure 6A:
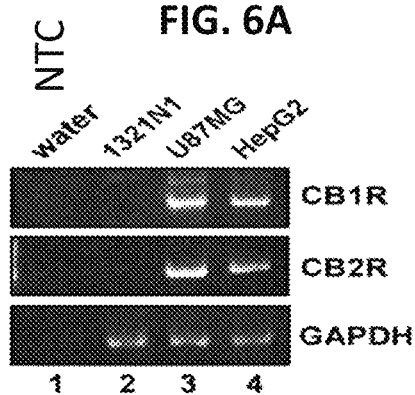
FIGS. 6A-6C illustrate the role of cannabinoid receptor activation in the anti-proliferative action of (R,R')-MNF in HepG2 cells.
Figure 6B:
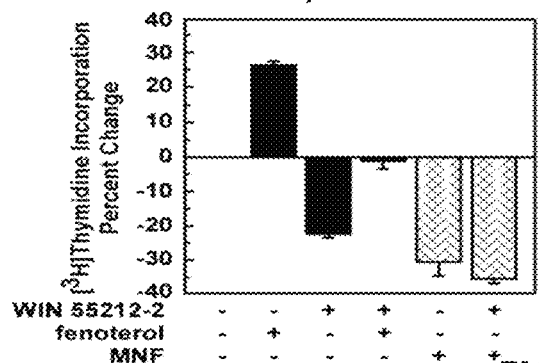
Figure 6C:
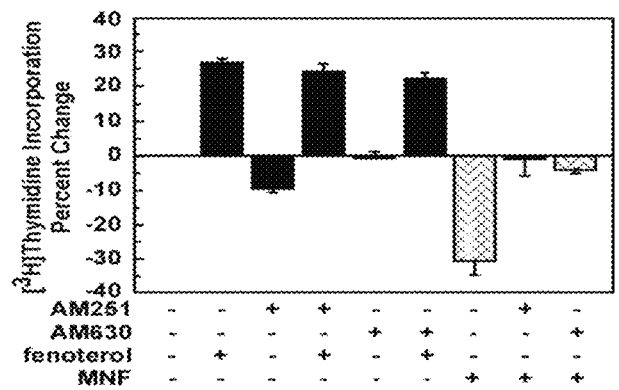

Sub-$G_1$ events occur when cells have proceeded to the late stage of apoptosis or are already dead. To directly measure apoptosis, flow cytometry analysis with Annexin V/PI staining was carried out in HepG2 cells. The percentage of apoptotic cells induced by a 24-hour treatment with (R,R')-MNF (1 µM) increased 5.7-fold compared to the control (P<0.01). However, (R,R')-Fen treatment markedly reduced apoptosis when compared to control untreated cells (FIG. 5).

detectable levels of CBR mRNAs. Potent regulatory effects of synthetic cannabinoid compounds were observed in cells treated with (R,R')-Fen and (R,R')-MNF as compared with controls. Similar to (R,R')-MNF, treatment of HepG2 cells with the cannabinoid receptor agonist, WIN55,212-2 (1 µM), reduced cell proliferation and canceled out the growth-promoting action of fenoterol (FIG. 6B). AM251 and AM630 are synthetic inverse agonists for CB1R and CB2R, respectively. Cell pretreatment with AM251 or AM630 had no impact on the mitogenic responses of (R,R')-Fen (FIG. 6C), indicating that basal-level activity of these two cannabinoid receptors does not play a major role in the proliferative action of (R,R')-Fen. However, preincubation with AM251 or AM630 completely inhibited the anti-proliferative effects of (R,R')-MNF in HepG2 cells (FIG. 6C), which is consistent with the involvement of cannabinoid receptors in (R,R')-MNF signaling. In support of this hypothesis, 1321N1 cells, which are (R,R')-MNF unresponsive, were refractory to cannabinoid receptor ligands when added alone or combined with (R,R')-Fen (FIGS. 8A and 8B). However, the anti-proliferative effects of MNF were partially blocked by AM251 and AM630 in the $\beta_2$-AR-deficient, MNF responsive U87MG cells (FIGS. 8C and 8D).

TABLE 2

List of PCR primers and assay conditions. Each of the references listed in the below Table is hereby incorporated by reference in its entirety.

| Human Gene | Primers | Initial Denaturation | Amplification (35 cycles) Denaturation | Annealing | Extension | Final extension |
|---|---|---|---|---|---|---|
| CB1 (SEQ ID NOs: 1 and 2, resp.) | F: 5' CGTGGGCAGCCT GTTCCTCA R: 5'- CATGCGGGCTTG GTCTGG | 95° C./ 5 min | 94° C./ 30 sec | 57° C./ 30 sec | 72° C./ 1 min | 72° C./ 5 min |
| CB2 (SEQ ID NOs: 3 and 4) | F: 5' CGCCGGAAGCCC TCATACC R: 5'- CCTCATTCGGGC CATTCCTG | 95° C./ 5 min | 94° C./ 30 sec | 57° C./ 30 sec | 72° C./ 1 min | 72° C./ 5 min |
| GAPDH (SEQ ID NOs: 5 and 6, resp.) | F: 5'- ACCACAGTCCAT GCCATC R:5'- TCCACCACCCTG TTGCTG | 94° C./ 4 min | 94° C./ 1 min | 53° C./ 1 min | 72° C./ 1 min | 72° C./ 10 min |
| β2AR (SEQ ID NOs: 7 and 8, resp.) | F: 5'- CATGTCTCTCAT CGTCCTGGCCA R: 5'- CACGATGGAAGA GGCAATGGCA | 94° C./ 6 min | 94° C./ 1 min | 58° C./ 30 sec | 72° C./ 1 min | 72° C./ 5 min |

Role of cannabinoid receptors in the control of cell proliferation of (R,R')-MNF and (R,R')-Fen. Whether the regulation of mitogenesis in response to (R,R')-Fen and (R,R')-MNF occurs through cannabinoid receptor signaling mechanisms was examined. The mRNA levels of CB1R and CB2R were determined by RT-PCR in HepG2, 1321N1 and U87MG cells (FIG. 6A, primers provided below in Table 2). The results indicated that HepG2 and U87MG cells expressed $CB_1R$ and $CB_2R$, whereas 1321N1 cells had no The present Example demonstrates that treatment of HepG2 cells with (R,R')-Fen led to increased cellular proliferation. ICI 118,551 blocked this effect indicating the involvement of $\beta_2$-ARs. However, neither (R,R')-Fen- or isoproterenol induced formation of cAMP in HepG2 cells, although treatment with forskolin demonstrated that the cells expressed functional adenylate cyclase (FIG. 1). These results support two possibilities to explain the lack of effect of $\beta_2$-AR agonists on cAMP accumulation: either the β₂-ARs are at a low enough level that they do not significantly increase cAMP, or the β₂-ARs in the HepG2 cell line are poorly coupled to the stimulatory Gα protein and suggest potential interactions with other signaling intermediates that promote cell growth. The present results demonstrate that treatment of HepG2 cells with (R,R')-Fen or isoproterenol activated the PI3-kinase/Akt and ERK pathways.

Previous studies on the effect of the stereochemistry of Fen on β₂-AR-associated stimulation of cAMP accumulation and inhibition of mitogenesis in 1321N1 cells have demonstrated that changes in the spatial configurations at the molecule's two chiral centers produces only quantitative changes in these properties. A similar effect of stereochemistry was observed in the HepG2 cells as all of the Fen stereoisomers produced an increase in [$^3$H]-thymidine incorporation (reported as % change) with (R,R')>>(S,R')≈(R,S')>>(S,S') (Table 1). The effect of structural changes in the (R,R')-Fen molecule was investigated by increasing the steric bulk at the chiral center on the N-alkyl portion of the molecule, (R,R')-ethylFen, and by changing the hydrogen bonding properties of the 4'-substituent, (R,R')-aminoFen. Both analogs increased [$^3$H]-thymidine incorporation in HepG2 cells to the same extent as (R,R')-Fen (Table 1 and FIG. 2A), suggesting that when the Fen molecule contains a 4'-substituted phenyl ring, the compound stimulates [$^3$H]-thymidine incorporation in HepG2 cells and that the stereochemistry of the molecule influences this effect, but does not qualitatively change it. A full structure-activity relationship study has been initiated and the results will be reported elsewhere.

The inventors demonstrated that naphthylfenoterol (NF) analogs of Fen produced by the substitution of a naphthyl moiety for the phenyl ring on the N-alkyl portion are full and potent β₂-AR agonists with respect to the stimulation of cAMP expression in HEK cells stably transfected with β₂-AR (HEK-β₂-AR); for example, $EC_{50cAMP}$ of (R,R')-1-NF and (R,R')-MNF were 12.5 and 3.9 nM, respectively. As was observed with (R,R')-Fen, (R,R')-1-NF and (R,R')-MNF also inhibited mitogenesis in 1321N1 cells although the $IC_{50}$ values were >10-fold higher than (R,R')-Fen (Toll et al., *J Pharmacol Exp Ther* 336:524-32, 2011). A similar quantitative effect was expected when HepG2 cells were incubated with (R,R')-1-NF and (R,R')-MNF, that is, a weaker stimulation of [$^3$H]-thymidine incorporation. However, a qualitative different effect was observed as (R,R')-MNF and (R,R')-1-NF inhibited [$^3$H]-thymidine incorporation with $IC_{50}$ values of 0.39±0.09 μM and 0.21±0.07 μM, respectively (Table 1 and FIG. 2B). In addition, unlike Fen, a change in the stereochemistry of the chiral center on the N-alkyl portion of the MNF molecule had no effect on the anti-proliferative response (Table 1).

Since the Fen and NF analogs used in this study are β₂-AR agonists, a potential explanation for the effect produced by the substitution of a naphthyl ring for a phenyl ring is "ligand-directed signaling" or "biased agonism." It has been demonstrated that the β₂-AR binds ligands in multiple conformations and that binding to different receptor conformations can lead to differences in signal transduction. In respect to the Fen and NF molecules, initial Comparative Molecular Field Analysis (CoMFA) studies of the interaction of the Fen analogs with the β₂-AR have indicated that the naphthyl substituent of the NFs molecules can interact with the β₂-AR through a series of π-π and π-hydrogen bond interactions unavailable to the phenyl moiety on the Fen molecule. However, the direct association of the binding of the NF analogs and the decrease in [$^3$H]-thymidine incorporation appears doubtful as the selective pharmacological β₂-AR antagonist, ICI 118,551, failed to block the anti-proliferative action of (R,R')-MNF (FIG. 3) and treatment of the β₂-AR-negative U87MG cells with (R,R')-MNF causes a marked reduction in cell growth while (R,R')-Fen had no effect (FIG. 7). This data does not eliminate the possibility that NFs bind to and stabilize a conformation of the β₂-ARs expressed in HepG2 cells that is distinct from the conformation stabilized by (R,R')-Fen, but it suggests that if this occurs it does not result in the initiation of a downstream signaling cascade that effects cellular growth.

Pharmacological evidence disclosed herein indicates that (R,R')-MNF mediates its anti-proliferative effects through activation of the CB receptors. On one hand, this action of (R,R')-MNF was reproduced by WIN 55,212-2 in HepG2 and U87MG cells, and the combination (R,R')-MNF plus WIN 55,212-2 showed a lack of additive effect. On the other hand, selective inhibition of the CB1 and CB2 receptors showed suppression of (R,R')-MNF signaling. The finding of a lack of effect of the WIN 55,212-2-mediated actions on cell growth in 1321N1 cells may be explained by there being substantially more CBR expression in HepG2 and U87MG cell lines than in 1321N1 cells. Moreover, the present results demonstrate that the (R,R')-Fen-mediated increase in HepG2 cell proliferation was neutralized by WIN 55,212-2, possibly indicating that stimulation of $G_i$-linked CBRs in response to WIN 55,212-2 inhibits cell growth primarily by negatively targeting the PI3-kinase/Akt and/or ERK pathways. Taken together, these findings indicate a complex cell type-specific involvement of CB receptors in the anti-mitogenic and proapoptotic activities of (R,R')-MNF through a mechanism that does not require β₂-AR activation.

Example 3

Characterization of Cannabinoid Receptor Modulation

This example describes a series of studies performed to further characterize the ability of fenoterol and disclosed fenoterol analogs to modulate cannabinoid receptor activity.

Figure 9:
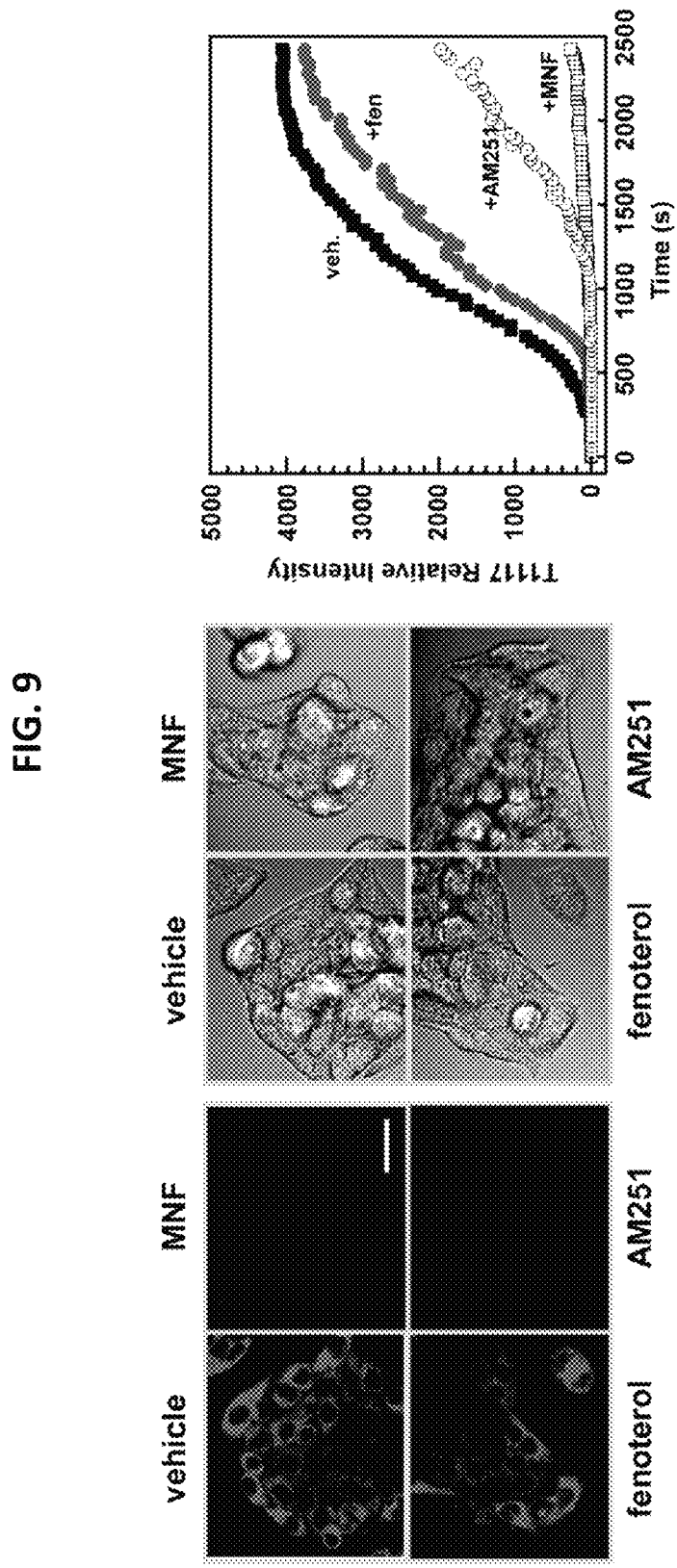
FIG. 9 illustrates cellular uptake of TocriFluor 1117 (T1117), a fluorescent AM251 analog, in HepG2 cells. Cells were treated with (R,R')-Fen (1 μM), (R,R')-MNF (1 μM), or AM251 (10 μM) for 1 hour followed by addition of T1117 (0.1 μM). Cells were mounted on confocal microscope and maintained at 37° C. with $CO_2$. Images were captured every 30 seconds for up to one hour.

To identify the type of CB receptor mediating the (R,R')-MNF-induced response, the effect of MNF on TocriFluor 1117 (T1117, Tocris Bioscience) uptake in HepG2 cells was evaluated. T1117 is a fluorescent form of the cannabinoid CB1 receptor inverse agonist AM251, which binds GPR55 with high affinity, but has modest binding with CB1 receptors and no interaction with CB2 receptors. HepG2 cells were incubated with fenoterol (1 μM), MNF (1 μM) or AM251 (10 μM) for 1 hour followed by addition of T1117 (0.1 μM). As illustrated in FIG. 9, T1117 uptake was dramatically reduced in cells treated with MNF or AM251 prior to T1117 as compared to either vehicle or fenoterol. These studies indicate that the MNF is capable of modulating GPR55.

Example 4

In Vitro Metabolic Stability of MNF

This example describes the metabolic stability of MNF on human and rat liver microsomes.

Figure 10:
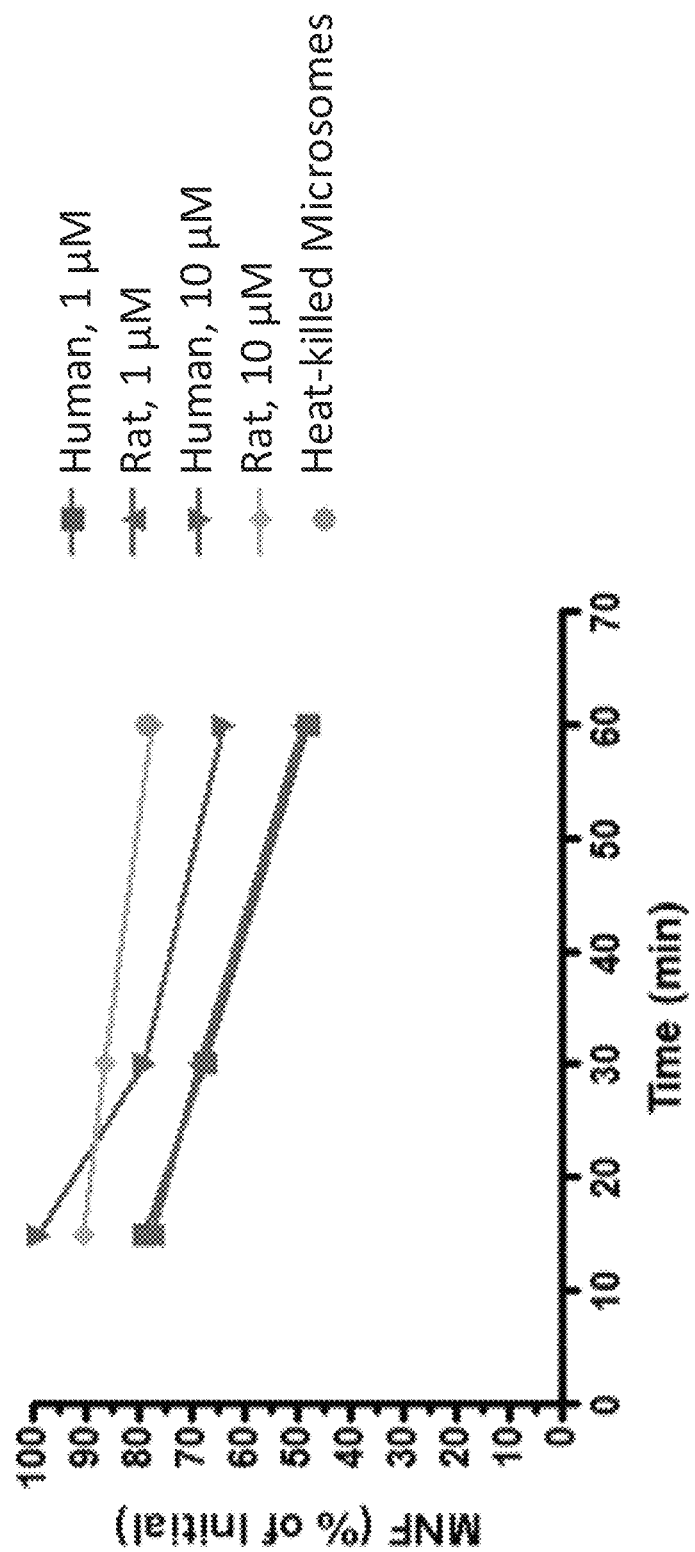
FIG. 10 is a graph illustrating metabolic stability of (R,R')-MNF on human and rat liver microsomes.

FIG. 10 presents the data from the in vitro metabolic stability study in which MNF was incubated (in duplicate) with active and heat-inactivated human (HLM) and rat (RLM) liver microsomes and cofactors at 37° C. Aliquots were removed at 0, 15, 30 and 60 minutes and the amount of test compound (MNF) remaining at each time point was determined by LC-MS/MS. Although the results indicated that MNF is somewhat unstable under the incubation conditions, based on the decrease in concentration in the heat-inactivated microsome controls, the results show a greater decrease in MNF levels when incubated with rat and human liver microsomes.

Figure 11:
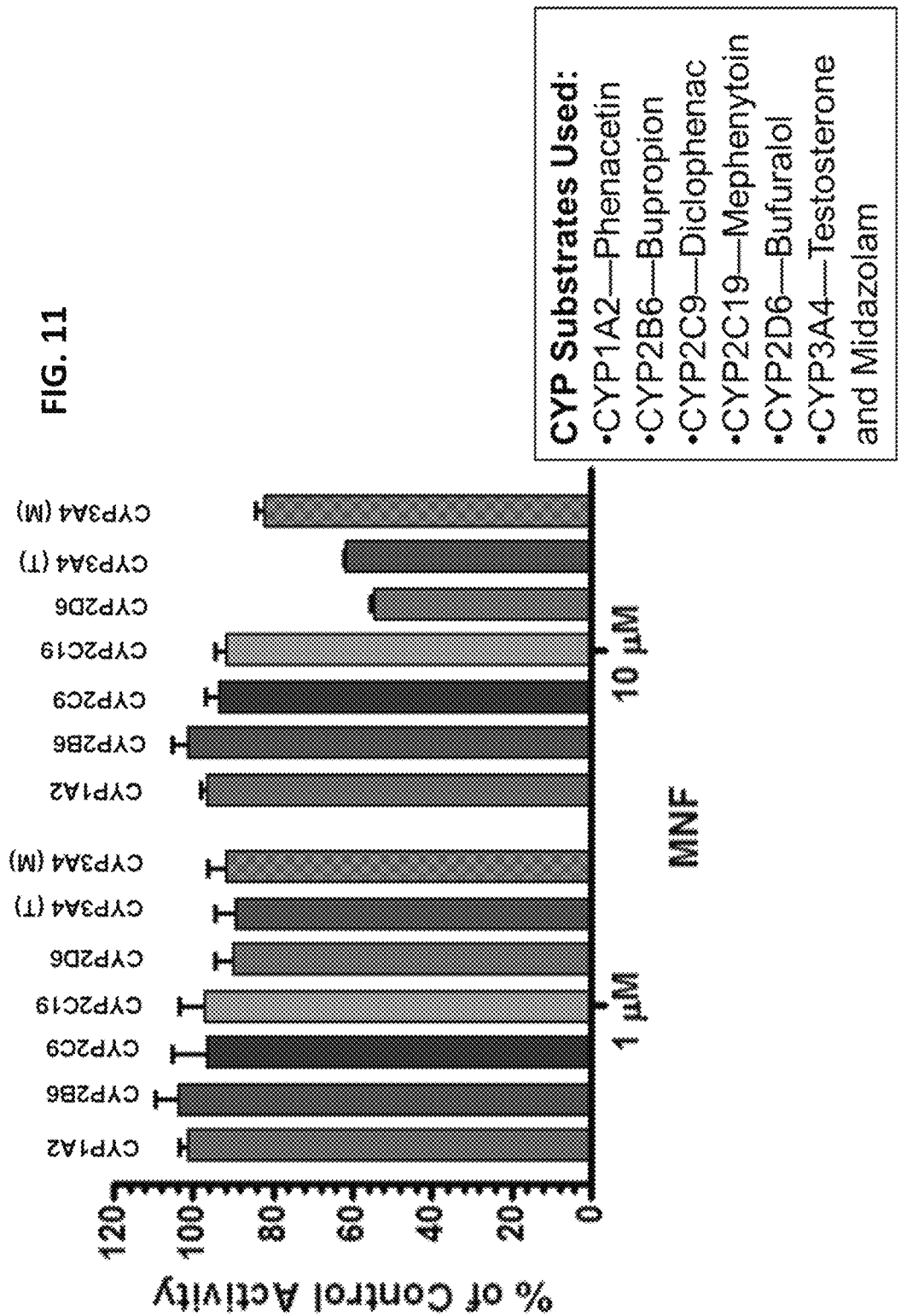
FIG. 11 is a bar graph illustrating cytochrome p450 (CYP) inhibition by (R,R')-MNF. Human liver microsomes were incubated with 8 different CYP substrates and 1 or 10 μM MNF. MNF at 10 μM was determined to inhibit CYP2D6 and CYP3A4. The primary metabolite was determined to be O-demethylated-MNF.

FIG. 11 demonstrates the results from the co-incubation of MNF, 1 or 10 μM, with a cocktail of model CYP substrates, human liver microsomes and CYP cofactors for 20 minutes at 37° C. Incubations containing known CYP inhibitors were also included as positive controls. Formation of the model substrate metabolites was measured by LC-MS/MS and compared to control incubations (incubation of substrates with microsomes and cofactors, no test articles or inhibitors). CYP activity in presence of test compound (MNF) that was less than 70% of control was considered significant. MNF (10 μM) inhibited CYP2D6 and CYP3A4 to less than 70% of the control. Further, the primary metabolite was determined to be O-demethylated-MNF. These studies indicate that MNF alters the metabolism of other drugs or endogenous compounds that are substrates for CYP2D6 and/or CYP3A4 isoforms, when present in the plasma or liver at 10 μM or higher.

Example 5

In Vivo Distribution and Clearance after IV Administration

To determine plasma and brain tissue concentrations of MNF, the concentrations of MNF and its metabolites in plasma and brain tissue samples obtained from male Sprague-Dawley rats were determined after administration of a single IV dose of 10 mg/kg of MNF. The assays were conducted using an Eclipse XDB-$C_{18}$ guard column (4.6 mm×12.5 mm) and an Atlantis HILIC column (150×2.1 mm ID, 5 mm). The mobile phase consisted of water containing 0.1% formic acid as Component A and acetonitrile as component B. A linear gradient was run as follows: 0 minutes 95% B; 5 minutes 60% B; 6 minutes 80% B; 10 minutes 95% B at a flow rate of 1.0 ml/minutes. The total run time was 15 minutes per sample. Identification and quantification of the analytes was accomplished using an API-4000 LC-MS/MS in positive electrospray ionization mode and data was acquired employing multiple reaction monitoring (MRM) and the following MRM transitions: MNF (369-200); MNF-Gluc (545-200).

Figure 12:
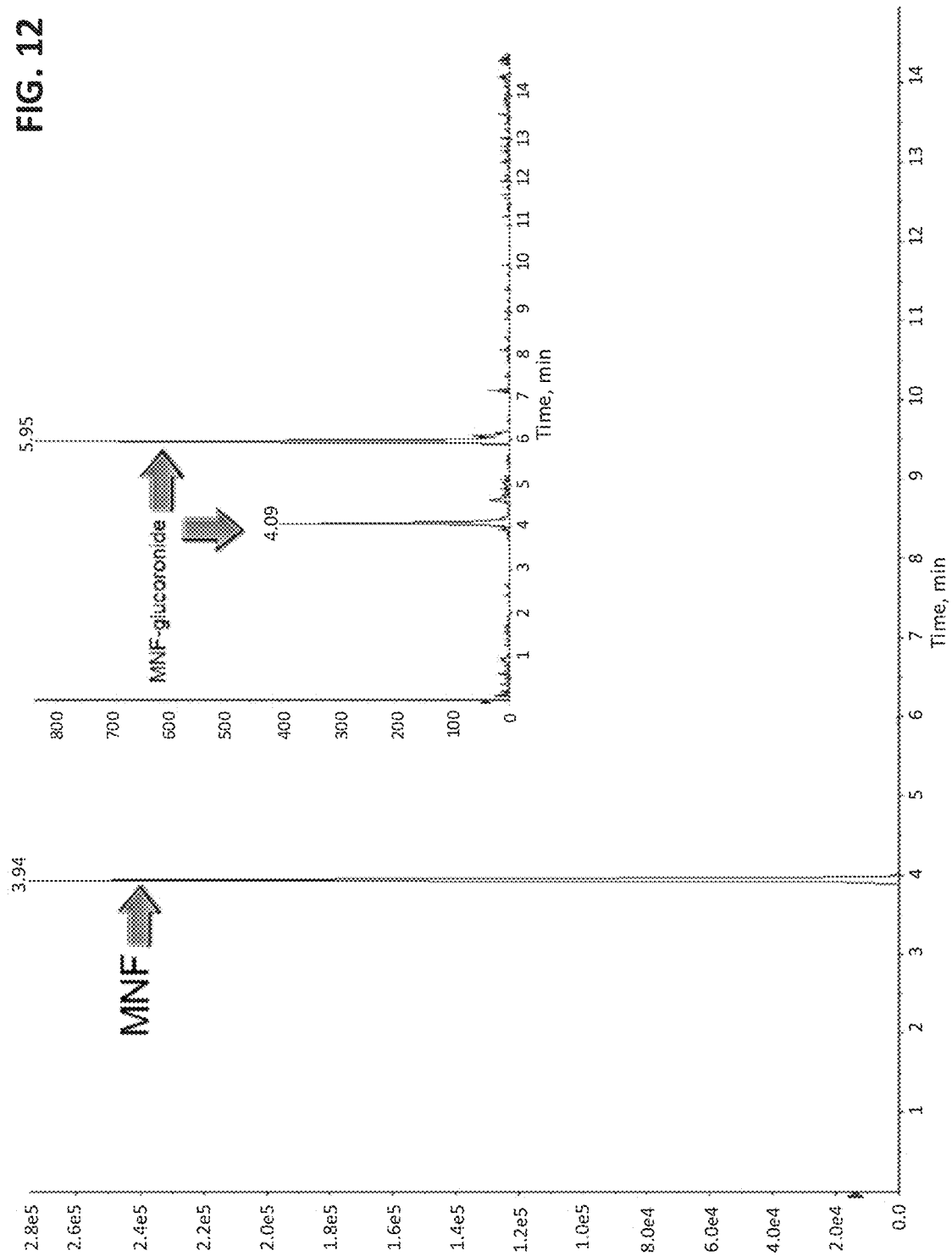
FIGS. 12 and 13 are tracings illustrating plasma and brain tissue concentrations of (R,R')-MNF.
Figure 13:
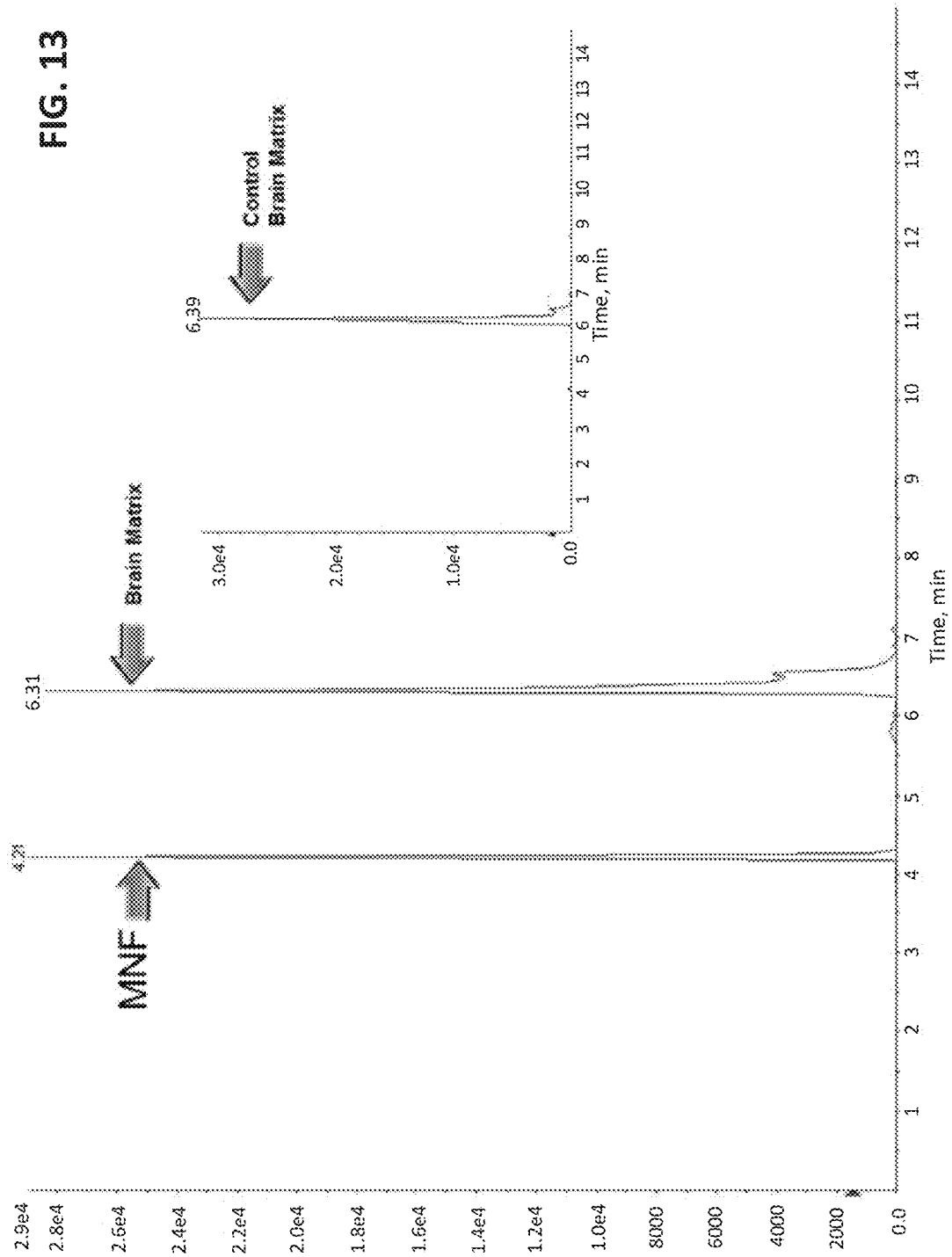
Figure 14:
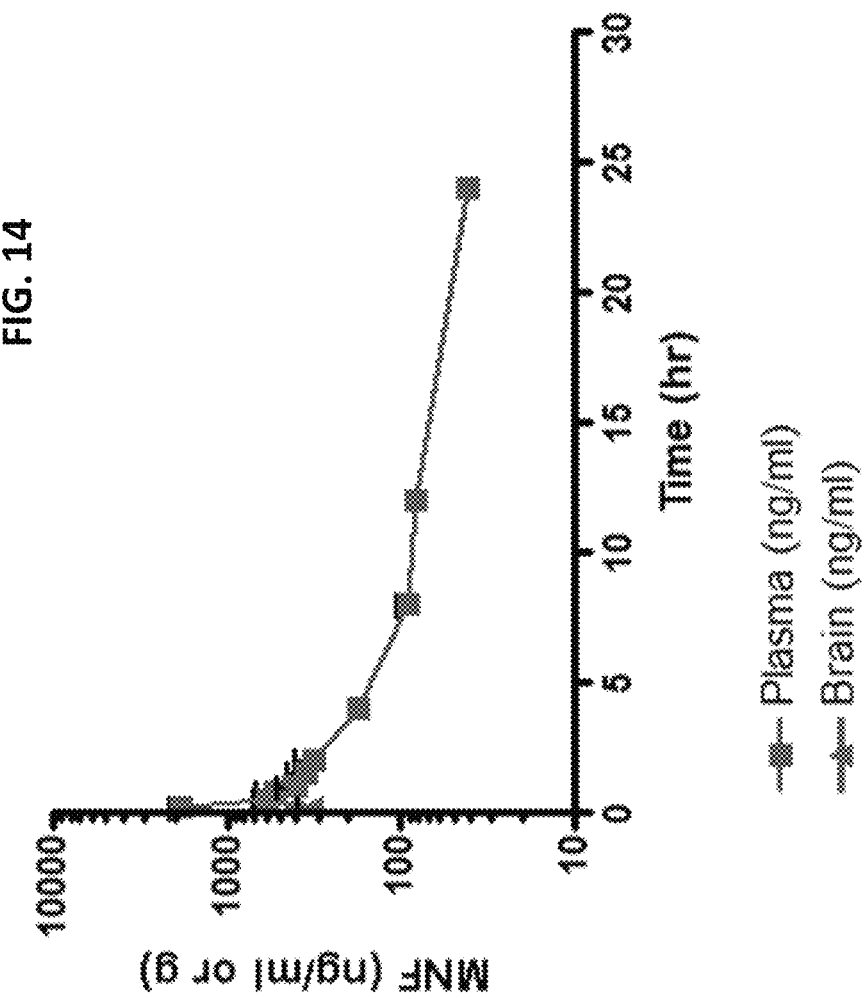
FIG. 14 is a MNF concentration-time course in plasma and brain of male Sprague-Dawley rats after IV administration of 10 mg/kg MNF IV where n=3 rats per time point (10 minutes to 24 hours in plasma and 10 to 60 minutes in the brain). The MNF concentration in brain tissue was 200 ng/mg tissue at 10 minutes after administration and peaked at 30 minutes at 800 ng/mg tissue. The relative distribution between the concentration of MNF in blood (measured as ng/ml) and brain tissue (measured as ng/mg tissue) was 0.2 at 10 minutes and 1.0 at 30 minutes and 60 minutes reflecting an equivalent distribution between both the central and peripheral body compartments.

FIG. 12 illustrates the analysis of a plasma sample obtained 30 minutes post-IV administration of 10 mg/kg MNF. In the insert of FIG. 12, MNF and Gluc-MNF are shown with no interfering peaks being present in the control plasma matrix. FIG. 13 illustrates the analysis of brain tissue obtained 30 minutes post-IV administration of 10 mg/kg MNF. The peak at 6.39 minutes is an unidentified compound present in control brain matrix (see insert of FIG. 13). FIG. 14 is a MNF time-course in plasma and brain of Sprague-Dawley male rats and the calculated pharmacokinetic parameters are presented in Table 3 below.

TABLE 3

Calculated pharmacokinetic parameters for MNF time-course in plasma and brain.

| Rat | $t_{1/2}$ (hr) | $C_{max}$ (ng/ml) | $C^0$ (ng/ml) | $AUC_{last}$ (hr · ng/ml) | $AUC_{inf}$ (hr · ng/ml) | V (l/kg) | Cl (ml/hr/kg) |
|---|---|---|---|---|---|---|---|
| 1 | 9.8 | 1780.7 | 3033.4 | 3582.2 | 4103.6 | 34.3 | 2436.9 |
| 2 | 18.6 | 2304.9 | 4131.4 | 4070.7 | 5335.2 | 50.4 | 1874.4 |
| 3 | 13.0 | 1383.4 | 2340.7 | 2905.1 | 3695.2 | 50.6 | 2706.2 |
| Mean | 13.8 | 1823.0 | 3168.5 | 3519.3 | 4378.0 | 45.1 | 2339.1 |
| SD | 4.5 | 462.2 | 903.0 | 585.3 | 853.7 | 9.4 | 424.5 |

Abbreviations
Elimination phase half life = $t_{1/2}$;
maximum plasma concentration observed = $C_{max}$;
plasma concentration extrapolated to time 0 = $C^0$;
area under the plasma versus time curve to last time point and extrapolated to infinity = $AUC_{last}$, $AUC_{inf}$;
apparent volume of distribution = V;
whole body clearance = Cl.

Ten mg/kg MNF was administered IV to male Sprague-Dawley rats and the plasma concentrations of MNF were determined between 10 minutes and 24 hours post administration with the levels measured in 3 animals per time point. In the same study, the concentration of MNF in brain tissue was measured between 10 and 60 minutes after administration with 3 animals per time point. The MNF concentration in brain tissue was 200 ng/mg tissue at 10 minutes after administration and peaked at 30 minutes at 800 ng/mg tissue. The relative distribution between the concentration of MNF in blood (measured as ng/ml) and brain tissue (measured as ng/mg tissue) was 0.2 at 10 minutes and 1.0 at 30 minutes and 60 minutes reflecting an equivalent distribution between both the central and peripheral body compartments. This analysis indicates that significant levels of the drug can be quantified in the brain tissue 10 minutes after administration and that the concentration peaks at 30 minutes after dosing, at which time it parallels the plasma concentration and that at 60 minutes, the brain tissue concentration continues to parallel the plasma concentration. Further, the apparent volume of distribution (V) is high indicating extensive tissue distribution.

These studies demonstrate that MNF is capable of passing through the blood brain barrier and that administration of such compound as well as likely other related fenoterol analogues and/or fenoterol by IV is an effective means of delivering these compounds to the brain, such as to treat a brain tumor regulated by CB receptor activity.

Example 6

MNF has No Significant Negative Effects on Central Nervous System Function

This example demonstrates that MNF has no significant negative effects on central nervous system function.

A single dose escalation study was performed to select dose levels for 7-day repeat dose study with IV administration in Sprague-Dawley rats. Dose levels were 0, 5, 10 and 25 mg/kg. Toxic effects were minimal in this study (see Tables 4 and 5 below).

TABLE 4

7-Day Repeat Dose Range Finding Study of MNF in Sprague-Dawley rats. Endpoints:
body weight change; clinical observations; clinical pathology; gross necropsy; and histopathology.

| Test Article | Vehicle | Dose Level (mg/kg) | Dose Volume (ml/kg) | Dose Concentration[b] (mg/ml) | Number of Animals Main Groups[a] | Number of Animals Recovery Groups[a] |
|---|---|---|---|---|---|---|
| MNF | 0.9% Sodium Chloride for Injection, USP | 0 | 5 | 0 | 3M/3F | 3M/3F |
| SRI-12838 | 0.9% Sodium Chloride for Injection, USP | 2.5 | 5 | 0.5 | 3M/3F | 3M/3F |
| SRI-12838 | 0.9% Sodium Chlorirde for Injection, USP | 10 | 5 | 2 | 3M/3F | 3M/3F |
| SRI-12838 | 0.9% Sodium Chloride for Injection, USP | 25 | 5 | 5 | 3M/3F | 3M/3F |

TABLE 5

Evaluation of MNF study shown in Table 4.

| Species/ Strain | Sutdy Design[a] | Body Weight[b] | Clinical Observation[c] | Clinical Pathology[d] | Gross Necropsy Observation[e] | Histo- pathology |
|---|---|---|---|---|---|---|
| Rat/ Sprague Dawley | Escalation: 0, 2.5, 5, 10, or 25 mg/kg 7-Day: 0, 5, 10, or 25 mg/kg/day | Body weight for treated rats was comparable with control animals | Slight hypoactivity: all treated rats post dose Necrosis: high-dose | Increases: ~2-fold WBC, % Neut. % RET/REA, and PLC | Discolored red: thymus, mandibular lymph node Discolored black or necrosis: tail | Evaluation in progress |

[a]Dosing regimen (5 ml/kg in 0.9% saline): single intravenous (iv) injection via the lateral tail vein (escalation study); single daily iv dose with a 7 day recovery period (7-day study)
[b]Body weight collected: Day 1 for escalation dose calculation; Day 1, Day 3, and Day 8 (Main and Recovery) and Day 14 (Recovery) for 7-day repeat study.
[c]Observations seen during 7-Day repeat study: performed daily; hypoactivity observed ~5 minutes post-dose and subsided ~1 hour post-dose; necrosis observed at injection site for males and females.
[d]Hematology and clinical chemistry evaluations performed Day 8 and Day 14; increases seen in high-dose males and females at interim and terminal sacrifice appear to be associated with necrosis at dose site.
[e]Observations seen at interim (Day 8) and terminal (Day 14) time points.

Figure 15:
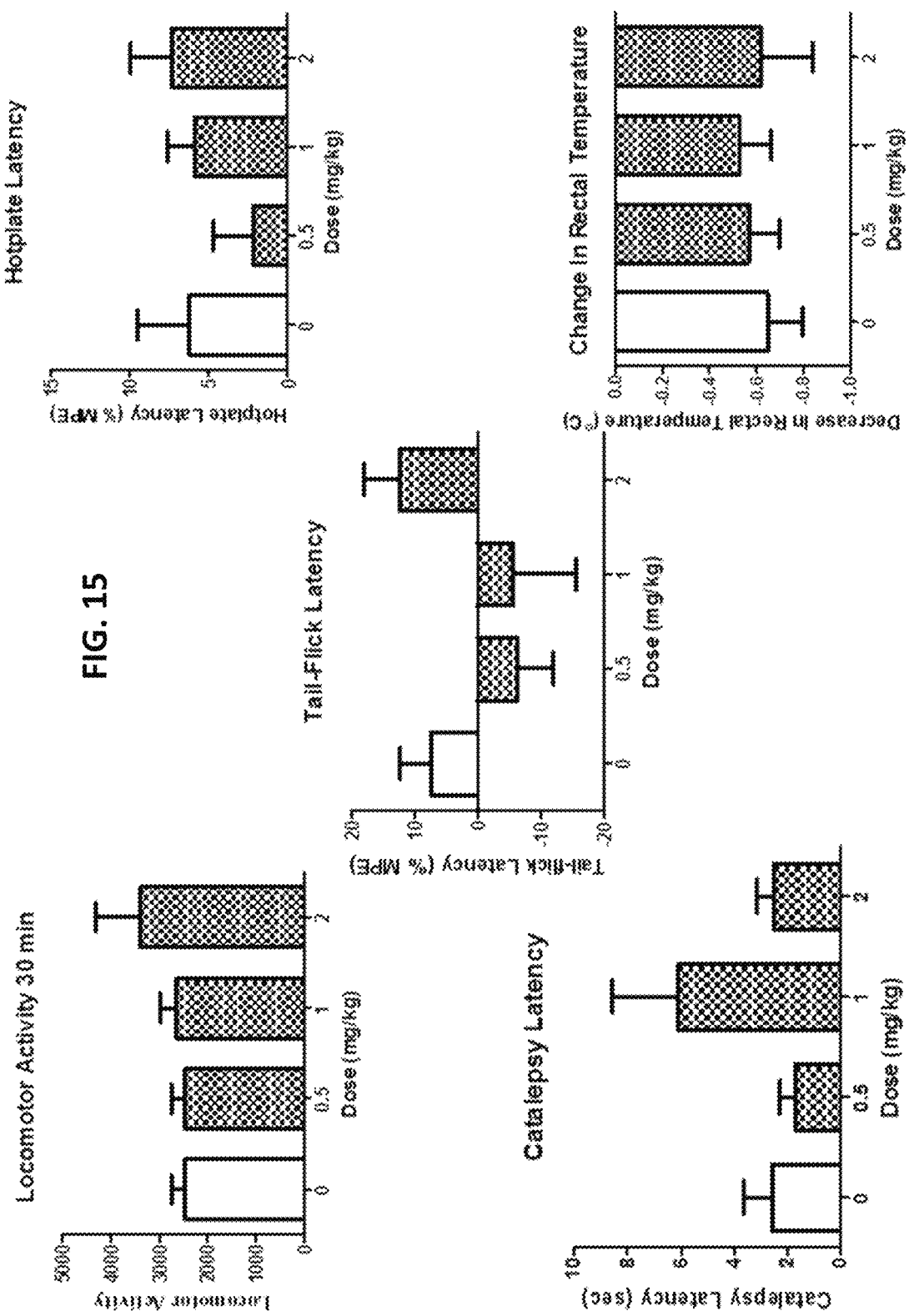
FIG. 15 is a series of bar graphs illustrating that MNF does not produce significant negative effects on the central nervous system relative to the effects produced by tetrahydrocannabinol (presented in FIG. 16).
Figure 16:
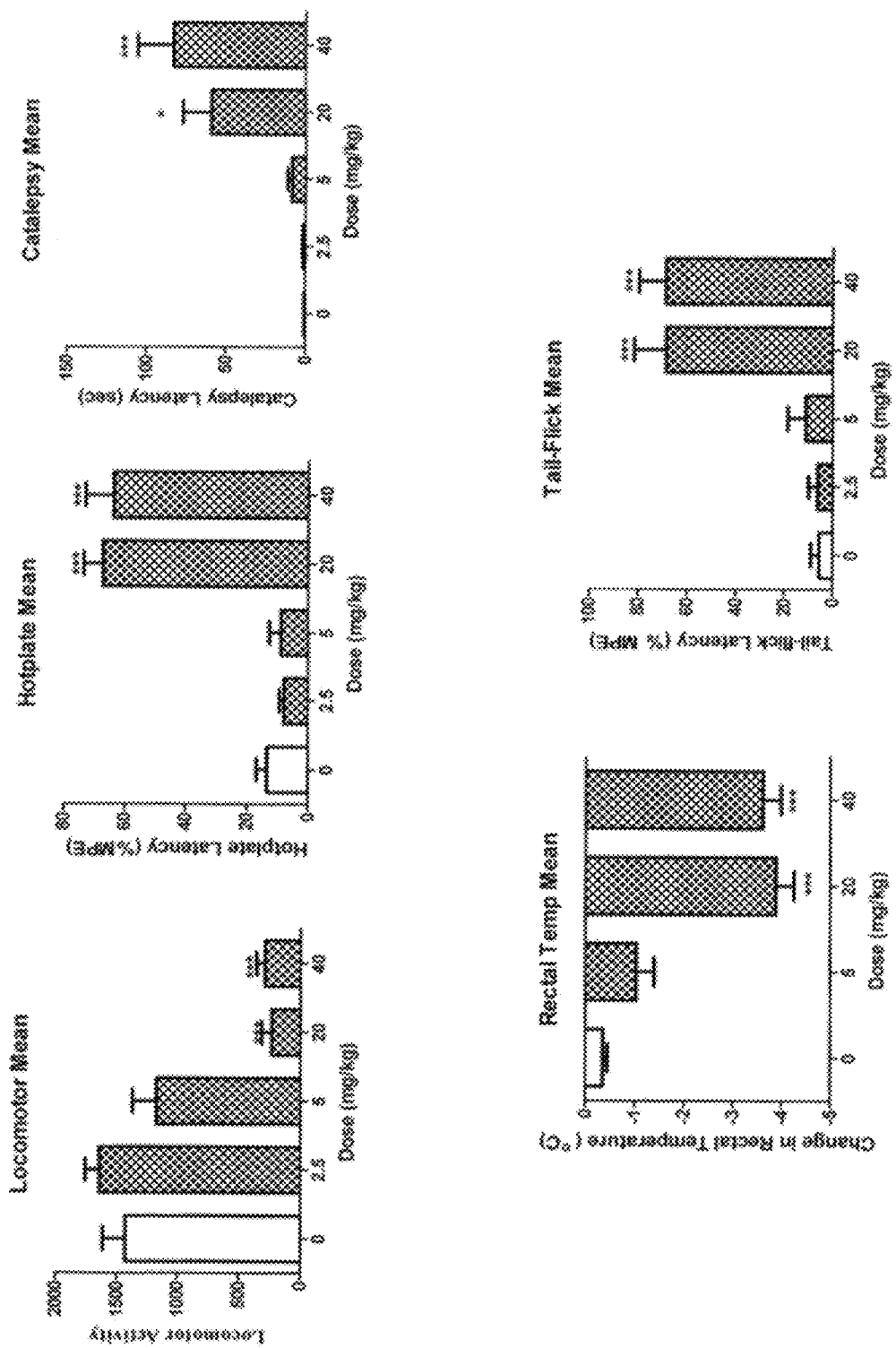
FIG. 16 is a series of bar graphs illustrating the effects of tetrahydrocannabinol on central nervous system function.
Figure 17:
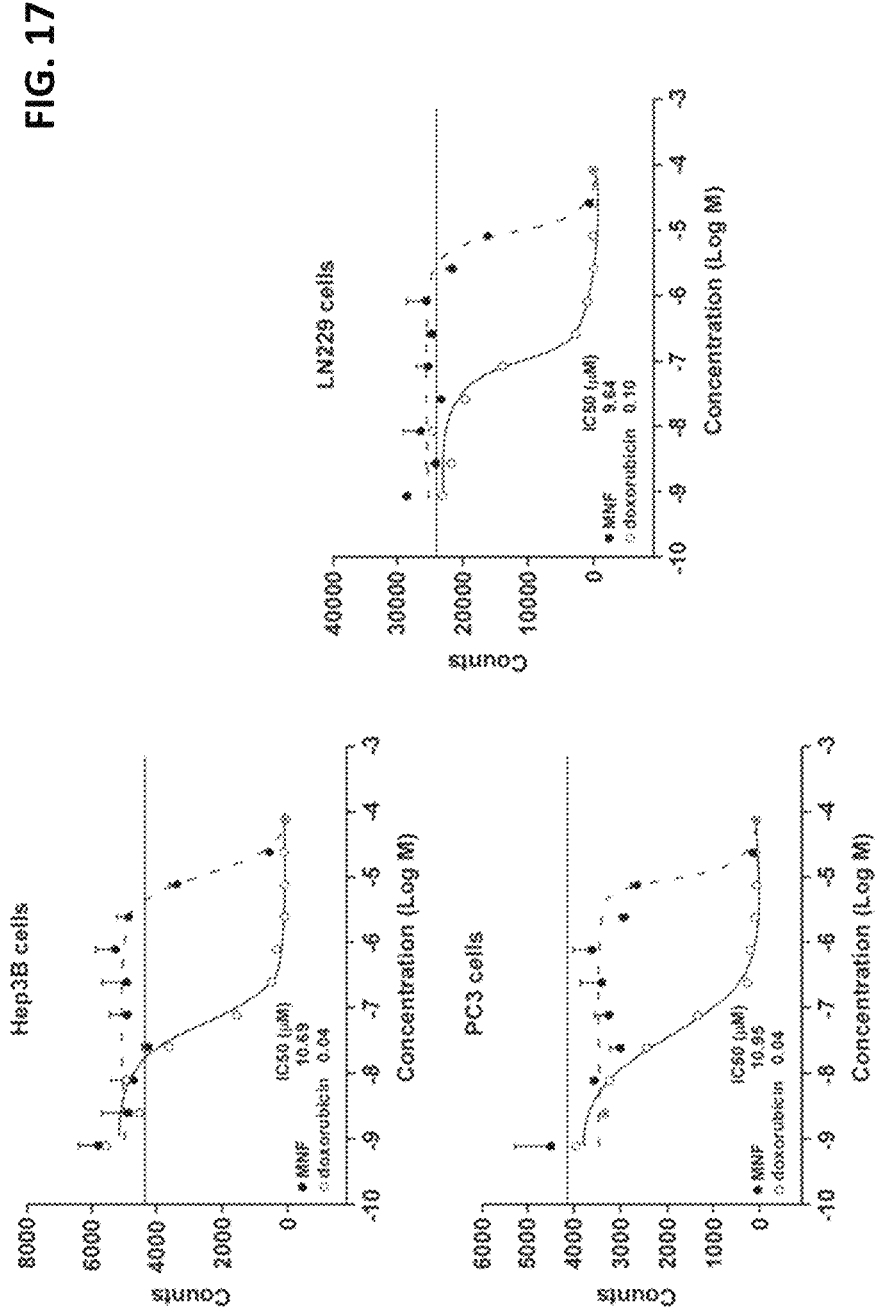
FIG. 17 is a series of graphs illustrating [3H]-Thymidine incorporation in 96-well culture plates including Hep3B cells, PC3 cells or LN229 cells.

Additional studies were performed which further evaluated the effect of MNF on central nervous system functions. In these studies, MNF was found to not have any significant negative effects on the central nervous system (FIG. 15) as compared to tetrahydrocannabinol (FIG. 16).

Example 7

(R,R')-MNF and (R,R')-4-methoxyfenoterol (MF) are Potent Inhibitors of Liver, Colon and Lung Cancer Cell Growth This example demonstrates that (R,R')-MNF and (R,R')-4-methoxyfenoterol (MF) are potent inhibitors of liver, colon, and lung cancer cell growth.

The effect of (R,R')-MF and (R,R')-MNF on the growth of a variety of tumor cells was evaluated. An $IC_{50}$ value of less than 30 µM was considered to be an effective inhibitor of tumor cell growth whereas an $IC_{50}$ value of less than 50 µM indicates potential activity. As illustrated in Tables 6 and 7 below, MNF was a potent inhibitor of liver cancer cell growth, lung cancer cell growth, colon cancer cell growth, prostate cancer cell growth, CNS cancer cell growth, and non-small cell lung cancer (NSCLC).

These studies indicate that MNF and MF are capable of inhibiting additional types of cancer growth, including liver, lung and colon cancer. One of skill in the art will appreciate that they also provide support for using other fenoterol analogues (such as other naphthylfenoterol analogues), to reduce tumor growth, including treating cancer, such as liver, lung and colon cancer, in additional subjects, including humans.

TABLE 6

Effect of MNF and MF on various tumor cells.

| | # | Type | Name | seeding n/well | In vivo imaging | IC50 (uM) RR-MF | IC50 (uM) RR-MNF | Doxorubicin | T3 % CV | T3/T0 |
|---|---|---|---|---|---|---|---|---|---|---|
| None CNS added | 1 | Pancreatic C | CAPAN | 750 | | N.E. | Not Regress. | 0.23 | 5.16 | 1.71 |
| | 2 | Pancreatic C | PANC-1 | 1125 | | N.E. | 33.38 | 2.97 | 12.69 | 1.73 |
| | 3 | Liver C | HEPG2 | 750 | Caliperls | N.E. | 28.82 | 0.28 | 7.68 | 3.11 |
| | 4 | Liver C | HEP3B | 750 | | >50 uM | 14.71 | 0.43 | 4.55 | 2.42 |

TABLE 6-continued

Effect of MNF and MF on various tumor cells.

|  | # | Type | Name | seeding n/well | In vivo imaging | RR-MF IC50 (uM) | RR-MNF IC50 (uM) | Doxorubicin IC50 (uM) | T3 % CV | T3/T0 |
|---|---|---|---|---|---|---|---|---|---|---|
| NCI60 Subpanel | 5 | Prostate C | Du-145 | 750 |  | >50 uM | 34.76 | 0.38 | 3.34 | 4.39 |
|  | 6 | Prostate C | PC3 | 1125 |  | >50 uM | 28.06 | 0.91 | 2.18 | 4.08 |
|  | 7 | Breast C | MCF7 | 2250 |  | N.E. | 37.19 | 0.30 | 3.23 | 2.51 |
|  | 8 | Breast C | MDAMB231 | 1500 | SRI stock | N.E. | 33.23 | 0.68 | 3.28 | 3.94 |
|  | 9 | NSCLC | H460 | 750 |  | >50 uM | 11.59 | 0.02 | 2.90 | 12.78 |
|  | 10 | NSCLC | A549 | 750 |  | >50 uM | 23.14 | 0.11 | 3.27 | 7.96 |
|  | 11 | Colon C | HT29 | 375 |  | >50 uM | 10.71 | 0.26 | 5.85 | 12.46 |
|  | 12 | Colon C | HCT116 | 375 |  | >50 uM | 12.91 | 0.06 | 5.75 | 10.87 |
|  | 13 | CNS | U251 | 375 |  | N.E. | 26.67 | 0.17 | 2.48 | 4.47 |
| CNS Panel | 14 | CNS | U87 | 1125 | Caliperls | N.E. | 25.72 | 0.21 | 10.16 | 3.71 |
|  | 15 | CNS | GL261 | 375 | Caliperls | N.E.? | 21.32 | 0.17 | 7.54 | 4.61 |
|  | 16 | CNS | LN-18 | 1125 |  | N.E.? | 29.74 | 0.53 | 2.76 | 6.25 |
|  | 17 | CNS | A172 | 750 | ? | N.E.? | 30.48 | 0.46 | 5.08 | 2.77 |
|  | 18 | CNS | LN-229 | 750 | ? | >50 uM | 26.77 | 0.61 | 2.23 | 3.90 |
|  | 19 | CNS | U118 | 1125 | ? | >50 uM | 37.04 | 0.81 | 2.66 | 2.43 |
|  | 20 | CNS | 1321N | 1125 | ? | TBD | TBD | TBD | TBD | TBD |

TABLE 7

Effect of MNF and MF on various tumor cells.

| Name | seeding n/well | RR-MF IC50 (uM) | RR-MNF IC50 (uM) | Doxorubicin IC50 (uM) | Vc CV | Tr/Tz[a] | Note |
|---|---|---|---|---|---|---|---|
| HEP3B (Liver Cancer) | 750 | >50 uM | 14.71 | 0.43 | 4.55 | 2.42 | 384well CTG 3 days treatment −1 |
|  |  | >50 uM | 12.14 | 0.35 | 8.65 | 2.22 | 384well CTG 3 days treatment −2 |
|  | 4275 | >50 uM | 13.53 | 0.52 | 6.56 | 1.74 | 96 well CTG 2 days treatment |
|  |  | 2.35 | 10.03 | 0.02 | 13.38 | NA[b] | 96 well Thy 2 days treatment |
|  |  | >50 uM | 28.30 | NF[c] | 4.40 | 1.19 | 96 well CTG 1 day treatment |
|  |  | 2.40 | 10.69 | 0.04 | 14.66 | NA[b] | 96 well Tye 1 day treatment |
| PC3 (Prostate Cancer) | 1125 | >50 uM | 28.06 | 0.91 | 2.18 | 4.08 | 384well CTG 3 days treatment −1 |
|  | 5412.5 | >50 uM | 20.36 | 0.93 | 3.10 | 5.89 | 96 well CTG 2 days treatment |
|  |  | >50 uM | 10.84 | 0.28 | 13.74 | NA[b] | 96 well Thy 2 days treatment |
|  |  | >50 uM | 34.51 | 3.02 | 4.52 | 2.66 | 96 well CTG 1 day treatment |
|  |  | >50 uM | 10.95 | 0.04 | 9.16 | NA[b] | 96 well Tye 1 day treatment |
| NCIH460 (NSCLC) | 750 | >50 uM | 11.59 | 0.02 | 2.90 | 12.78 | 384well CTG 3 days treatment −1 |
|  |  | >50 uM | 17.68 | 0.11 | 3.10 | 9.71 | 384well CTG 3 days treatment −2 |
|  | 4275 | >50 uM | 15.40 | 0.12 | 7.82 | 5.26 | 96 well CTG 2 days treatment |
|  |  | >50 uM | 21.03 | 0.03 | 17.96 | NA[b] | 96 well Thy 2 days treatment |
|  |  | >50 uM | 38.92 | 0.31 | 3.10 | 1.30 | 96 well CTG 1 day treatment |
|  |  | >50 uM | 25.08 | 0.09 | 16.10 | NA[b] | 96 well Tye 1 day treatment |
| HCT116 (Colon Cancer) | 375 | >50 uM | 12.91 | 0.06 | 5.75 | 10.87 | 384well CTG 3 days treatment −1 |
|  |  | >50 uM | 12.20 | 0.21 | 5.39 | 13.13 | 384well CTG 3 days treatment −2 |
|  | 2137.5 | >50 uM | 10.54 | 0.23 | 6.01 | 8.30 | 96 well CTG 2 days treatment |
|  |  | >50 uM | 10.97 | 0.14 | 6.79 | NA[b] | 96 well Thy 2 days treatment |
|  |  | >50 uM | 18.96 | 0.21 | 5.34 | 2.15 | 96 well CTG 1 day treatment |
|  |  | >50 uM | 23.75 | 0.12 | 9.90 | NA[b] | 96 well Tye 1 day treatment |
| HT29 (Colon Cancer) | 375 | >50 uM | 10.71 | 0.26 | 5.85 | 12.46 | 384well CTG 3 days treatment −1 |
|  | 2137.5 | >50 uM | 11.65 | 0.52 | 8.63 | 6.11 | 96 well CTG 2 days treatment |
|  |  | >50 uM | 19.57 | 0.12 | 44.53 | NA[b] | 96 well Thy 2 days treatment |
|  |  | >50 uM | 30.40 | NF[c] | 3.84 | 1.56 | 96 well CTG 1 day treatment |
|  |  | >50 uM | 12.98 | 0.11 | 17.05 | NA[b] | 96 well Tye 1 day treatment |
| LN229 (CNS Cancer) | 750 | >50 uM | 26.77 | 0.61 | 2.23 | 3.90 | 384well CTG 3 days treatment −1 |
|  | 4275 | >50 uM | 15.69 | 1.70 | 1.80 | 2.20 | 96 well CTG 2 days treatment |
|  |  | >50 uM | 10.37 | 0.07 | 12.20 | NA[b] | 96 well Thy 2 days treatment |
|  |  | >50 uM | 29.32 | NF[c] | 2.70 | 1.37 | 96 well CTG 1 day treatment |
|  |  | >50 uM | 9.64 | 0.10 | 12.09 | NA[b] | 96 well Tye 1 day treatment |

VcCV Percent Variance of control wells on day of reading
Tr/Tz[a] cell growth measured by comparing control wells before and after compound treatment;
NA[b] not applicable
NF[c] no optimum fitting

Example 8

Antitumor Activity of (R,R')-4-methoxy-1-naphthylfenoterol in a Rat C6 Glioma Xenograft Model in the Mouse This example demonstrates antitumor activity of MNF in a rat C6 glioma xenograft model in the mouse.

(R,R')-4-methoxy-1-naphthylfenoterol (MNF) inhibits in vitro proliferation of several types of cancer cell lines. In this example, the in vivo antitumor effects of MNF were evaluated using rat C6 glioma cells implanted subcutaneously into the lower flank of 5 week-old NMRI/Nude female Swiss mice. Three days after the inoculation, the mice were subjected to intraperitoneal injections of saline or MNF (2 mg/kg) for five days per week for two weeks. Tumor volumes were measured everyday using slide calipers. At the end of the study, animals were sacrificed and tumors were collected for cDNA microarray, quantitative RT-PCR and immunoblot analyses. Significant reduction in mean tumor volumes was observed in mice receiving MNF when compared with the saline-treated group ($p<0.001$, $n=17-19$). Clusters in expression of genes involved in cellular proliferation were identified, as well as molecular markers for glioblastoma that were significantly downregulated in tumors of MNF-treated mice as compared to saline-injected controls. The efficacy of MNF against C6 glioma cell proliferation in vivo and in vitro was accompanied by marked reduction in the expression of cell cycle regulator proteins. This study is the first demonstration of MNF-dependent chemoprevention in a glioblastoma xenograft model and provides a mechanism for its anticancer action in vivo.

Materials and Methods

Materials. (R,R')-4-methoxy-1-naphthylfenoterol (MNF) was synthesized as described herein and previously (Jozwiak et al., *J Med Chem* 50:2903-2915, 2007; Jozwiak et al., Bioorg Med Chem 18:728-736, 2010; each of which is incorporated by reference in its entirety). Dulbecco's modified Eagle Medium (DMEM), trypsin solution, phosphate-buffered saline (PBS), fetal bovine serum (FBS), 100× solution of L-glutamine (200 mM), and penicillin/streptomycin (a mixture of 10,000 units/ml penicillin and 10,000 µg/ml streptomycin) were obtained from Quality Biological (Gaithersburg, Md., USA).

Cell culture. The rat-derived C6 glioma cell line was obtained from the American Type Culture Collection (Manassas, Va.). The cells were routinely maintained in DMEM supplemented with L-glutamine, 1% penicillin/streptomycin solution, and 10% FBS in a humidified $CO_2$ incubator at 37° C.

3H-Thymidine incorporation. C6 glioma cells were seeded in 12-well plates at ~5×104 cells/well and incubated for 24 hours followed by a second 24-hour incubation with various concentrations of MNF. Radiolabeled thymidine (10 Ci/mmol; PerkinElmer Life and Analytical Sciences, Waltham, Mass.) was added at 1 µCi per well for 16 hours and its incorporation into DNA was then measured. Each treatment group was performed in triplicate and three independent studies were carried out.

C6 tumor xenograft in mice. In order to assess the ability of MNF to induce regression of tumor growth in vivo, rat C6 glioma cells were trypsin-collected at confluency and were used to generate tumor xenografts. Athymic female nude mice (SWISS nu+/nu+) were obtained from Charles Rivers (L'Arbresle, France) and maintained under pathogen-free conditions with a 12 hours light/12 hours dark cycle. Animals were fed ad libitum with normal chow (supplier). Athymic nude mice were inoculated subcutaneously with 1000 of culture medium containing 0.5×106 C6 glioma cells in the left flank and then were randomly divided into two groups of 10 animals each. Starting 3 days after cell inoculation, mice received daily intraperitoneal injection (10 µl·g-1 body weight) of vehicle or MNF (2 mg·kg-1) in 100 µM ascorbic acid in saline (vehicle) five days a week for 19 days. Animal survival was monitored daily, and tumor size was determined with the use of a caliper to measure the length (a) and width (b) and estimated as $4/3\pi \times r1^2 \times r2$, where rl is the smaller and r 2 the larger radius. The mice were monitored up to 19 days after MNF injection or euthanized earlier if the tumor size was superior to 2 cm3 or the mouse was lethargic, sick and unable to feed, which caused the body weight to drop below 20% of initial weight. The mice were euthanized by cervical extension, and tumor masses were removed, weighed and washed with cold PBS before being snap-frozen in liquid nitrogen. A second set of studies with 8-9 animals in both groups was repeated.

Evaluation of MNF accumulation in vivo in C6 glioma tumors. The accumulation of MNF in vivo in C6 tumor xenografts in athymic mice was assessed in comparison with vehicle-treated tumor-bearing animals. The frozen tumor samples were thawed, and then homogenized. The concentration of MNF and its metabolites was determined by HPLC followed by LC-MS/MS. In brief, the assays were conducted using an Eclipse XDB-C18 guard column (4.6 mm×12.5 mm) and an Atlantis HILIC column (150×2.1 mm ID, 5 mm). The mobile phase consisted of water containing 0.1% formic acid as component A and acetonitrile as component B. A linear gradient was run as follows: 0 minutes 95% B; 5 minutes 60% B; 6 minutes 80% B; 10 minutes 95% B at a flow rate of 1.0 ml/minute. The total run time was 15 minutes per sample. Identification and quantification of the analytes was accomplished using an API-4000 LC-MS/MS in positive electrospray ionization mode and data was acquired employing multiple reaction monitoring (MRM) and the following MRM transitions: MNF (369-200); MNF-Gluc (545-200). Tumor tissues from vehicle-injected mice were used as controls.

Analysis of gene expression in rat C6 glioma xenografts. Total RNA was isolated from rat C6 glioma xenografts harvested from vehicle and MNF-treated mice (n=3 per group, cohort 1). This analysis was repeated in a second cohort of animals (n=3 per group, cohort 2). Total cellular RNA was extracted using an RNeasy plus mini kit (QIAGEN, Valencia, Calif.), and its quality was assessed using an Agilent BioAnalyzer using RNA 6000 Nano Chips (Agilent Technologies, Santa Clara, Calif.). Transcriptional profiling was determined using Illumina Sentrix BeadChips (Illumina, San Diego, Calif.). Total RNA was used to generate biotin-labeled cRNA with the Illumina TotalPrep RNA Amplification Kit. In short, 0.5 ug of total RNA was first converted into single-stranded cDNA with reverse transcriptase using an oligo-dT primer containing the T7 RNA polymerase promoter site and then copied to produce double-stranded cDNA molecules. The double-stranded cDNA was cleaned and concentrated with the supplied columns and used in an overnight in-vitro transcription reaction where single-stranded RNA (cRNA) was generated incorporating biotin-16-UTP. A total of 0.75 µg of biotin-labeled cRNA was hybridized at 58° C. for 16 hours to Illumina's Sentrix Rat Ref-12 Expression BeadChips. Each BeadChip has ~22,000 well-annotated RefSeq transcripts with approximately 30-fold redundancy. The arrays were washed, blocked and the labeled cRNA was detected by staining with streptavidin-Cy3. Hybridized arrays were scanned using an Illumina BeadStation 500× Genetic Analysis Systems scanner and the image data extracted using Illumina's GenomeStudio software, version 1.6.1. For statistical analysis, the expression data were filtered to include only probes with a consistent signal on each chip and an Illumina detecton p value <0.02.

Correlation analysis, sample clustering analysis and principal component analysis was performed to identify/exclude any possible outliers. The resulting dataset was next analyzed with DIANE 6.0, a spreadsheet-based microarray analysis program using value statistics for Z-Score reliability below 0.05; and mean background-corrected signal intensity greater than zero.

Gene set enrichment analysis use gene expression values or gene expression change values for all of the genes in the microarray. Parametric analysis of gene set enrichment (PAGE) was used using the WEB-PAGE GSA tool for gene set analysis. Gene Sets include the MSIG database, Gene Ontology Database, GAD human disease and mouse phenotype gene sets were used to explore functional level changes. Gene-gene interaction was also analyzed using the INGENUITY® Pathway Analysis (IPA) system (INGENUITY® Systems).

Total RNA extraction, cDNA synthesis and qRT-PCR analysis. Total RNA (including the DNase treatment step) was isolated from frozen tumor tissues using the RNeasy mini kit (Qiagen, Valencia, Calif.). RNA concentration and quality was measured using the NanoDrop spectrophotometer (NanoDrop Technologies, Wilmington, Del.). Subsequently, 2 µg total RNA was reverse-transcribed to cDNA using the qSCRIPT™ cDNA SuperMix (Quanta Biosciences, Gaithersburg, Md.). Quantitative real-time PCR (qRT-PCR) reactions were performed to validate the expression of 6 genes that were selected from the microarray analysis. The reactions were carried out with SYBR® Green PCR master mix on an ABI Prism 7300 sequence detection system (Applied Biosystems) using commercially available target probes for Sox4, Olig1, Galnt3, Cdkn3, Ccna2, and Bub1b (PrimeTime qPCR Assays and Primers, IDT DNA Technologies, Coralville, Iowa). The data was analyzed using the 2-ΔΔCt method with Gapdh and vehicle-treated tumors as internal controls. Controls consisting of reaction mixture without cDNA were negative in all runs.

Western Blot Analysis. Frozen tumor tissues were lysed with radioimmune precipitation buffer containing EGTA and EDTA (Boston BioProducts, Ashland, Mass.) supplemented with a phosphatase inhibitor cocktail (EMB-Calbiochem), and protease inhibitor cocktail (Sigma-Aldrich), according to standard protocols. Equal amounts of protein from the clarified lysates were separated by SDS-polyacrylamide gel electrophoresis under reducing conditions (Invitrogen, Carlsbad, Calif.), and electrotransferred onto polyvinylidene difluoride membranes using the iBlot system (Invitrogen). Western blots were performed according to standard methods, which involved blocking the membrane in 5% non-fat milk, followed by sequential incubation method with the primary antibody of interest and secondary antibody conjugated with the enzyme horseradish peroxidase. The detection of immunoreactive bands was performed by chemiluminescence using the ECL Plus Western Blotting Detection System (GE Healthcare, Piscataway, N.J.). Quantitation of the protein bands was done by volume densitometry using ImageJ software (National Institutes of Health, Bethesda, Md.). Primary antibodies used in this study were raised against cyclin A (sc-751, 1:500 dilution; Santa Cruz Biotechnology, Inc., Santa Cruz, Calif., USA), cyclin D1 (sc-8396; 1:500 dilution; Santa Cruz), and β-actin (mouse; 1:10000 dilution; Abcam, Cambridge, Mass., USA). Detection of Hsp90 with a monoclonal antibody (1:1000; Santa Cruz Biotechnology, Inc., Santa Cruz, Calif.) was carried out to control for equal protein loading.

Statistical Analysis. Western blot data form both sets of tumor tissues were analyzed together. The Shapiro-Wilk test was used to assess if the values (protein expression levels) followed a Gaussian distribution. Outliers were removed from further analysis as they were preventing the population to pass the normality test. The results from rat C6 cells in culture were analyzed using the Student t-test. Repeated two-way analysis of variance (ANOVA) was used to compare induction of changes as a function of time. Data were expressed as means±standard error of the mean (SEM) and were considered significant when the p value was less than 0.05.

Results

Figure 18A:
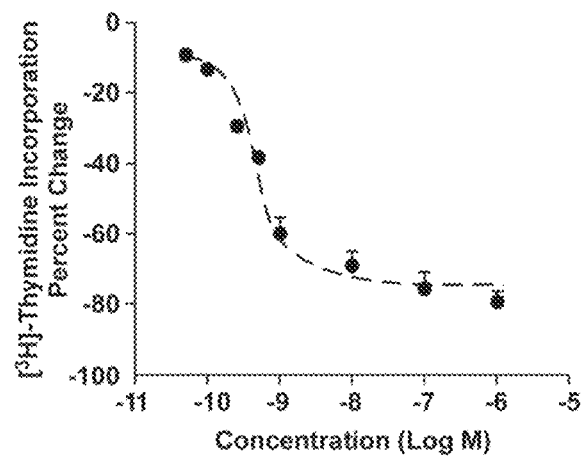
FIGS. 18A, 18B and 18C illustrate MNF reduces proliferation of rat C6 glioma cell line.
Figure 18B:
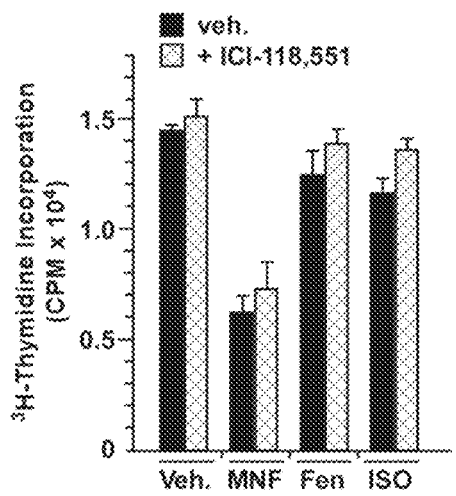
Figure 18C:
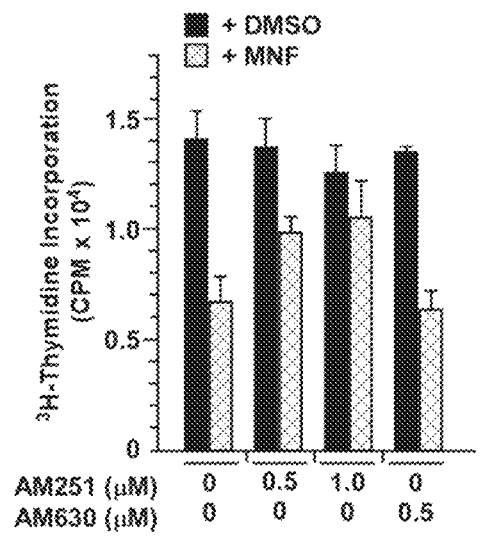
Figure 18D:
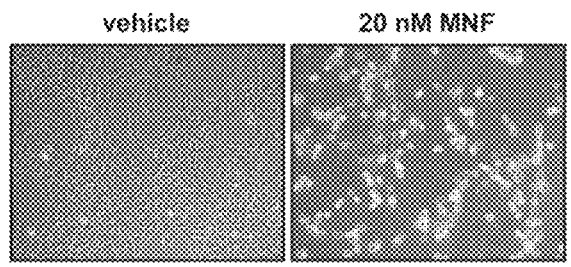
FIG. 18D, Changes in cell morphology were observed for C6 cells incubated with 20 nM MNF for 48 hours.

MNF reduces tumor cell proliferation. When cell proliferation assay was performed using the rat C6 glioma cell line, a potent growth inhibition was observed in response to MNF with a $IC_{50}$ of ~1.0 nM (FIG. 18A). The effect of the n-AR agonists isoproterenol and Fen on cell proliferation was compared to that of MNF in the absence and presence of the selective β2-AR blocker, ICI-118,551 (FIG. 18B). Both isoproterenol and Fen elicited weak 10-15% inhibition of C6 cell growth when used at 20 nM, and the same concentration of MNF caused a significant 54.3±1.2% reduction in mitogenesis (n=4, P<0.001). The addition of ICI-118,551 did not block the antiproliferative effect of MNF while impeding isoproterenol and Fen signaling (FIG. 18B). C6 glioma cells express both β2-AR and CB receptors, and the cellular actions of MNF have been reported earlier to implicate CB receptor activity. Preincubation with the CB1 receptor inverse agonist AM251 rendered C6 cells refractory to the growth-inhibitory effect of MNF, while inhibition of CB2 receptor with AM630 had minimal effect against MNF signaling (FIG. 18C). These results indicate that the anti-proliferative action of MNF occurs through CB1 receptor signaling. A coincident change in cell morphology and nuclear condensation was observed in MNF-treated C6 glioma cells, consistent with apoptosis (FIG. 18D).

Figure 19A:
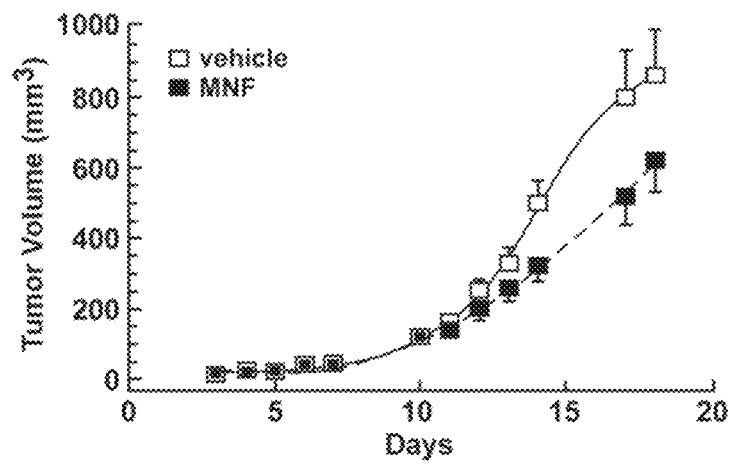
FIGS. 19A and 19B each include a graph illustrating MNF reduces tumor growth in vivo in a rat C6 glioma xenograft model. C6 tumor-bearing female nude mice were assigned randomly to either the vehicle or the MNF group. Treatment was given by injecting either 2 mg/kg MNF or citrate in PBS five days a week for 19 days. Tumor volume was monitored daily and mice were sacrificed on the day after the last treatment.
Figure 19B:
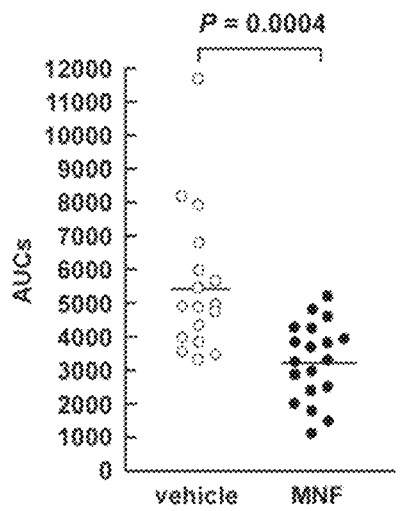

MNF reduces tumor growth in vivo in a rat C6 glioma xenograft model. To determine whether MNF might have a therapeutic effect in vivo, a rat C6 glioma xenograft model was developed in immune-deficient mice. Tumor-bearing female nude mice were treated intraperitoneally with MNF daily for 19 days. Significant reduction in tumor volume was observed in MNF-treated animals compared with the vehicle-treated group (P<0.008; FIG. 19A). These studies were performed in a second independent cohort of mice, and showed similar results (see FIG. 19B for combined results). Tumors were excised after the last day of treatment and snap frozen in liquid nitrogen for subsequent analyses.

Determination of MNF levels in vivo. At the completion of the study, the tumors from the MNF-treated animals were assayed for the tissue concentrations of MNF. The results indicated that significant concentrations of MNF accumulated in the tumor tissues, 141.0±52.5 ng/ml/g tissue (cohort 1, n=9) and 214.4±65.5 ng/ml/g tissue (cohort 2, n=7), demonstrating that systemically administered MNF reaches the proposed therapeutic target.

Figure 20E:
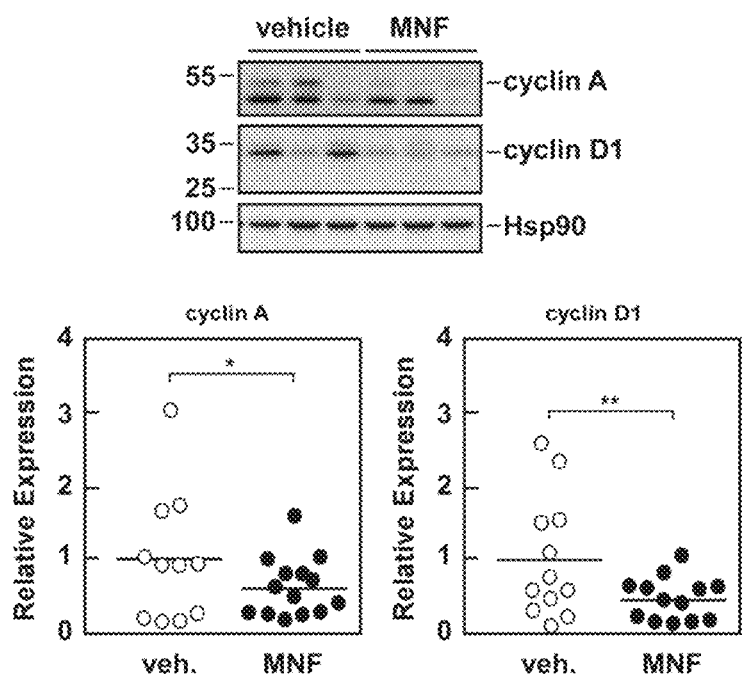
FIG. 20E demonstrates the negative impact of MNF on cyclin expression in C6 tumor xenografts. Lysates from tumor samples were separated by SDS-PAGE and Western blotting was carried out primary antibodies raised against cyclin A and cyclin D. Membranes were reprobed for Hsp90, which served as a loading control. Upper panel, representative immunoblots; lower panels, scatter plot of data showing significant differences in cyclin A and cyclin D1 expression between xenograft tumors from vehicle and MNF-treated mice. *, p<0.05; **, p<0.01 using two-tailed Student's t-test.
Figure 20F:
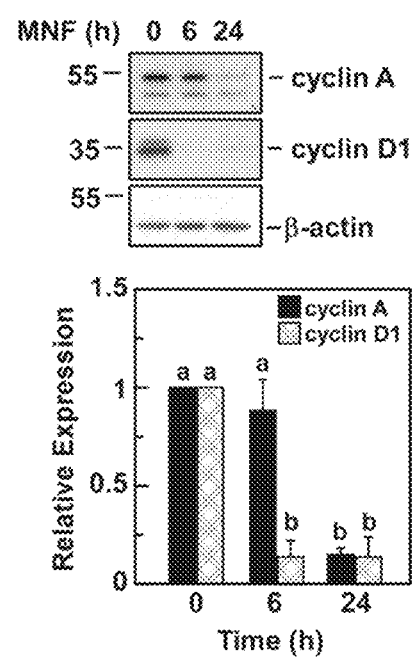
FIG. 20F, C6 glioma cells were incubated with 20 nM MNF for 6 and 24 hours after which lysates were prepared and immunoblotted for cyclin A and cyclin D1. Membranes were reprobed for β-actin, which served as a loading control. Upper panel, representative blots; lower panel, Bars represent densitometric quantification of each blot with the values in vehicle-treated cells set at 1.0. Bars represent means±SEM from three independent studies. a, b: significant difference between groups at P<0.01.

MNF alters gene expression profiling in C6 glioma xenografts. Global gene expression profiling by microarray analysis was performed to identify groups of genes in C6 glioma xenografts whose expression was altered upon MNF treatment as compared to tumor-bearing vehicle-treated mice. Six independent biological samples from two cohorts of animals were used in each group. After normalization and processing of the microarray data, genes were considered as differentially expressed if they showed an absolute zratio of 1.5 or more between MNF and vehicle and had been assigned an adjusted P value <0.05 and false discovery rate <0.3. Principal component analysis (PCA) revealed a discriminating pattern of significantly altered gene expression between MNF and vehicle groups (FIG. 20A). Computational analysis of the datasets derived from this study led to the identification of a number of cell cycle-associated GO terms, such as "DNA replication", "Cell cycle", "Mitosis" and "Cell division" that are likely involved in the control of tumor growth during MNF treatment (Table 8). The analysis of the overrepresented GO terms upon MNF treatment in the xenograft transcriptome revealed significant negative regulation of cell division-related genes together with those involved in control of metabolism of nucleic acids. Using parameterized analysis of gene set enrichment (PAGE), additional insight was provided into regulated signaling pathways and biological processes affected by MNF. From the collection of more than 308 gene sets, there were 55 gene sets whose expression levels were significantly altered by MNF, with the majority of the gene sets (48/55) being down-regulated (Table 10).

The intensity of this signature from the two cohorts of animals is represented in FIG. 20B and a partial list of 10 gene sets influenced most by MNF treatment is depicted in Table 9. Among the genes of interest many were downregulated in the MNF group compared to the vehicle control, including matrix metalloproteinase (MMP)-11 and 14 (FIG. 20C). Treatment with MNF also sensitized C6 glioma tumor xenograft to growth arrest via the down-regulation of Galnt3 and other cell cycle regulators, such as Ccna2, Cdkn3 and Bub1b (FIG. 20C). In addition, there was significant reduction in expression of molecular markers for glial brain tumors upon MNF treatment. On the other hand, apoptosis-associated transcripts such as Casp1, Casp11 and Casp12 were upregulated by MNF (FIG. 20C). Quantitative RT-PCR analysis confirmed that MNF decreased the expression of Bub1b, Cdkn3 Ccna2, Olig1, Sox4, and Galnt3 as compared to control (FIG. 20D), thus validating the microarray data. Overall, these results indicate routes by which MNF might negatively affect glioma growth and progression. Also, these results indicate biomarkers, which can be used to determine the efficiency of MNF treatment as well as glioma growth and progression in general. Thus, these studies disclose methods of diagnosing, prognosing and determining the efficiency of MNF as well as other treatments of tumor growth and progression in general by using the disclosed biomarkers as indicators.

TABLE 8

List of GOTerms influenced by MNF treatment of a C6 glioma xenograft model Z scores for 'MNF_Crtl' are shown. These studies were performed on two independent cohorts of mice, with both cohorts showing equivalent results.

| Annotation | GO Term | Set 1 | Set 2 | Combined |
| --- | --- | --- | --- | --- |
| GO0006270 | DNA replication initiation | −4.0283 | −3.7775 | −5.0248 |
| GO0048015 | Phosphoinositide mediated signaling | −4.2781 | −3.5441 | −5.2545 |
| GO0004527 | Exonuclease activity | −2.5829 | −5.4622 | −5.8765 |
| GO0000775 | Chromosome pericentric region | −6.7644 | −3.5296 | −6.3081 |
| GO0007051 | Spindle organization and biogenesis | −4.6166 | −5.2288 | −6.7039 |
| GO0006260 | DNA replication | −4.7695 | −6.0446 | −7.3157 |
| GO0007049 | Cell cycle | −5.1361 | −8.0162 | −9.3510 |
| GO0005634 | Nucleus | −2.1680 | −9.9454 | −9.4291 |
| GO0007067 | Mitosis | −7.5266 | −7.6563 | −10.1574 |
| GO0051301 | Cell division | −6.9059 | −8.0673 | −10.1585 |

TABLE 9

List of gene sets influenced by MNF treatment of C6 glioma xenograft model Size indicates the number of genes found in each gene set. These studies were performed on two independent cohorts of mice, with both cohorts showing equivalent results.

| Size | Name | Z score | P value | Fdr |
| --- | --- | --- | --- | --- |
| 40 | HIPPOCAMPUS_DEVELOPMENT_POSTNATAL | 10.3511 | 0.0020 | 0.0344 |
| 280 | TARTE_MATURE_PC | 5.3293 | 0.0097 | 0.1073 |
| 41 | HYPOPHYSECTOMY_RAT_DN | 3.9294 | 0.0170 | 0.1483 |
| 30 | HDAC1_COLON_BUT12 HRS_UP | 3.6676 | 0.0035 | 0.0527 |
| 60 | CELL_CYCLE | −7.4222 | 1.5E−10 | 1.73E−08 |
| 37 | P21_P53_ANY_DN | −7.4300 | 5.12E−09 | 4.31E−07 |
| 74 | LE_MYELIN_UP | −8.8777 | 6.34E−08 | 4.64E−06 |
| 24 | CROONQUIST_IL6_STARVE_UP | −9.0059 | 1.87E−18 | 6.31E−16 |
| 65 | IDX_TSA_UP_CLUSTER3 | −10.1593 | 3.15E−20 | 1.76E−17 |
| 79 | SERUM_FIBROBLAST_CELLCYCLE | −10.6997 | 2.98E−20 | 2.51E−17 |

TABLE 10

| Pathway Name | MNF_Control, cohort 1 | | | MNF_Control, cohort 2 | | | MNF_Conrol, combined cohorts | | |
|---|---|---|---|---|---|---|---|---|---|
| | (Z score) | (P_value) | (fdr) | (Zscore) | (P_value) | (fdr) | (Zscore) | (P_value) | (fdr) |
| HIPPOCAMPUS_DEVELOPMENT_POST-NATAL | 3.6731 | 0.0211 | 0.1456 | 10.3312 | 0.0020 | 0.0144 | 11.4209 | 0.0017 | 0.0282 |
| TARTE_MATURE_PC | 3.6636 | 0.0129 | 0.1088 | 5.3293 | 0.0097 | 0.1073 | 6.8026 | 0.0004 | 0.0085 |
| HDACI_COLON_BUT12 HRS_UP | 5.3212 | 0.0002 | 0.0053 | 3.6676 | 0.0035 | 0.0527 | 5.8481 | 0.0000 | 0.0007 |
| HYPOPHYSECTOMY_RAT_DN | 3.6187 | 0.0459 | 0.2249 | 3.9294 | 0.0170 | 0.1483 | 5.3951 | 0.0008 | 0.0144 |
| HDACI_TSABUT_UP | 4.1465 | 0.0080 | 0.0751 | 3.4480 | 0.0042 | 0.0600 | 5.2313 | 0.0006 | 0.0109 |
| HDACI_COLON_BUT16HRS_UP | 3.6723 | 0.0199 | 0.1426 | 3.4287 | 0.0072 | 0.0877 | 4.8024 | 0.0010 | 0.0176 |
| HDACI_COLON_BUT24HRS_UP | 3.0864 | 0.0323 | 0.1878 | 3.3154 | 0.0119 | 0.1209 | 4.4492 | 0.0010 | 0.0169 |
| ATRBRCAPATHWAY | -1.8815 | 0.0406 | 0.2138 | -2.9977 | 0.0000 | 0.0000 | -3.4407 | 0.0000 | 0.0002 |
| GOLDRATH_HP | -2.4433 | 0.0229 | 0.1518 | -2.2875 | 0.0441 | 0.2766 | -3.4750 | 0.0007 | 0.0141 |
| BRENTANI_REPAIR | -3.8568 | 0.0002 | 0.0052 | -2.9453 | 0.0101 | 0.1094 | -4.2370 | 0.0002 | 0.0048 |
| REN_E2F1_TARGETS | -2.9150 | 0.0121 | 0.1044 | -3.5319 | 0.0026 | 0.0414 | -4.4393 | 0.0008 | 0.0145 |
| MOREAUX_TACI_HI_IN_PPC_UP | -2.9881 | 0.0064 | 0.0635 | -3.8456 | 0.0007 | 0.0154 | -4.9180 | 0.0000 | 0.0009 |
| LAMB_CYCLIN_D3_GLOCUS | -2.8637 | 0.0360 | 0.2028 | -4.3054 | 0.0000 | 0.0000 | -5.0503 | 0.0000 | 0.0001 |
| PODI_KO_UP | -3.9363 | 0.0052 | 0.0553 | -4.3565 | 0.0064 | 0.0812 | -5.1416 | 0.0007 | 0.0129 |
| MOREAUX_TACI_HI_VS_LOW_DN | -4.3721 | 0.0000 | 0.0011 | -3.2936 | 0.0020 | 0.0334 | -5.1872 | 0.0000 | 0.0000 |
| E2F1_DNA_UP | -3.6781 | 0.0008 | 0.0142 | -4.4885 | 0.0004 | 0.0099 | -5.4288 | 0.0000 | 0.0014 |
| SHEPARD_CRASH_AND_BURN_MUT_VS_WT_DN | -3.9994 | 0.0035 | 0.0413 | -4.0540 | 0.0139 | 0.1315 | -5.5788 | 0.0009 | 0.0160 |
| IRITANI_ADPROX_LYMPH | -5.1468 | 0.0007 | 0.0132 | -3.3728 | 0.0387 | 0.2504 | -5.7142 | 0.0001 | 0.0075 |
| SHEPARD_GENES_COMMON_BW_CB_MO | -4.0300 | 0.0067 | 0.0656 | -4.3867 | 0.0259 | 0.1927 | -5.7440 | 0.0019 | 0.0308 |
| PEART_HISTONE_DN | -2.5055 | 0.0408 | 0.2142 | -5.2170 | 0.0002 | 0.0063 | -5.7817 | 0.0001 | 0.0017 |
| SHEPARD_BMYB_MORPHOLINO_DN | -4.4350 | 0.0022 | 0.0300 | -4.7947 | 0.0100 | 0.1089 | -6.0639 | 0.0002 | 0.0054 |
| DAC_FIBRO_DN | -4.4476 | 0.0007 | 0.0127 | -4.9523 | 0.0007 | 0.0142 | -6.4794 | 0.0000 | 0.0002 |
| BRCA_PROGNOSIS_NEG | -3.2974 | 0.0377 | 0.2052 | -5.4682 | 0.0000 | 0.0003 | -6.5976 | 0.0000 | 0.0002 |
| MANALO_HYPOXIA_DN | -3.2723 | 0.0019 | 0.0268 | -6.1956 | 0.0000 | 0.0000 | -6.7155 | 0.0000 | 0.0000 |
| LEE_TCELLS2_UP | -4.1051 | 0.0020 | 0.0282 | -5.6671 | 0.0000 | 0.0006 | -6.9464 | 0.0000 | 0.0000 |
| KENNY_WNT_UP | -4.0135 | 0.0093 | 0.0858 | -5.5586 | 0.0000 | 0.0000 | -6.9481 | 0.0000 | 0.0000 |
| STEMCELL_NEURAL_UP | -6.0983 | 0.0000 | 0.0001 | -5.0064 | 0.0000 | 0.0010 | -7.2833 | 0.0000 | 0.0000 |
| SASAKI_ATL_UP | -5.0963 | 0.0000 | 0.0010 | -5.5299 | 0.0000 | 0.0005 | -7.2897 | 0.0000 | 0.0000 |
| SASAKI_TCELL_LYMPHOMA_VS_CD4_UP | -5.0963 | 0.0000 | 0.0010 | -5.5299 | 0.0000 | 0.0005 | -7.2897 | 0.0000 | 0.0000 |
| DNA_REPLICATION_REACTOME | -3.8683 | 0.0039 | 0.0450 | -6.5700 | 0.0000 | 0.0000 | -7.3185 | 0.0000 | 0.0000 |
| VERNELL_PRB_CLSTR1 | -3.4691 | 0.0269 | 0.1692 | -6.5636 | 0.0000 | 0.0000 | -7.4144 | 0.0000 | 0.0000 |
| GAY_YY1_DN | -7.6370 | 0.0000 | 0.0000 | -4.7456 | 0.0016 | 0.0295 | -7.4972 | 0.0000 | 0.0001 |
| CANCER_UNDIFFERENTIATED_META_UP | -4.8288 | 0.0001 | 0.0034 | -6.2847 | 0.0000 | 0.0013 | -7.7981 | 0.0000 | 0.0002 |
| CELL_CYCLE_KEGG | -4.1925 | 0.0008 | 0.0139 | -7.0955 | 0.0000 | 0.0000 | -7.8764 | 0.0000 | 0.0000 |
| ADIP_DIFF_CLUSTERS | -4.6054 | 0.0050 | 0.0547 | -6.8850 | 0.0000 | 0.0006 | -7.9684 | 0.0000 | 0.0005 |
| OLDAGE_DN | -4.5391 | 0.0006 | 0.0115 | -7.1043 | 0.0000 | 0.0001 | -8.1220 | 0.0000 | 0.0000 |
| MIDDLEAGE_DN | -3.6696 | 0.0102 | 0.0919 | -7.7600 | 0.0000 | 0.0000 | -8.2457 | 0.0000 | 0.0000 |
| TARTE_PLASMA_BLASTIC | -4.8905 | 0.0002 | 0.0054 | -6.7905 | 0.0000 | 0.0000 | -8.3308 | 0.0000 | 0.0000 |
| YU_CMYC_UP | -4.4689 | 0.0049 | 0.0539 | -7.3723 | 0.0000 | 0.0000 | -8.4501 | 0.0000 | 0.0000 |
| CMV_IE86_UP | -6.1497 | 0.0000 | 0.0000 | -6.5954 | 0.0000 | 0.0000 | -8.5032 | 0.0000 | 0.0000 |
| HOFFMANN_BIVSBII_BI_TABLE2 | -5.1273 | 0.0001 | 0.0030 | -7.7114 | 0.0000 | 0.0005 | -8.5773 | 0.0000 | 0.0002 |
| CELL_CYCLE | -5.0187 | 0.0000 | 0.0013 | -7.4222 | 0.0000 | 0.0000 | -8.6730 | 0.0000 | 0.0000 |
| KAMMINGA_EZH2_TARGETS | -5.3211 | 0.0000 | 0.0004 | -7.2448 | 0.0000 | 0.0000 | -8.8163 | 0.0000 | 0.0000 |
| P21_P53_ANY_DN | -5.0275 | 0.0012 | 0.0186 | -7.4300 | 0.0000 | 0.0000 | -8.8530 | 0.0000 | 0.0000 |
| PRMT5_KD_UP | -9.3903 | 0.0000 | 0.0000 | -5.4620 | 0.0000 | 0.0010 | -8.9362 | 0.0000 | 0.0000 |
| CROONQUIST_IL6_RAS_DN | -6.7147 | 0.0000 | 0.0000 | -7.7040 | 0.0000 | 0.0000 | -9.7453 | 0.0000 | 0.0000 |
| DOX_RESIST_GASTRIC_UP | -5.8557 | 0.0000 | 0.0001 | -8.6145 | 0.0000 | 0.0000 | -10.1840 | 0.0000 | 0.0000 |
| LEE_TCELLS3_UP | -7.2409 | 0.0000 | 0.0000 | -8.0339 | 0.0000 | 0.0000 | -10.3427 | 0.0000 | 0.0000 |
| LI_FETAL_VS_WT_KIDNEY_DN | -5.4447 | 0.0001 | 0.0024 | -9.1715 | 0.0000 | 0.0000 | -10.4609 | 0.0000 | 0.0000 |
| ZHAN_MM_CD138_PR_VS_REST | -6.1404 | 0.0000 | 0.0000 | -9.0080 | 0.0000 | 0.0000 | -10.7002 | 0.0000 | 0.0000 |
| CROONQUEST_IL6_STARVE_UP | -6.5055 | 0.0000 | 0.0000 | -9.0059 | 0.0000 | 0.0000 | -10.7172 | 0.0000 | 0.0000 |
| LE_MYELIN_UP | -6.5477 | 0.0000 | 0.0009 | -8.8777 | 0.0000 | 0.0000 | -10.8010 | 0.0000 | 0.0000 |
| IDX_TSA_UP_CLUSTER3 | -6.1057 | 0.0000 | 0.0008 | -10.1593 | 0.0000 | 0.0000 | -11.3388 | 0.0000 | 0.0000 |
| SERUM_FIBROBLAST_CELLCYCLE | -7.2985 | 0.0000 | 0.0000 | -10.6997 | 0.0000 | 0.0000 | -12.2668 | 0.0000 | 0.0000 |

Oligodendrocyte transcription factor 1 (Olig1) has been identified as a novel glioblastoma marker with diagnostic and prognostic value. Moreover, SRY-box 4 (Sox4) is a transcription factor that has been implicated in the determination of the cell fate and in tumorigenesis. The fact that Olig1 and Sox4 mRNA levels were reduced in MNF-treated C6 glioma tumors compared with the control group is consistent with decreased activation of molecular pathways leading to gliomagenesis. The involvement of Cdkn3, Bub1b and Olig-1 in gliomagenesis is established. Here, evidence is provided of a down-regulation in the expression levels of these genes in rat C6 glioma tumour xenografts in response to MNF, indicating that MNF and related analogs represent a therapeutic strategy in the treatment of high-grade gliomas. MNF is readily transported across the blood-brain barrier and can accumulate in the rat brain.

This example demonstrates MNF-dependent chemoprevention in a glioblastoma xenograft model in the mouse and provides a mechanism for its anticancer action in vivo. Also, diagnostic markers and method of determining the efficiency of tumor treatment were revealed.

Example 9

MNF Targets GPR55-Mediated Ligand Internalization and Impairs Cancer Cell Motility This example demonstrates that MNF targets GPR55-mediated ligand internalization and impairs cancer cell motility.

(R,R')-4'-Methoxy-1-naphthylfenoterol (MNF) promotes growth inhibition and apoptosis of human HepG2 hepatocarcinoma cells via cannabinoid receptor (CBR) activation. The synthetic CB1R inverse agonist, AM251, has been shown to block the anti-mitogenic effect of MNF in these cells; however, AM251 is also an agonist of the recently deorphanized, lipid-sensing receptor, GPR55, whose upregulation contributes to carcinogenesis. Here, the role of GPR55 in MNF signaling in human HepG2 and PANC-1 cancer cell lines in culture was investigated, with a focus on internalization of the fluorescent ligand Tocrifluor 1117 (T1117), reorganization of actin cytoskeleton, and cell motility as measured by scratch assay. Results indicated that GPR55 knockdown by RNA interference markedly reduced cellular uptake of T1117, a process that was sensitive to MNF inhibition. GPR55 internalization mediated by the atypical cannabinoid O-1602 was blocked by MNF in GPR55-expressing HEK293 cells. Pretreatment of HepG2 and PANC-1 cells with MNF significantly abrogated the induction of ERK1/2 phosphorylation in response to AM251, 0-1602 and fetal bovine serum, known to contain bioactive lipids. Moreover, MNF exerted a coordinated negative regulation of AM251 and O-1602 inducible processes, including change in cell morphology and migration using scratch wound healing assay. This study shows that MNF impairs GPR55-mediated signaling and has therapeutic potential in the management of cancer by facilitating future research on GPR55.

Accumulation of cAMP by beta2-adrenoreceptor ($\beta$2-AR) agonists has been associated both with a decrease and increase in the mitogenic response of cancer cell lines in culture. The mechanisms that determine cell type-specificity of $\beta$2-AR-mediated antitumor activity are poorly understood and raise questions about possible biased agonism of the $\beta$2-AR, whereby the molecular structure and stereochemistry of the agonist and the cellular environment of the receptor stabilizes one or more ligand-specific active conformations of $\beta$2-AR. The main consequence of biased agonism at the $\beta$2-AR [and other G protein-coupled receptors] is the activation of multiple G-protein isoforms and modulation of various downstream signal transduction pathways that can lead to dramatic differences in biological outcomes.

(R,R')-4'-methoxy-1-naphthylfenoterol (MNF) is an analog of fenoterol with a 573-fold greater selectivity for the $\beta$2-adrenergic receptor ($\beta$2-AR) than $\beta$1-AR. It enhances cAMP accumulation with $EC_{50}$ value of 3.90 nM in human $\beta$2-AR-overexpressing cells and attenuates proliferation of 1321N1 astrocytoma cells with $IC_{50}$ value of 3.98 nM. In contrast to (R,R')-fenoterol, MNF activates both G$\alpha$s and G$\alpha$i proteins and potently stimulates cardiomyocyte contractility, consistent with its role as a $\beta$2-AR agonist. However, it is disclosed herein that MNF treatment of the human-derived HepG2 hepatocarcinoma cell line causes growth arrest and apoptosis via a $\beta$2-AR-independent route. The MNF response was found to be insensitive to the $\beta$2-AR antagonist ICI 118,551, and U87MG cells, which lack $\beta$2-AR binding activity, were responsive to the antimitogenic effects of MNF. The presence of the naphthyl moiety in MNF led us to speculate that it may share structural similarities with other ligands and, therefore, behave as a dually acting compound with unique affinity and selectivity profile.

Cannabinoid receptors (CBRs) are often co-expressed with $\beta$2-AR in many tissues and various cell types, and their propensity to heterodimerize demonstrates the potential for crosstalk between the two receptors. In fact, CBRs can modulate $\beta$2-AR activity. The engagement of CBRs by endogenous and synthetic cannabinoid ligands results in the regulation of proliferation and apoptosis of cancer cells, including HepG2 cells. It is interesting that treatment with selective pharmacological inverse agonists of CBRs blocks the antiproliferative actions of MNF in HepG2 cells, consistent with the potential role of CBRs in MNF signaling. Even though AM251 and its clinical analog, rimonabant (SR141716A; N-(piperidin-1-yl)-5-(4-chlorophenyl)-1-(2, 4-dichlorophenyl)-4-methyl-1H-pyrazole-3-carboxamide hydrochloride), interact with CB1R as inverse agonists, there is growing body of evidence to suggest that they also act as agonists for the recently deorphanized GPR55. GPR55 is a G protein-coupled receptor with lipid-sensing properties whose upregulation contributes to the aggressive behavior of various cancer types. A role for ERK/MAP kinase signaling during microglial activation and the promotion of cancer cell proliferation by GPR55 has been proposed. AM251 also promotes neutrophil chemotaxis by acting as a GPR55 agonist. Thus, the actions of AM251 and rimonabant, which have been widely interpreted as being mediated by CB1R, may, in fact, include off-target effects of GPR55 by this class of compounds.

The current example was designed to investigate the contribution of GPR55 in MNF actions in two human cancer cell lines in culture, HepG2 and PANC-1 cells. Using Tocrifluor 1117 (T1117), a fluorescent ligand that binds to endogenous GPR55, with low affinity for CB1R, pharmacodynamic studies were performed and the data indicate that MNF significantly delays T1117 incorporation via impairment in the internalization/recycling of GPR55. Treatment with MNF also resulted in impaired ligand-mediated activation of downstream GPR55 signaling pathways in both tumor cell lines and their cell migration using the wound-healing assay. The present data show that cell exposure to MNF leads to impairment in GPR55 signaling.

Materials and Methods

Materials. (R,R')-4'-methoxy-1-naphthylfenoterol (MNF) was synthesized as described previously (Jozwiak et al., *Bioorg. Med. Chem.* 18: 728, 736, 2007 which is hereby incorporated by reference in its entirety). Eagle's minimum essential medium, trypsin solution, phosphate-buffered saline (PBS), fetal bovine serum (FBS), 100× solutions of sodium pyruvate (100 mM), L-glutamine (200 mM), and penicillin/streptomycin (a mixture of 10,000 units/ml penicillin and 10,000 µg/ml streptomycin) were obtained from Quality Biological (Gaithersburg, Md., USA). WIN 55,212-2, AM251, and AM630 were purchased from Cayman Chemical (Ann Arbor, Mich.), whereas CP 55,940, O-1602 and Tocrifluor T1117 were from Tocris Bioscience (Ellisville, Mo., USA).

Maintenance and treatment of cell lines. Human HepG2 hepatocarcinoma cells and human PANC-1 cells were purchased from ATCC (Manassas, Va., USA). HepG2 cells were maintained in Eagle's minimum essential medium supplemented with 1% L-glutamine, 1% sodium pyruvate, 1% penicillin/streptomycin, and 10% FBS (Hyclone, Logan, Utah, USA). PANC-1 cells were cultured in phenol red-free Dulbecco's modified Eagle's medium (DMEM) supplemented with 4.5 g/L glucose and 1.5 g/L sodium bicarbonate together with glutamine, pyruvate, penicillin/streptomycin and 10% FBS. HEK293 cells stably expressing the HA-tagged human GPR55 (hGPR55-HEK293) were a gift of Maria Waldhoer (Medical University of Graz, Graz, Austria) (Henstridge et al., *Br. J. Pharmacol.* 160: 604-614, 2010). The cells were maintained in DMEM with 4.5 g/L glucose supplemented with 10% FBS, 0.2 mg/ml G418, and penicillin/streptomycin. All cell lines were maintained in culture at 37° C. in 5% CO2, and the medium was replaced every 2-3 days.

Cellular uptake of TocriFluor T1117, a fluorescently labeled GPR55 agonist Cells were grown in 35-mm glass bottom culture dishes (MatTek Corp., Ashland, Mass., USA) for 48 hours until reaching ~70% confluence. Serum-depleted cells were incubated either with DMSO (vehicle, 0.1%), MNF (1 µM), or synthetic cannabinoid compounds (AM630, AM251, 0-1602, CP 55,940) for 30 minutes prior to the addition of the novel fluorescent diarylpyrazole cannabinoid ligand, Tocrifluor T1117 (10-100 nM). Cells were imaged with a Zeiss LSM 710 confocal microscope equipped with a temperature-controlled and humidified $CO_2$ chamber and a definite focus system. A 561 nm DPSS laser was used for the excitation of the 5-TAMRA conjugate. The time-series function of the Zeiss Zen software was used to collect images with a 40×1.3 NA objective every 30 s for up to one hour, with all confocal settings remaining the same throughout the studies. Still images, movies and fluorescent intensity quantitation were obtained from these series using the Zeiss Zen software. Studies were repeated at least two to three times.

Gene silencing. HepG2 cells were transfected with siRNA oligos (1.25 µg) against CB1R, $CB_2R$, or GPR55 or a non-silencing siRNA control (Santa Cruz Biotechnology, Santa Cruz, Calif.) for 48 hours using 10 µl of siRNA Transfection Reagent (Santa Cruz Biotechnology) following the manufacturer's protocol. siRNAs have been validated to perform efficient knockdown with minimal off-target effects. Following 48 hours of siRNA treatment, cells were washed with PBS, and maintained in serum-free medium before the addition of T1117.

GPR55 internalization assay. Endocytosis of GPR55 was observed following a previously described protocol with minor modifications (Henstridge et al., *Br. J. Pharmacol.* 160: 604-614, 2010). Briefly, hGPR55-HEK293 cells were grown on Lab-Tek II CC2 chamber slides (Thermo Scientific Nunc, Rochester, N.Y.) for 48 hours in regular media and then were serum starved for 1 hour. A preincubation with 1:1000 rabbit HA antibody (Covance, Md.) was performed in the presence of vehicle (0.1% DMSO) or 1 µM MNF in serum-free media for 45 minutes at 37° C. in the $CO_2$ incubator. Cells were then washed extensively with PBS and treated with 5 µM 01602 in serum-free media for 20 minutes at 37° C. in the $CO_2$ incubator. Subsequently, cells were washed three times, fixed in fresh 3.7% paraformaldehyde in PBS (10 min), and incubated with anti-rabbit Alexa Fluor 488 antibody (Molecular Probes, Eugene, Oreg.; 1:1000, 30 minutes). Cells were washed and fixed for a second time prior to permeabilization with 0.2% Triton X-100 (5 minutes). Incubation with anti-rabbit Alexa Fluor 568 antibody (Molecular Probes; 1:1000, 30 minutes) was carried out to determine the extent of internalized GPR55-HA antibody complex. The cells were washed in PBS, nuclear counterstaining was performed with DAPI (4',6-diamidino-2-phenylindole) added to the Prolong Gold antifade mounting medium (Invitrogen) and cured for 24 hours at room temperature in the dark. Images were acquired with a Zeiss LSM 710 confocal microscope (Thornwood, N.Y.) using Carl Zeiss LSM software.

Scratch assays. These assays were carried out essentially as described previously (Fiori et al., *Endocrinology* 150: 2551-2560, 2009). In brief, cells were seeded in 12-well nontreated polystyrene cell culture plates with flat bottom (Greiner Bio-One, Monroe, N.C.). Once the cells became confluent, a scratch wound was made with a pipette tip and pictured immediately (time 0). Cells were pretreated either with vehicle (DMSO, 0.1%) or the synthetic GPR55 ligands AM251 (1 µM) or O-1602 (1 µM) for 30 minutes followed by the addition of MNF (1 µM) where indicated. Cell migration was examined at 12, 24, 36, 48 hours and 12, 18, 24, 48 hours after scratch for the HepG2 and PANC-1 cells, respectively. Images of the same field were taken every 3 hours to determine the rate of cell migration. Images were captured on an Axiovert 200 inverted microscope (Carl Zeiss, Thornwood, N.Y.) mounted with an AxioCam HRc digital camera (Carl Zeiss) and the measurement of scratch area was performed with ImageJ 1.46s software (National Institutes of Health, Bethesda, Md.). Each study was performed in duplicate dishes and repeated at least twice.

Figure 28A:
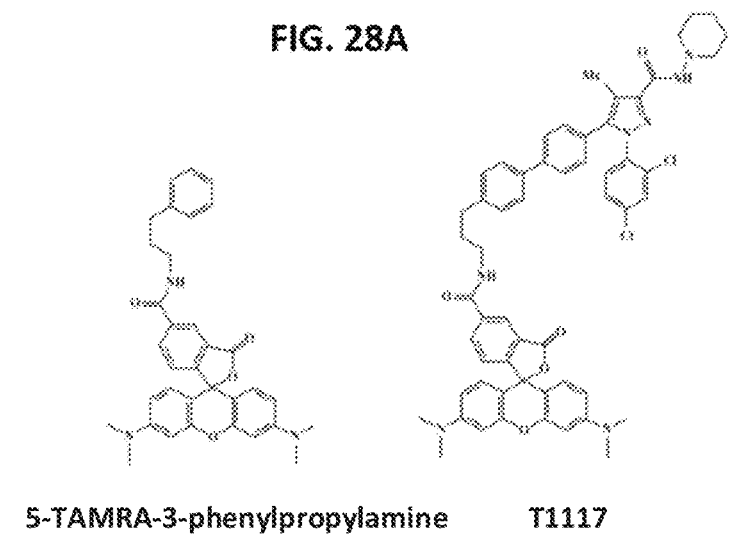
FIG. 28A provides the structure of 5'-TAMRA-3-phenyl-propan-1-amine (TAMRA-PPA) and T1117.
Figure 28B:
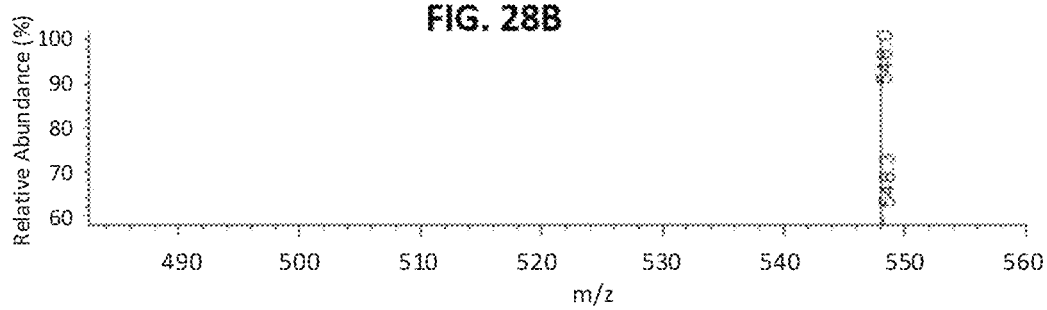
FIG. 28B provides the mass spectrum of TAMPRA-PPA ion, m/z equals 548.0.
Figure 28C:
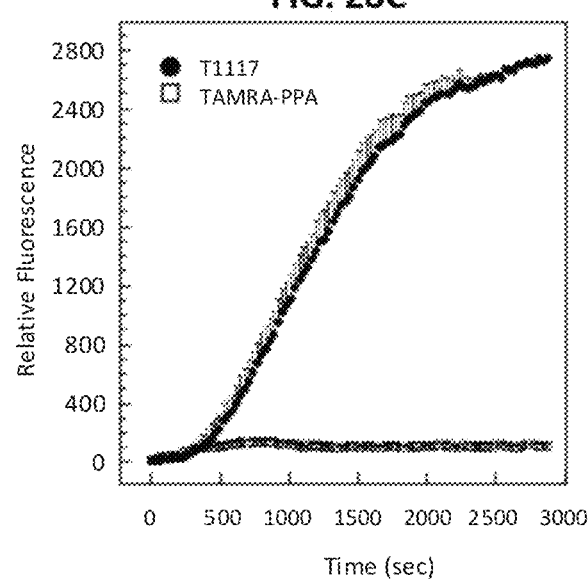
FIG. 28C provides a comparison of the cellular accumulation of T1117 (10 nM) vs. TAMRA-PPA (20 nM) in serum-depleted HepG2 cells. Note the absence of TAMRA-PPA incorporation in cells.

Synthesis of 5'-TAMRA-3-phenylpropan-1-amine. Ten nmoles of the NHS ester of 5'-TAMRA (Sigma-Aldrich, St-Louis, Mo.) was incubated with 20 nmoles of 3-phenyl-propan-1-amine (Sigma-Aldrich) in 1 ml of 0.1M PBS, pH 8.0 for 4 hours. The solution was stream dried under nitrogen and reconstituted in 500 µl of a 1:1 solution of 10 mM Tris-HCl, pH 8.0 in ethanol. The formation of 5'-TAMRA-3-phenylpropan-1-amine (TAMRA-PPA, structure shown in FIG. 28A) and absence of the NHS ester of 5'-TAMRA was confirmed by mass spectrometry (FIGS. 28B, 28C). A stock solution of 10 mM of TAMRA-PPA was prepared, aliquoted and stored at −20° C.

Western blot analysis. For detection of intracellular signaling proteins, cells were lysed in radioimmunoprecipitation buffer containing EGTA and EDTA (Boston BioProducts, Ashland, Mass.). The lysis buffer contained a protease inhibitor cocktail (Sigma-Aldrich) and phosphatase inhibitor cocktail (Calbiochem, San Diego, Calif.). Equivalent amount of proteins (14 and 54 µg/well for PANC-1 and HepG2 cells, respectively) were separated on 4 to 12% precast gels (Invitrogen, Carlsbad, Calif.) using SDS-polyacrylamide gel electrophoresis under reducing conditions and then electrophoretically transferred onto polyvinylidene fluoride membrane (Invitrogen). Western blots were performed according to standard methods, which involved blocking in 5% non-fat milk and incubated with the antibody of interest, followed by incubation with a secondary antibody conjugated with the enzyme horseradish perodixase. The detection of immunoreactive bands was performed by chemiluminescence using the ECL Plus Western Blotting Detection System (GE Healthcare, Piscataway, N.J.). The quantification of bands was done by volume densitometry by using ImageJ software. The rabbit polyclonal antibodies against EGFR were obtained from Cell Signaling Technology, Inc. (Beverly, Mass.) and the monoclonal anti-Hsp90 was purchased from Santa Cruz Biotechnology, Inc. (Santa Cruz, Calif.).

Effect of MNF on O-1602-mediated increase in cell signaling. Serum-starved cells were pretreated in the absence or presence of 1 µM MNF for 10 minutes followed by a 10 minute incubation with 0, 2.5 and 10 µM O-1602 or 10% FBS, after which the levels of total ERK2 and phosphorylated forms of ERK1/2 (pErk1/2, Thr202/Tyr204), were determined by Western blotting technique. All primary antibodies were purchased from Cell Signaling Technology and used at a dilution recommended by the manufacturer.

Statistical analysis. Prism 4 (GraphPad Software, Inc., La Jolla, Calif.) running on a personal computer was used to perform all the statistical data analysis.

Results

Figure 21A:
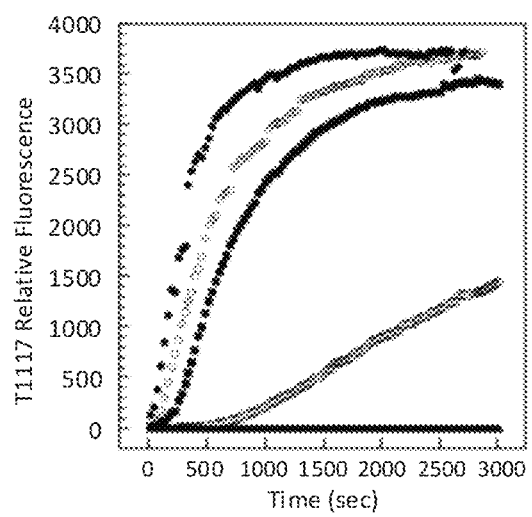
FIGS. 21A-21D illustrate rapid and saturable incorporation of T1117 in HepG2 cells. Cellular entry of T1117 was measured on a Zeiss 710 confocal microscope with thermo-regulated chamber system for live cell imaging.
Figure 21B:
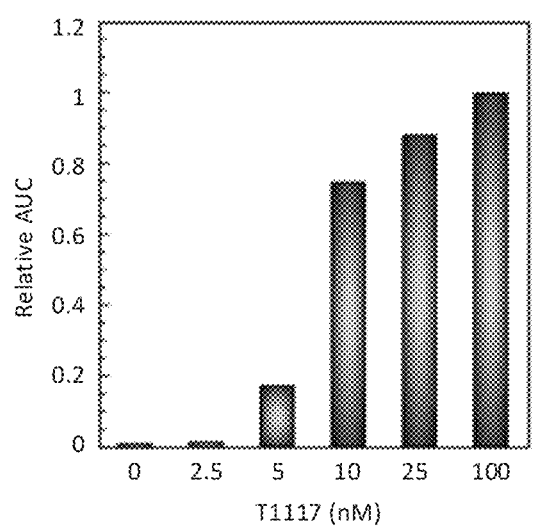
Figure 21C:
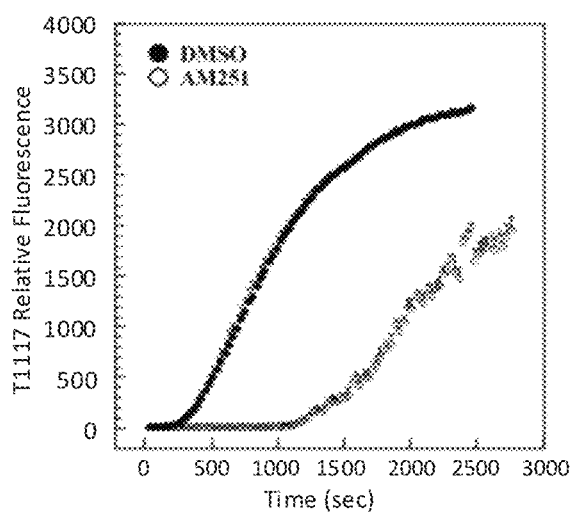
Figure 21D:
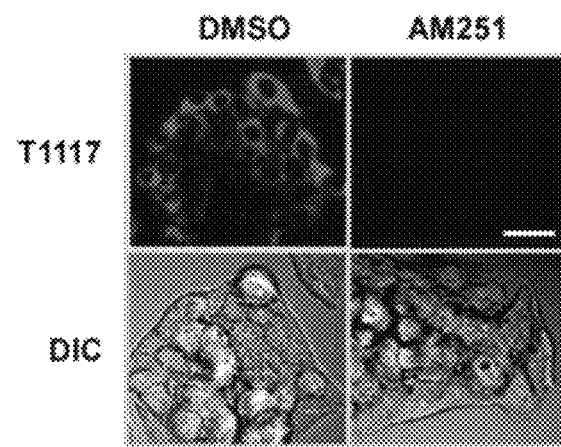
Figure 29A:
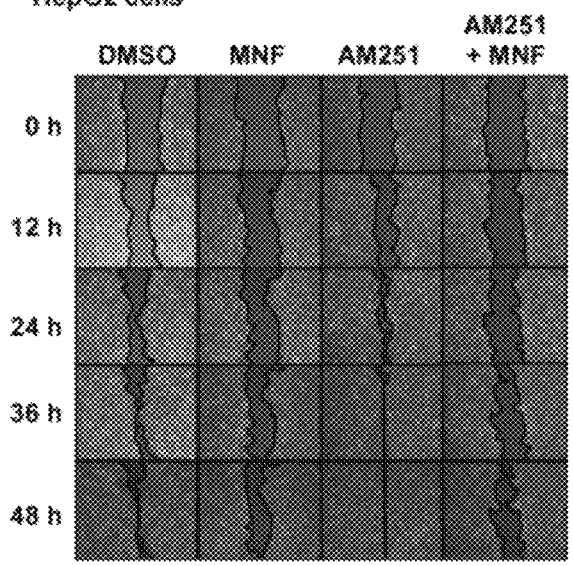
FIGS. 29A-29C are captured images of a representative wound-healing assay. Confluent HepG2 (FIG. 29A) and PANC-1 (FIG. 29B) cells were subjected to scratch wound and treated as described above for FIGS. 27A-27D. Similar profiles were obtained in four independent assays.
Figure 29B:
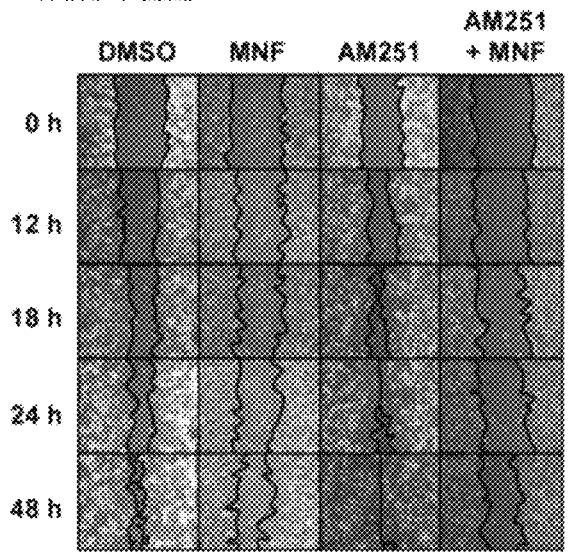
Figure 29C:
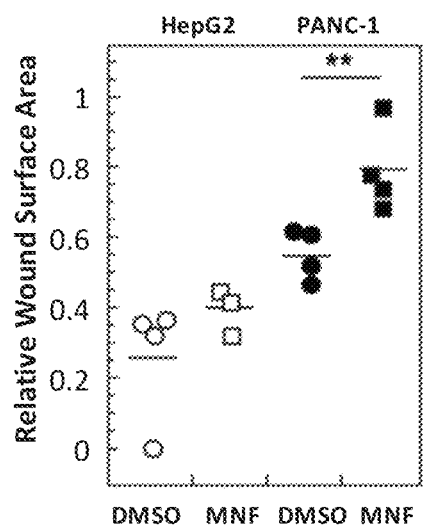

A role for the deorphanized GPR55 in the cellular incorporation of T1117. The fluorescently labeled AM251 analog, T1117, acts as a ligand for GPR55 with low affinity for CB1R. To address the issue of sensitivity and specificity of T1117 incorporation, serum-depleted cells were maintained on a confocal microscope stage equipped with a temperature-controlled and humidified $CO_2$ chamber. Studied herein were the characteristics of T1117 incorporation in human HepG2 and PANC-1 cells at 37° C. The amount of cellular T1117 levels increased in a dose-dependent manner, with a maximal incorporation at 100 nM and a half-maximal effect at approximately 8 nM (FIGS. 21A, 21B). Simultaneous addition of a 100× molar excess of unlabeled AM251 caused a significant 18-minutes delay in the cellular accumulation of T1117 (FIGS. 21C, 21D) Similarly, dropping the temperature to 10° C. reduced the rate of T1117 uptake. To establish whether the cellular incorporation of T1117 required the presence of the AM251 moiety, HepG2 cells were incubated for up to 1 hour with equimolar amounts either of T1117 (5'-TAMRA-(3-phenylpropan-1-amine)-labeled AM251) or 5'-TAMRA-3-phenylpropan-1-amine (TAMRA-PPA). Under these conditions, there was no significant incorporation of fluorescence upon cell incubation with TAMRA-PPA (FIG. 29C). These results demonstrate that cellular accumulation of T1117 is rapid and saturable, and initiated through competitive binding to cell surface receptors.

Figure 22A:
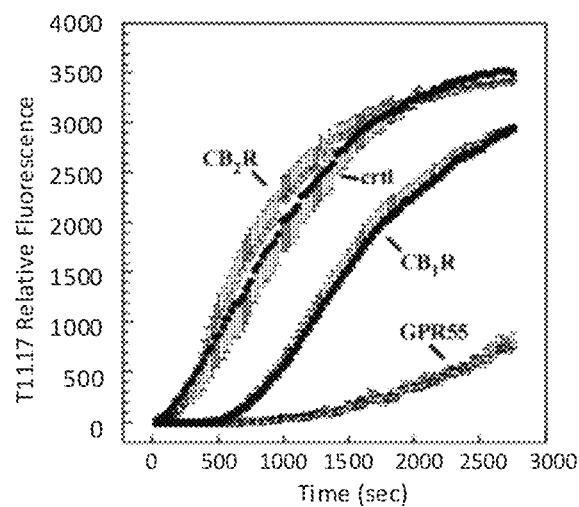
FIGS. 22A-22D illustrate a role for GPR55 in cellular incorporation of T1117.
Figure 22B:
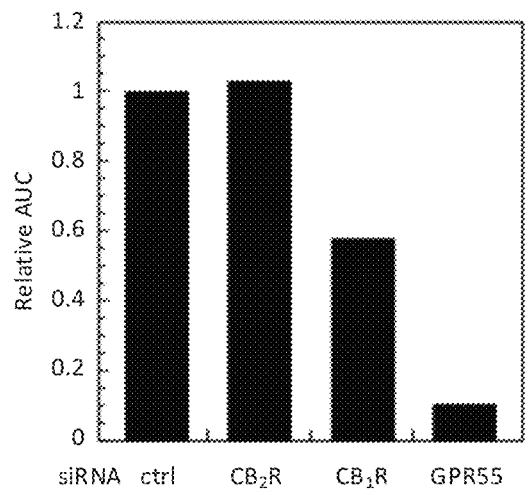
Figure 24A:
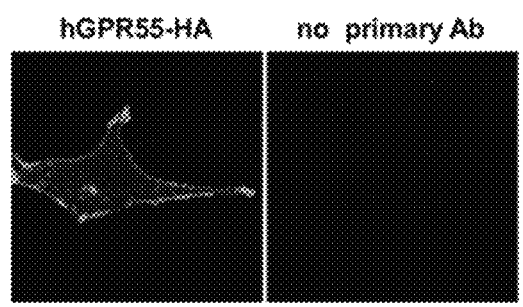
FIGS. 24A and 24B show MNF impairs ligand-induced internalization of GPR55. HEK293 cells stably transfected with 3×HA-tagged hGPR55 vector were serum-starved, and then incubated with anti-HA antibody in the absence or presence of MNF (1 µM) for 45 minutes at 37° C. After extensive washing, O-1602 (5 µM) was added to the cells for 20 minutes at 37° C. to promote GPR55 internalization. Intact cells were fixed and then incubated with anti-rabbit Alexa Fluor 488 antibody to label cell surface GPR55. After a permeabilization step, anti-rabbit Alexa Fluor 568 antibody was added to detect intracellular GPR55. Nuclei were counterstained with DAPI. Scale bar=20 µm.
Figure 24B:
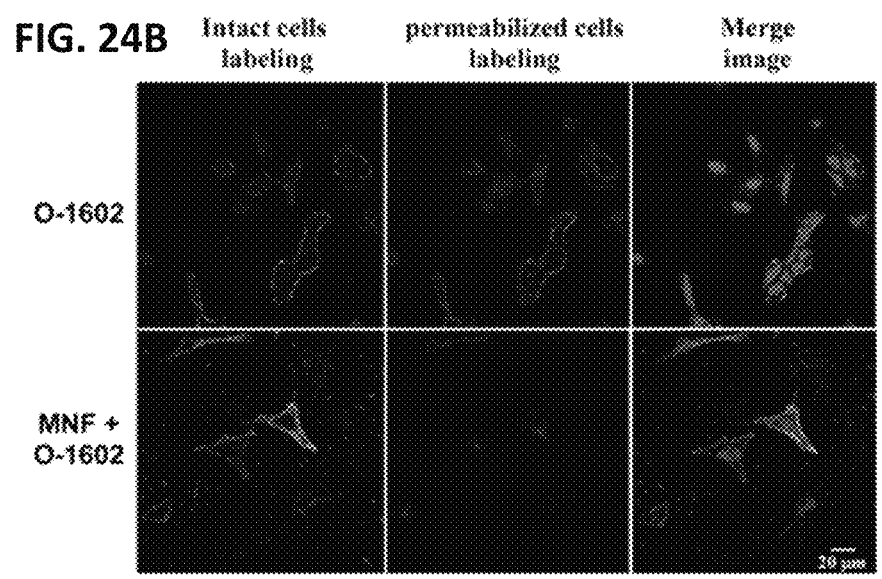

To confirm the role of GPR55 in the cellular uptake of T1117, HepG2 cells were incubated with siRNA oligos against CB1R, CB2R or GPR55 and the non-silencing siRNA control for 48 hours, after which T1117 incorporation was monitored (FIG. 24A, 24B). Studies showed selective reduction in gene expression when using siRNA duplexes against the indicated targets. In HepG2 cells transfected with control siRNA, entry of T1117 was observed with half-maximum incorporation at ~15 minutes (FIG. 22A). Silencing of GPR55 blocked T1117 uptake by more than 6-fold whereas a significant 10-12 minutes delay occurred upon CB1R silencing, ultimately resulting in a 40% reduction in cellular T1117 levels (FIG. 22B). However, in cells transfected with CB2R siRNA, the profile of T1117 incorporation was comparable to that of non-silencing siRNA-transfected cells. These results indicate that GPR55 plays a major role in the cellular entry of T1117 and that constitutive CB1R activity may participate in this GPR55 function.

Figure 22C:
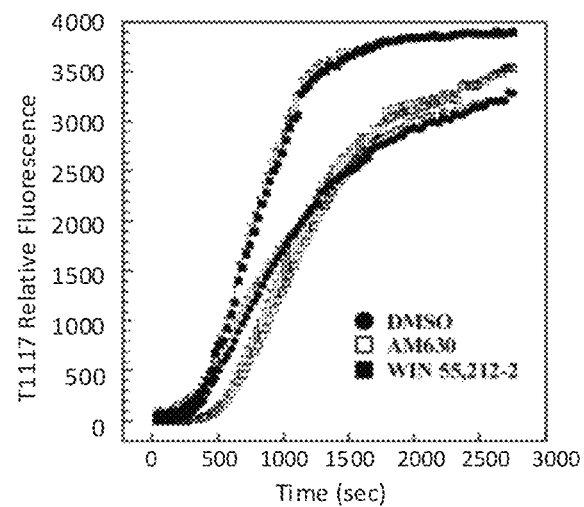
Figure 22D:
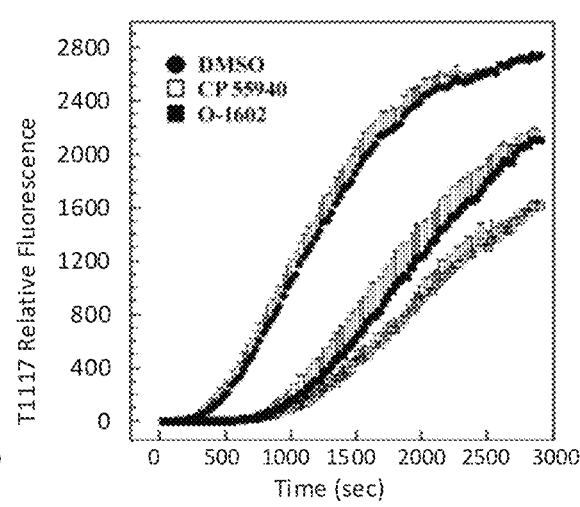

To independently confirm these observations, HepG2 cells were pretreated with selective inverse agonists/antagonists of CB1R and CB2R prior to the addition of T1117. The CB2R inverse agonist, AM630, was largely inactive while pretreatment with the CBR agonist, WIN 55,212-2, markedly increased the rate of T1117 accumulation (FIG. 22C). The potent synthetic cannabinoid agonist CP 55,940 has been reported to block GPR55 internalization in a heterologous expression system. Here, a 30-minutes pretreatment with CP 55,940 (0.25 µM) clearly reduced T1117 uptake by 2.5-fold in HepG2 cells (FIG. 24D). Similarly, cell treatment with the atypical cannabinoid O-1602 (0.25 µM) caused a 12.5-minutes delay in cellular accumulation of T1117, resulting in a 47% reduction in the amount of T1117 incorporated (FIG. 22D).

Figure 23A:
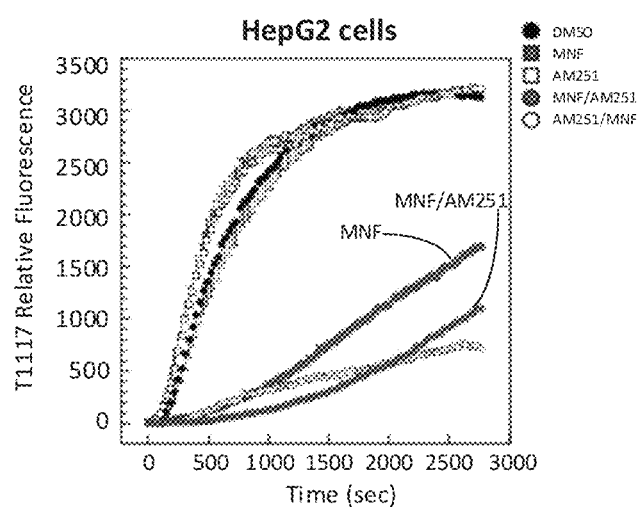
Figure 23B:
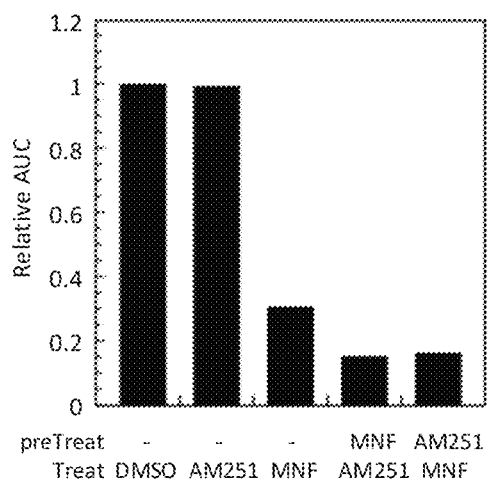
FIG. 23B, D: Relative AUC data, and the DMSO values were set at 1.

MNF inhibits cellular incorporation of T1117. The effects of MNF on GPR55 signaling were initially investigated using the incorporation of T1117 as an in vitro model of GPR55-dependent activity. Pretreatment of HepG2 cells with 1 µM AM251 for 30 minutes neither inhibited nor enhanced constitutive T1117 incorporation, suggesting the absence of negative or positive allosteric modulation (FIGS. 23A, 23B). This is in contrast to the effect of concomitant addition of a 100×-excess of AM251 with T1117, which significantly reduced cellular T1117 accumulation under the same assay conditions (FIG. 23C), possibly because of the lower specific activity of the fluorescent marker. When this study was performed in the presence of MNF alone, a ~70% reduction was observed (FIGS. 23A, 23B). Moreover, the addition of AM251 either before or after the 30-minutes treatment with MNF caused a further lowering in T1117 incorporation, with a ~6.8-fold reduction as compared to vehicle-treated cells.

Figure 23C:
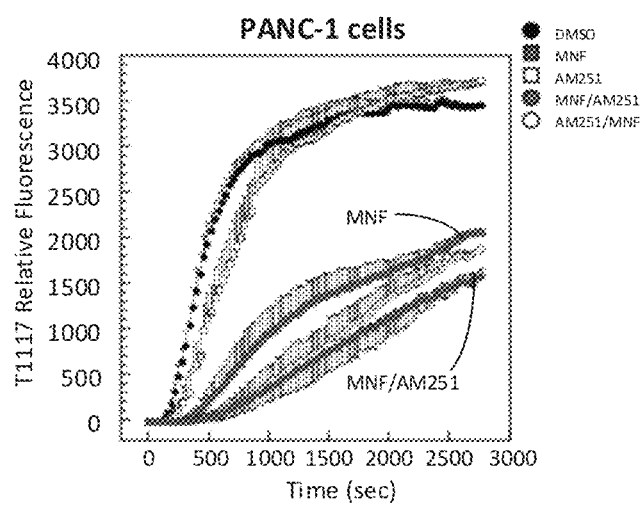
Figure 23D:
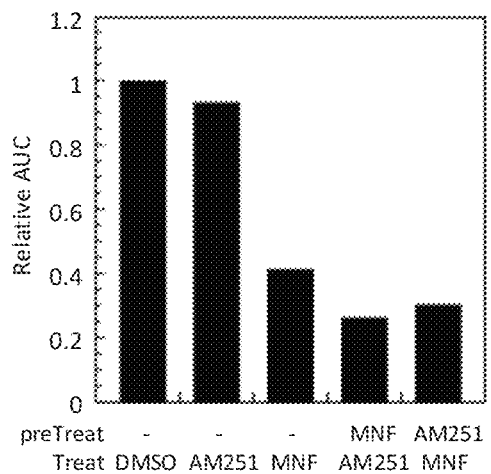

To investigate whether the effects of the compounds were unique to HepG2 cells, similar studies were conducted in PANC-1 cells in culture. Semi-quantitative PCR analysis indicated the presence of $CB_1R$, $CB_2R$ and GPR55 in these cells. The results indicated that MNF was a potent inhibitor of T1117 incorporation in PANC-1 cells (FIGS. 23C and 23D). Thus, it would appear that MNF blocked endocytosis of a GPR55 ligand.

Effect of MNF on GPR55 internalization and downstream signaling. The effect of MNF on ligand-induced GPR55 internalization was performed in HEK293 cells stably expressing HA-tagged GPR55. Using confocal laser scanning microscopy, GPR55 was found to be located largely at the plasma membrane of unstimulated cells (FIG. 24A). Addition of O-1602 for 20 minutes led to marked endocytosis of HA-tagged GPR55, which was blocked by pretreatment with MNF (FIG. 24B).

Additional events downstream of GPR55 internalization may be impaired by cell treatment with MNF, as the redistribution of ligand-bound receptors from the cell surface to endosomal compartment differentially regulates various signaling pathways and their associated biological outcomes. Indeed, spatio-temporal activation of extracellular signal-regulated kinase (ERK)-MAP kinase plays a role in the dynamic control of complex cellular functions. Here, exposure of HepG2 cells to O-1602 dose-dependently increased ERK phosphorylation and MNF pretreatment abrogated O-1602 responsiveness (FIGS. 25A and 25B). PANC-1 cells exhibited the same behavior as HepG2 cells, and displayed exquisite sensitivity to MNF with regard to O-1602-mediated ERK phosphorylation (FIGS. 25C and 25D). Similar findings were observed following cell stimulation with AM251 with and without MNF pretreatment.

Bioactive concentrations of endocannabinoids are present in fetal bovine serum (250-700 nM of 2-arachidonoylglycerol), which strongly influence monocytes/macrophage responses. As shown in FIGS. 26A-26D, pretreatment with MNF potently inhibited serum-induced ERK phosphorylation in both cell lines.

Figure 26A:
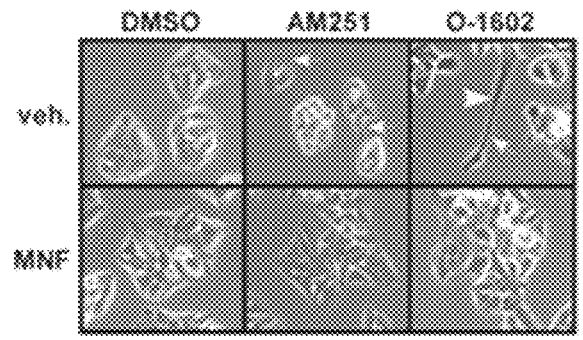
FIGS. 26A-26C show MNF interferes with inducible changes in cell morphology and expression of EGFR. Serum-starved HepG2 (FIG. 26A) and PANC-1 (FIG. 268) cells were pre-incubated in the presence of DMSO (0.1%) or MNF (1 µM) for 30 minutes followed by the addition of AM251 (5 µM) or O-1602 (5 µM) for 16 hours. Unstimulated PANC-1 cells displayed cuboidal morphology with and without MNF. White arrows show individual cells with filopodia.
Figure 26B:
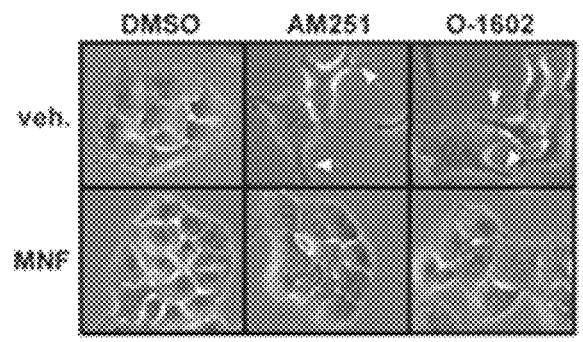
Figure 26C:
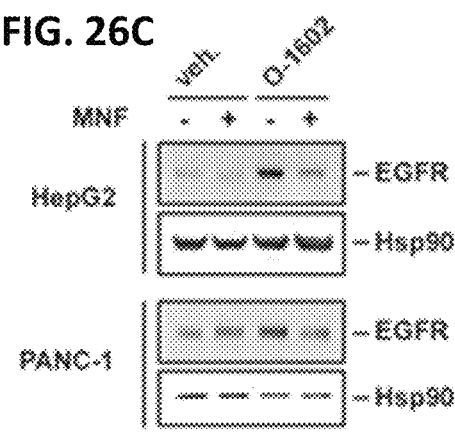

A role of MNF in the morphology and motility of tumor cells. To further study the role of MNF and GPR55 activation in HepG2 and PANC-1 cell biology, possible alteration in morphology was investigated. Cells with irregular appearance and long filipodia and lamellipodia were observed in response to AM251 and O-1602 stimulation (FIGS. 26A and 26B, white arrows). Pretreatment with MNF rendered the cells refractory to the change in morphology induced by AM251 and O-1602 in both tumor cell lines. As shown in FIG. 26C, treatment of HepG2 and PANC-1 cells with O-1602 led to higher EGFR levels when compared to vehicle-treated cells, and MNF blocked this effect (FIG. 26C, lane 4 vs. 3) and that of AM251. These findings are consistent with the idea that MNF conferred refractoriness to GPR55 signaling.

A wound-healing assay in vitro was then performed to investigate the effects of MNF on cell motility. As shown in FIGS. 27A and 29A, MNF alone had no effect on the motility of HepG2 cells at the concentration used throughout the study (1 µM). This is in contrast, however, to its significant inhibitory effect toward AM251-mediated increase in cell motility (FIGS. 27A, 29A). The relative wound surface area after 24-hour treatment of HepG2 cells with each condition depicted in FIG. 27B. Similar to its effects in HepG2 cells, MNF also produced significant decrease in AM251-induced motility of PANC-1 cells, but did not alter the constitutive rate of gap filling (FIGS. 27C, 27D and 29B). When tested against O-1602, a cell type-selective effect was observed in the presence of MNF. In particular, the ability of MNF to inhibit the wound closure evoked by O-1602 in PANC-1 cells was absent in HepG2 cells (FIG. 29C), indicative of a complex mode of antagonism.

Engagement of the 'cannabinoid-like receptor' GPR55 triggers a number of signaling cascades that promote cell proliferation, migration, survival and oncogenesis. MNF displays a number of characteristics associated with selective attenuation in GPR55 signaling, including 1) delayed cellular entry of a fluorescent GPR55 ligand, 2) inhibition of the internalization of the ligand-occupied GPR55, and 3) a significant reduction in GPR55 agonist efficacy with regard to a number of biological readouts.

In cellular assays, the low level of non-specific uptake of the fluorophore alone (5'-TAMRA-PPA) makes T1117 (5'-TAMRA-PPA-conjugated AM251) suitable for in vivo imaging approaches aimed at assessing occupancy and internalization of GPR55. The compound T1117 has been shown previously to measure the distribution of GPR55 in small mouse arteries. Here, employing the siRNA-based gene silencing method, it was determined that GPR55 was a main molecule responsible for T1117 entry in intact cells. In human HepG2 cells, the presence of GPR55 and the classical CB1R was evidenced by PCR and functional assays. Both receptors trigger distinct signaling pathways in endothelial cells, and it was thus not surprising to observe in our study that the silencing of CB1R by siRNA limited the response mediated by GPR55 while cell stimulation with an agonist of CB1R (WIN 55,212-2) resulted in an increase in GPR55 constitutive activity. Although GPR55 interacts cooperatively with CB2R to influence inflammatory responses of neutrophils, pharmacological inhibition and silencing of CB2R by siRNA failed to impact on T1117 incorporation in HepG2 cells. Thus, CB1R-triggered mechanism appears to contribute is some extent to the constitutive GPR55-mediated T1117 uptake. The propensity of $CB_1R$ to form functional heterodimers with various GPCRs explains some of the cell type-specific physiological responses of GPR55.

Analysis of the data revealed that MNF significantly delayed the cellular accumulation of T1117 in serum-depleted cells expressing endogenous levels of GPR55, indicative of a decrease in the binding affinity of T1117 to GPR55 and/or impairment in constitutive cell surface GPR55 internalization and recycling pathways. Pretreatment with AM251 for 30 minutes potentiated the effect of MNF, consistent with a negative cumulative event. In this model, AM251-bound GPR55 complexes were internalized and any residual cell surface GPR55 receptors were targeted by MNF, making this GPCR inaccessible for efficient T1117 binding and/or internalization. Alternatively, inhibition of CB1R by AM251 may have also contributed to the observed potency in MNF signaling. The ability of CP 55,940 to block cellular entry of T1117 was consistent with its role as a GPR55 antagonist.

The stimulation of GPR55-expressing HEK-293 cells with the atypical cannabinoid O-1602 triggered rapid internalization of GPR55 through a MNF-inhibitable mechanism, indicating that under the current assay conditions, the potency of MNF was not appreciably influenced by the conditions of overexpression. GPCR desensitization and internalization requires the participation of β-arrestin translocation to the activated receptor. Using a β-arrestin translocation assay in a transient transfection format, AM251 and its clinical analog rimonabant exhibit potent activity as GPR55 agonists, whereas CP 55,940 blocks the formation of β-arrestin/GPR55 complexes. The possibility exists that MNF prevents the recruitment of β-arrestin to the GPR55, thereby providing a negative impact on internalization and recycling of this GPCR after agonist exposure. In addition to its role in the promotion of GPCR internalization, β-arrestin is required for activation of downstream signaling (e.g., ERK activation). GPR55 is thought to bind predominantly G-protein G13, where it promotes Rho-dependent signaling in endothelial cells. Additional events downstream of GPR55 include activation of ERK and Ca2+ release from internal stores. Here, in vitro exposure of HepG2 and PANC-1 cells to AM251 or O-1602 resulted in rapid increase in ERK phosphorylation, a process that was inhibited by cell pretreatment with MNF. An explanation for the significant reduction in agonist-stimulated increase in ERK phosphorylation in response to MNF is that ligand-bound GPR55 stimulates ERK activity once the receptor is internalized, in contrast to an earlier study by Li and colleagues showing that opioid-mediated ERK activation is not dependent on K-opioid receptor internalization (*J. Biol. Chem.* 274: 12087-12094, 1999). Alternatively, MNF may interact with a putative allosteric binding site on GPR55 and elicit negative allosteric modulation of GPR55 agonists. It is noteworthy that an allosteric binding site has been reported at the $CB_1R$. MNF may inhibit signaling downstream of GPR55 to disrupt the binding of T1117, receptor internalization and induction of the signaling cascade leading to ERK activation.

Another striking observation from the disclosed study was the similarity between the effect of MNF on basal and agonist-induced ERK phosphorylation and on biological readouts, including GPR55-dependent cellular morphology and cell motility. ERK has been found to coordinate and regulate cell migration by promoting lamellipodial leading edge movement via phosphorylation of the WAVE2 regulatory complex. Here, treatment of HepG2 and PANC-1 cells with AM251 or O-1602 led to fillipodia extension, which was blocked by MNF pretreatment. Moreover, MNF elicited a significant reduction in the rate of wound closure for GPR55 agonists in HepG2 and PANC-1 cells using a scratch wound-healing assay.

This example indicates MNF reduced proliferation and increased apoptosis in human HepG2 hepatocellular carcinoma cells and PANC-1 pancreatic cancer cell line in culture. The role of GPR55 in MNF signaling in HepG2 and PANC-1 cells was investigated with a focus on internalization of the fluorescent ligand Tocrifluor 1117 (T1117), reorganization of actin cytoskeleton, and cell motility as measured by scratch assay. Results indicated that GPR55 knockdown by RNA interference markedly reduced cellular uptake of T1117, a process that was sensitive to MNF inhibition. GPR55 internalization mediated by the atypical cannabinoid O-1602 was blocked by MNF in GPR55-expressing HEK293 cells. Pretreatment of HepG2 and PANC-1 cells with MNF significantly abrogated the induction of ERK1/2 phosphorylation in response to AM251, 0-1602 and fetal bovine serum, known to contain bioactive lipids. Moreover, MNF exerted a coordinated negative regulation of AM251 and O-1602 inducible processes, including change in cell morphology and migration, using scratch-wound healing assay. Thus, these studies show for the first time that MNF impairs GPR55-mediated signaling and has therapeutic use in the management of cancer.

Example 10

Treatment of a CB Receptor Activity-Regulated Tumor

This example describes a method that can be used to treat a tumor in a human subject by administration of a composition comprising fenoterol, a fenoterol analogue or a combination thereof at a therapeutically effective amount to reduce or inhibit on or more signs or symptoms associated with the tumor, such as a glioblastoma or hepatocellular carcinoma. Although particular methods, dosages, and modes of administrations are provided, one skilled in the art will appreciate that variations can be made without substantially affecting the treatment.

A subject with a glioblastoma or hepatocellular carcinoma is selected based upon clinical symptoms. A biological sample is isolated from the subject and CB receptor expression, including GPR55, and β2-AR expression are determined by microarray, Western blotting or histological studies. A positive result indicates that the tumor may be treated by administration of fenoterol, a disclosed fenoterol analogue or a combination thereof. In one particular example, a tissue biopsy is obtained from a subject with a primary brain tumor. Expression of β2-AR and GPR55 is determined in the sample. The absence of β2-ARs and the presence of GPR55 in the sample indicates that the primary brain tumor can be treated by administration of a composition including (R,R')-MNF. The presence of β2-ARs and the presence of GPR55 indicates the tumor can be treated by (R,R')-MNF or fenoterol (or both) or other fenoterol analogue(s) known to stimulate β2-ARs activity. The composition including the desired compounds is intraperitoneally administered to the subject at a concentration of 30 mg/kg/day for the first 10 days and 50 mg/kg/day for the remaining 32 days. Tumor growth is then assessed 7 days, 14 days, 21 days, 30 days, and 42 days following treatment. In one example, the effectiveness of the treatment is determined by imaging methods, including non-invasive, high-resolution modalities, such as computed tomography (CT) and especially magnetic resonance imaging (MRI). For example, contrast agent uptake is monitored to determine the effectiveness of the treatment. A decrease in permeability to the blood-brain barrier marked by an at least twenty percent (20%) decrease in uptake of a contrast agent as compared to reference value or that measured prior to treatment indicates the treatment is effective. Also, a twenty-percent (20%) reduction in tumor size as compared to tumor size prior to treatment is considered to be an effective treatment. In one example, the therapeutic effectiveness is determined by measuring expression or activity of one or more molecules demonstrated herein to be regulated by MNF (see for example, Table 10). In some examples, a subject is administered an intravenous formulation of MNF used with a cGMP-produced (R,R')-4-methoxynaphthylfenoterol (such as a cGMP-produced (R,R')-4-methoxynaphthylfenoterol 2 Kg formulation). In some examples, a subject is administered an intravenous formulation of MNF at a concentration ranging from 0.1 to 10 mg/kg for 4 days as a single agent or in combination with other fenoterol analogs or standard agents used in cancer chemotherapy over a two week period as a continuous or pulsed therapy. In some examples, a subject is administered orally a 25 mg/kg dose of MNF formulated as a single agent or as a combination of (R,R')-MNF and other MNF stereoisomers or fenoterol stereoisomers on a daily basis for a certain period of time, such as 1 month, 2 months, 3 months, 4 months, 5 months, 6 months followed by additional periods if desired, based upon regression of or inhibition of tumor growth.

Example 11

Use of Disclosed Compositions Including (R,R')-MNF or (R,R')-NF (or Both) as an Adjuvant Therapy This example describes a method that can be used to reduce, prevent, or retard tumor growth in a human subject that has been treated for a malignant astrocytoma.

A subject with an astrocytoma is selected based upon clinical symptoms and determined to have an astrocytoma expressing CB-receptors. The primary form of treatment of the malignant astrocytoma is open surgery. For subjects that are not surgical candidates, either radiation or chemotherapy is used as the initial treatment. Following the initial treatment, a subject is administered a pharmaceutical composition containing (R,R')-MNF and/or (R,R')-NF orally daily for an indefinite period of time. The reoccurrence of tumor growth is monitored by imaging methods, including non-invasive, high-resolution modalities, such as CT and MRI.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of detecting and treating liver cancer or colon cancer, comprising:
   identifying a subject in need of treatment for liver cancer or colon cancer by detecting a liver cancer tumor or colon cancer tumor regulated by cannabinoid (CB) receptor activity in the subject; and
   administering to the subject a therapeutically effective amount of a compound to reduce tumor growth, reduce metastasis of the tumor, or a combination thereof, wherein the compound is optically active 4'-methoxy-l-naphthylfenoterol (MNF), naphthylfenoterol (NF), ethyl-4'-methoxy-l-naphthylfenoterol (ethylMNF), 4'-amino-l-naphthylfenoterol (aminoNF), 4'-hydroxy-l-naphthylfenoterol (hydroxyNF), ethyl-naphthylfenoterol (ethylNF), or any combination thereof.

2. The method of claim 1, wherein the CB receptor is GPR55.

3. The method of claim 1, wherein detecting the liver cancer tumor or colon cancer tumor regulated by CB receptor activity comprises:
   detecting altered CB expression or activity in a sample obtained from the subject, compared to CB expression or activity in the absence of a tumor; or
   detecting one or more clinical signs characteristic of the liver cancer tumor or colon cancer tumor; or
   diagnostic imaging; or
   histology; or
   any combination thereof.

4. The method of claim 3, wherein the diagnostic imaging comprises magnetic resonance imaging.

5. The method of claim 3, wherein the one or more clinical signs comprises vomiting, weight loss, or a combination thereof.

6. The method of claim 1, wherein the compound is an (R,R') or (R,S') isomer.

7. The method of claim 1, wherein the compound is (R,R')-MNF, (R,S')-MNF, (R,R')-NF, (R,S')-NF, or any combination thereof.

8. The method of claim 1, wherein administering to the subject the therapeutically effective amount of the compound comprises administering a pharmaceutical composition comprising the compound and a pharmaceutically acceptable carrier.

9. The method of claim 8, wherein the pharmaceutical composition is an injectable fluid or oral dosage form.

10. The method of claim 1, wherein the therapeutically effective amount of the compound is within a range from about 0.001 mg/kg to about 10 mg/kg body weight administered orally in single or divided doses.

11. The method of claim 1, wherein the therapeutically effective amount of the compound is from about 1 mg/kg to about 100 mg/kg body weight administered parenterally.

12. The method of claim 1, further comprising administering to the subject an additional chemotherapeutic agent prior to, concurrent with, or subsequent to administering the compound.

13. The method of claim 1, wherein the liver cancer is hepatocellular carcinoma.

14. The method of claim 1, wherein the colon cancer is colon carcinoma.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
```

<223> OTHER INFORMATION: synthetic oligonucleotide primer

<400> SEQUENCE: 1
cgtgggcagc ctgttcctca                                              20

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide primer

<400> SEQUENCE: 2
catgcgggct tggtctgg                                                18

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide primer sequence

<400> SEQUENCE: 3
cgccggaagc cctcatacc                                               19

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide primer sequence

<400> SEQUENCE: 4
cctcattcgg gccattcctg                                              20

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 5
accacagtcc atgccatc                                                18

<210> SEQ ID NO 6
<211> LENGTH: 18
<212> TYPE: DNA
<213> ORGANISM: Artificial Sequence
<220> FEATURE:
<223> OTHER INFORMATION: synthetic oligonucleotide primer sequence

<400> SEQUENCE: 6
tccaccaccc tgttgctg                                                18

<210> SEQ ID NO 7
<211> LENGTH: 23
<212> TYPE: DNA
<213> ORGANISM: Artificial Sequence
<220> FEATURE:
<223> OTHER INFORMATION: sythetic oligonucleotide primer sequence

<400> SEQUENCE: 7
catgtctctc atcgtcctgg cca                                          23

```
<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide primer sequence

<400> SEQUENCE: 8
cacgatggaa gaggcaatgg ca                                              22
```